(12) United States Patent
Hartigan-O'Connor

(10) Patent No.: US 12,409,220 B2
(45) Date of Patent: Sep. 9, 2025

(54) CONJUGATE POLYPEPTIDES AND VACCINES FOR INDUCING IMMUNE RESPONSES

(71) Applicant: The Regents of The University of California, Oakland, CA (US)

(72) Inventor: Dennis J. Hartigan-O'Connor, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 18/055,808

(22) Filed: Nov. 15, 2022

(65) Prior Publication Data

US 2023/0087396 A1   Mar. 23, 2023

Related U.S. Application Data

(63) Continuation of application No. PCT/US2021/033259, filed on May 19, 2021.

(60) Provisional application No. 63/058,362, filed on Jul. 29, 2020, provisional application No. 63/027,250, filed on May 19, 2020.

(51) Int. Cl.
| | |
|---|---|
| A61K 39/215 | (2006.01) |
| A61K 39/00 | (2006.01) |
| A61P 31/14 | (2006.01) |
| C12N 15/86 | (2006.01) |

(52) U.S. Cl.
CPC ..... A61K 39/215 (2013.01); A61K 39/001111 (2018.08); A61P 31/14 (2018.01); C12N 15/86 (2013.01); A61K 2039/53 (2013.01); A61K 2039/6056 (2013.01); C12N 2710/16143 (2013.01)

(58) Field of Classification Search
CPC .......... A61K 39/215; A61K 39/001111; A61K 2039/53; A61K 2039/6056; A61K 39/12; A61K 2039/57; A61K 2039/575; A61K 2039/6031; A61P 31/14; C12N 15/86; C12N 2710/16143; C12N 2740/15034; C12N 2770/20034
See application file for complete search history.

(56) References Cited

U.S. PATENT DOCUMENTS

| | | | | |
|---|---|---|---|---|
| 6,406,696 | B1 * | 6/2002 | Bluestone | C07K 14/005 414/141.1 |
| 2009/0227658 | A1 | 9/2009 | Huang et al. | |
| 2010/0322929 | A1 | 12/2010 | Zurawski et al. | |
| 2016/0068605 | A1 | 3/2016 | Nemeth et al. | |
| 2019/0352373 | A1 | 11/2019 | Connolly et al. | |

FOREIGN PATENT DOCUMENTS

| | | | |
|---|---|---|---|
| WO | 91/06319 A1 | 5/1991 | |
| WO | 2021/236841 A2 | 11/2021 | |
| WO | WO-2021222772 A2 * | 11/2021 | ........... C07K 14/005 |

OTHER PUBLICATIONS

CD3_Mouse_anti-Human_Fisher_Scientific-Downloaded-Jun. 7, 2023 (Year: 2023).*
Hachim et al. Beyond the Spike: identification of viral targets of the antibody response to SARS-CoV-2 in COVID-19 patients. medRxiv preprint doi: https://doi.org/10.1101/2020.04.30.20085670; this version posted May 2, 2020. (Year: 2020).*
Hust et al. Single chain Fab (scFab) fragment. BMC Biotechnol. Mar. 8, 2007;7:14. (Year: 2007).*
Redwood et al. Use of a murine cytomegalovirus K181-derived bacterial artificial chromosome as a vaccine vector for immunocontraception. J Virol. Mar. 2005;79(5):2998-3008. (Year: 2005).*
Chen et al. Structure of the transmembrane domain of HIV-1 envelope glycoprotein. FEBS J. Apr. 2017;284(8):1171-1177. (Year: 2017).*
Bhattacharya et al. Nanodisc-incorporated hemagglutinin provides protective immunity against influenza virus infection. J Virol. Jan. 2010;84(1):361-71. (Year: 2010).*
Vabret et al. Immunology of COVID-19: Current State of the Science. Immunity. Jun. 16, 2020;52(6):910-941. doi: 10.1016/j.immuni.2020.05.002. Epub May 6, 2020. (Year: 2020).*
Hajirezaei M, Darbouy M, Kazemi B. Cloning and expression of the functional human anti-vascular endothelial growth factor (VEGF) using the pcDNA3. 1 vector and the human chronic myelogenous leukemia cell line K562. Protein J. Feb. 2014;33(1):100-9. (Year: 2024).*
Hexham JM, Dudas D, Hugo R, Thompson J, King V, Dowling C, Neville DM Jr, Digan ME, Lake P. Influence of relative binding affinity on efficacy in a panel of anti-CD3 scFv immunotoxins. Mol Immunol. Sep. 2001;38(5):397-408. (Year: 2001).*
Mouquet H, Warncke M, Scheid JF, Seaman MS, Nussenzweig MC. Enhanced HIV-1 neutralization by antibody heteroligation. Proc Natl Acad Sci U S A. Jan. 17, 2012;109(3):875-80. (Year: 2012).*
Choi JH, Yu NK, Baek GC, Bakes J, Seo D, Nam HJ, Baek SH, Lim CS, Lee YS, Kaang BK. Optimization of AAV expression cassettes to improve packaging capacity and transgene expression in neurons. Mol Brain. Mar. 11, 2014;7:17. (Year: 2014).*
Ahmad ZA, Yeap SK, Ali AM, Ho WY, Alitheen NB, Hamid M. scFv antibody: principles and clinical application. Clin Dev Immunol. 2012;2012:980250. doi: 10.1155/2012/980250. Epub Mar. 15, 2012. (Year: 2012).*
Du J, Cao Y, Liu Y, Wang Y, Zhang Y, Fu G, Zhang Y, Lu L, Luo X, Kim CH, Schultz PG, Wang F. Engineering Bifunctional Antibodies with Constant Region Fusion Architectures. J Am Chem Soc. Dec. 27, 2017;139(51):18607-18615. (Year: 2017).*

(Continued)

*Primary Examiner* — Nicole Kinsey White
*Assistant Examiner* — Ruixue Wang
(74) *Attorney, Agent, or Firm* — Kilpatrick Townsend & Stockton LLP

(57) ABSTRACT

Methods and compositions are disclosed for inducing immune responses against one or more antigens in a mammal.

27 Claims, 13 Drawing Sheets

Specification includes a Sequence Listing.

(56) References Cited

OTHER PUBLICATIONS

UniProtKB Accession No. P0DTC2 "Spike glycoprotein", Available online at: https://www.uniprot.org/uniprot/P0DTC2, Apr. 22, 2020, 28 pages.

International Application No. PCT/US2021/033259, Invitation to Pay Additional Fees and, Where Applicable, Protest Fee, mailed Sep. 7, 2021, 3 pages.

International Application No. PCT/US2021/033259, International Search Report and Written Opinion, mailed Nov. 4, 2021, 21 pages.

International Application No. PCT/US2021/033259, International Preliminary Report on Patentability, mailed Dec. 1, 2022, 15 pages.

Tang et al., "A High Affinity Digoxin-binding Protein Displayed on M13 is Functionally Identical to the Native Protein", vol. 270, No. 14, The Journal of Biological Chemistry, Apr. 7, 1995, pp. 7829-7835.

Wu et al., "A New Coronavirus Associated with Human Respiratory Disease in China", Nature, vol. 579, No. 7798, Mar. 2020, pp. 265-269, 20 pages.

Bishop, G.A. et al.; The CD40-CD154 interaction in B cell-T cell liaisons; Cytokine & Growth Factor Reviews; 14 (2003) 297-309.

Imai, A. et al.; A novel fully human anti-CD40 monoclonal antibody, 4D11, for kidney transplantation in cynomolgus monkeys; Transplantation; vol. 84, No. 8 (2007) 1020-1028.

Vinuesa, C.G. et al.; T cells and follicular dendritic cells in germinal center B-cell formation and selection; Immunological Reviews; vol. 237 (2010) 72-89.

EP21808322.8, "Extended European Search Report", Apr. 23, 2024, 11 pages.

Muralidharan et al., "Targeting CD40 enhances antibody- and CD8-mediated protection against respiratory syncytial virus infection", Scientific Reports, vol. 8, No. 1, Nov. 9, 2018, pp. 1-13.

Saha et al., "Repurposing Drugs, Ongoing Vaccine, and New Therapeutic Development Initiatives Against COVID-19", Frontiers in Pharmacology, vol. 11, Article 1258, Aug. 19, 2020, pp. 1-33.

Kim et al., "Therapy for Early COVID-19: A Critical Need", JAMA, vol. 324, No. 21, Dec. 1, 2020, pp. 2149-2150.

GenBank Accession No. NC_045512, "Severe acute respiratory syndrome coronavirus 2 isolate Wuhan-Hu-1, complete genome", Available online at: https://www.ncbi.nlm.nih.gov/nuccore/1798174254?sat=48&satkey=91704818>Mar. 30, 2020, Mar. 30, 2020, 12 pages.

\* cited by examiner

FIG. 5

| Group (DNA prime) | # macaques | DNA weight | Boost vector | Boost dose |
|---|---|---|---|---|
| S1 | 3 | 1 mg | Ad35/S1 | $10^{12}$ vp |
| RBD | 3 | 1 mg | Ad35/RBD | $10^{12}$ vp |
| s3-RBD | 3 | 1 mg | Ad35/RBD | $10^{12}$ vp |

RBD(B.1.351)

s3-RBD(B.1.351)-PDGFRtm

No plasmid

1dCD58-RBD(B.1.351)

CONJUGATE POLYPEPTIDES AND VACCINES FOR INDUCING IMMUNE RESPONSES

CROSS-REFERENCE TO RELATED APPLICATIONS

This application is a continuation of International Application No. PCT/US2021/033259, filed May 19, 2021, which claims priority to U.S. Provisional Application No. 63/027,250, filed May 19, 2020, and U.S. Provisional Application No. 63/058,362, filed Jul. 29, 2020, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. R01 AI118451, awarded by the National Institutes of Health (NIH). The Government has certain rights in the invention.

SEQUENCE LISTING

A Sequence Listing conforming to the rules of WIPO Standard ST.26 is incorporated herein by reference in its entirety. The electronic Sequence Listing file, entitled "070772-229520US-1358013_ST26.xml", was created on Nov. 7, 2022, and is 69,406 bytes in size.

BACKGROUND

Traditional vaccine development for previously unknown pathogens takes years, but preservation of human health may require a faster response—on the scale of months (1). Accelerated development is complicated, however, by multiple factors, including the lack of adequate animal models for emerging pathogens; the danger of antibody-dependent enhancement of infectivity (ADEI), which can occur whenever sub-optimal antibody responses are induced (2); and by the difficulty of developing new manufacturing processes for subunit, attenuated, or vectored vaccines. In addition, though induction of high-titer neutralizing antibodies (nAbs) would seem an obvious approach, we do not know what titer of nAbs would be protective in practice, nor how this threshold varies across the extremes of age and comorbidities.

With respect to SARS-CoV-2, the immune correlates of successful vaccination are poorly defined. Most coronavirus vaccines presently under development target the most variable part of the spike glycoprotein and induce antibody responses only against the virus present in the vaccine. In SARS-CoV-1, escape mutants develop in the presence of single anti-receptor binding domain (RBD) nAbs or combinations of two nAbs, both in vitro and in mice (2,3). In addition, as noted above, vaccines that exclusively elicit antibodies must additionally be approached with caution due to possible ADEI, especially when antibody levels are low (4). Indeed, highly concentrated antisera against SARS-CoV-1 were shown to neutralize virus infectivity, whereas diluted antibodies caused ADEI in human promonocyte cultures, leading to cytopathic effects and increased levels of TNF-α, IL-4, and IL-6 (5-7). Further, vaccine candidates based on the full-length SARS-CoV-1 spike were demonstrated to induce non-neutralizing antibodies, and the immunized animals were not protected. Instead they experienced adverse effects like enhanced hepatitis, increased morbidity, and stronger inflammatory responses (8,9).

T-cell responses elicited by CoV vaccines also play crucial roles in protection and clearance. Clearance of MERS-CoV infection was impossible in T cell-deficient mice, but was achieved in mice lacking B cells (10). Further, airway memory $CD4^+$ T cells were shown to mediate protective immunity against SARS-CoV-1 and MERS-CoV (11). However, most vaccine types do not elicit large numbers of memory $CD4^+$ T cells.

CMV-vectored vaccines can elicit robust antibody responses. Although CMV vaccines elicit weak antibody responses to some transgenes driven by heterologous promoters, CMV infections and vaccinations elicit robust antibody responses to proteins expressed under control of the endogenous pp65b promoter. It has been found, for example, that rhesus macaques vaccinated with a CMV vaccine carrying the Ebola virus glycoprotein (GP) under control of the pp65b promoter can produce GP-specific antibodies (21).

Another important characteristic of CMV vectors for their use against emerging pathogens is the capacity for re-administration to previously exposed individuals. Due to this ability, one can imagine repeated use of CMV-vectored vaccines to protect against a series of emerging threats over time.

Despite their immunologic advantages, however, practical obstacles prevent rapid development of CMV vaccines for human clinical use, when those vaccines are delivered as live virus. One obstacle is the tremendous difficulty of producing a uniform test article, at scale, from a slow-growing and mutable betaherpesvirus (29).

There is thus a need for new, safe, effective, and scalable vaccines and vaccination methods that provide for robust antibody responses against pathogens such as SARS-CoV-2, and that potentially enhance T-cell responses as well. The present disclosure addresses this need and provides other advantages as well.

BRIEF SUMMARY

In one aspect, the present disclosure provides a vaccine for inducing an immune response against a pathogen in a mammal, the vaccine comprising a conjugate polypeptide comprising an antigen from the pathogen, linked to a ligand or antibody fragment that specifically binds to a surface protein present on an immune cell.

In some embodiments, the surface protein is an abundant T-cell surface protein involved in signal transduction and/or adhesion. In some embodiments, the abundant T-cell surface protein is CD2, CD3, CD4, or CD5. In some embodiments, the abundant T-cell surface protein is CD2 or CD3. In some embodiments, the immune cell is a T cell or an antigen presenting cell (APC). In some embodiments, the ligand is an ectodomain of a cell adhesion molecule. In some embodiments, the cell adhesion molecule is CD58. In some embodiments, the surface protein is preferentially or only expressed by T cells. In some embodiments, the antibody fragment is an antibody-derived scFv chain.

In some embodiments, the conjugate polypeptide further comprises a lipid anchor, a transmembrane segment, a multimerizing domain, or any combination of these elements. In some embodiments, the lipid anchor is a glycosylphosphatidylinositol anchor. In some embodiments, the addition of a lipid anchor is directed by a signal sequence. In some embodiments, the signal sequence is derived from CD55. In some embodiments, the transmembrane segment is derived from a PDGF receptor, glycophorin A, or SARS-CoV-2 spike protein. In some embodiments, the multimerizing domain is derived from T4 fibritin. In some embodiments, the multimerizing domain is an Fc domain. In some embodiments, the Fc domain is located at the C-terminus of the conjugate polypeptide. In some embodiments, the Fc domain is a human IgG1 Fc domain. In some embodiments, the conjugate polypeptide is a fusion protein comprising the antigen and the ligand or antibody fragment within a single polypeptide chain.

In some embodiments, the antibody fragment is an antibody-derived scFv chain, and the VH and VL regions of the scFv are separated by a flexible linker. In some embodiments, the flexible linker is 12 or more amino acids long, and the conjugate polypeptide preferentially binds to the surface protein as a monomer. In some embodiments, the flexible linker is shorter than 12 amino acids long, and the conjugate polypeptide preferentially binds to the surface protein as a multimer. In some embodiments, the multimer is stabilized by disulfide bonds between monomer units. In some embodiments, the flexible linker is 5 amino acids long. In some embodiments, the conjugate polypeptide further comprises a tPA leader sequence. In some embodiments, the tPA leader sequence is 23 amino acids long.

In some embodiments, the vaccine further comprises a second antigen from the pathogen. In some embodiments, the pathogen is a virus. In some embodiments, the virus is SARS-CoV-2. In some embodiments, the antigen present within the conjugate polypeptide comprises a SARS-CoV-2 spike glycoprotein, or a fragment thereof. In some embodiments, the fragment of the SARS-CoV-2 spike glycoprotein comprises an S1 domain or a receptor-binding domain (RBD). In some embodiments, the second antigen comprises a SARS-CoV-2 E, M, N, nsp3, nsp4, or nsp6 protein, or a fragment of one of these proteins. In some embodiments, the second antigen comprises a fusion protein comprising SARS-CoV-2 E and M proteins, or fragments thereof. In some embodiments, the mammal is a human. In some embodiments, the vaccine is formulated for subcutaneous injection. In some embodiments, the conjugate polypeptide comprises an amino acid sequence selected from the group consisting of SEQ ID NO:1, SEQ ID NO:6, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, and SEQ ID NO:27.

In another aspect, the present disclosure provides a vaccine for inducing an immune response against a pathogen in a mammal, the vaccine comprising a polynucleotide encoding a conjugate polypeptide comprising an antigen from the pathogen fused to a ligand or antibody fragment that specifically binds to a surface protein present on an immune cell.

In some embodiments of the vaccine, the surface protein is an abundant T-cell surface protein involved in signal transduction and/or adhesion. In some embodiments, the abundant T-cell surface protein is CD2, CD3, CD4, or CD5. In some embodiments, the abundant T-cell surface protein is CD2 or CD3. In some embodiments, the immune cell is a T cell or an antigen presenting cell (APC). In some embodiments, the ligand is an ectodomain of a cell adhesion molecule. In some embodiments, the cell adhesion molecule is CD58. In some embodiments, the surface protein is preferentially expressed by T cells. In some embodiments, the antibody fragment is an antibody-derived scFv chain. In some embodiments, the conjugate polypeptide further comprises a lipid anchor, a transmembrane segment, a multimerizing domain, or any combination of these elements. In some embodiments, the lipid anchor is a glycosylphosphatidylinositol anchor. In some embodiments, the addition of a lipid anchor is directed by a signal sequence. In some embodiments, the signal sequence is derived from CD55. In some embodiments, the transmembrane segment is derived from PDGF receptor, glycophorin A, or the SARS-CoV-2 spike protein. In some embodiments, the multimerizing domain is derived from T4 fibritin. In some embodiments, the multimerizing domain is an Fc domain. In som embodiments, the Fc domain is located at the C-terminus of the conjugate polypeptide. In some embodiments, the Fc domain is a human IgG1 Fc domain.

In some embodiments, the VH and VL regions of the scFv are separated within the conjugate polypeptide by a flexible linker. In some embodiments, the flexible linker is 12 or more amino acids long, and wherein the conjugate polypeptide preferentially binds to the surface protein as a monomer. In some embodiments, the flexible linker is shorter than 12 amino acids long, and the conjugate polypeptide preferentially binds to the surface protein as a multimer. In some embodiments, the multimer is stabilized by disulfide bonds. In some embodiments, the flexible linker is 5 amino acids long. In some embodiments, the conjugate polypeptide comprises a tPA leader sequence. In some embodiments, the tPA leader sequence is 23 amino acids long.

In some embodiments, the vaccine further comprises a second polynucleotide encoding a second antigen from the pathogen. In some embodiments, the pathogen is a virus. In some embodiments, the virus is SARS-CoV-2. In some embodiments, the antigen present within the conjugate polypeptide comprises a SARS-CoV-2 spike glycoprotein or a fragment thereof. In some embodiments, the fragment of the SARS-CoV-2 spike glycoprotein comprises an S1 domain or a receptor-binding domain (RBD). In some embodiments, the second antigen comprises a SARS-CoV-2 E, M, N, nsp3, nsp4, or nsp6 protein, or a fragment of one of these proteins. In some embodiments, the second antigen comprises a fusion protein comprising SARS-CoV-2 E and M proteins, or fragments thereof. In some embodiments, the mammal is a human. In some embodiments, the vaccine is formulated for electroporation or subcutaneous injection.

In some embodiments, the polynucleotide encoding the conjugate polypeptide and/or the second polynucleotide encoding the second antigen are codon optimized. In some embodiments, the polynucleotide encoding the conjugate polypeptide is present within a first expression cassette, wherein the polynucleotide is operably linked to a first promoter, and/or the second polynucleotide encoding the second antigen is present within a second expression cassette, wherein the second polynucleotide is operably linked to a second promoter. In some embodiments, the second promoter is a mammalian promoter. In some embodiments, the mammalian promoter is an EF-1 alpha promoter. In some embodiments, the first and/or second expression cassettes are present within a vector. In some embodiments, the vector is administered as naked DNA. In some embodiments, the vector is a viral vector. In some such embodiments, the viral vector is a cytomegalovirus (CMV), adenovirus, or adeno-associated virus (AAV) vector. In some embodiments, the vaccine further comprises an in vivo transfection reagent. In some such embodiments, the in vivo transfection reagent is in vivo-jetPEI™. In some embodiments, the vaccine is formulated for subcutaneous transfection.

In some embodiments, the vector is a circular CMV vector comprising: (a) a CMV genome or a portion thereof, wherein the CMV genome or portion thereof contains the first expression cassette or the first and second expression cassettes; (b) a bacterial artificial chromosome (BAC) sequence comprising an origin of replication; (c) a first terminase complex recognition locus (TCRL1), comprising at least two viral direct repeat sequences; and (d) a second terminase complex recognition locus (TCRL2), comprising at least two viral direct repeat sequences; wherein the CMV genome or portion thereof is flanked by TCRL1 and TCRL2, defining a first region of the circular vector that extends from TCRL1 to TCRL2 and comprises the CMV genome or portion thereof; and wherein the BAC sequence is located in a second region of the circular vector that extends from TCRL1 to TCRL2 and does not comprise the CMV genome or portion thereof.

In some embodiments, the vector is a circular CMV vector comprising: (a) a CMV genome or a portion thereof, wherein the CMV genome or portion thereof contains the first expression cassette or the first and second expression cassettes; (b) a sequence comprising an origin of replication that functions in a single-celled organism; (c) one or more terminase complex recognition loci (TCRL) comprising a recombinantly introduced polynucleotide sequence that can direct cleavage by an HV terminase complex; wherein the CMV genome or portion thereof is separated from the sequence comprising an origin of replication by a TCRL; wherein the CMV genome or portion thereof abuts a TCRL at at least one extremity; and wherein the sequence comprising the origin of replication abuts a TCRL at at least one extremity.

In some embodiments, one or more of the terminase complex recognition loci comprises a Pac1 site and a Pac2 site. In some embodiments, all of the terminase complex recognition loci comprise a Pac1 site and a Pac2 site. In some embodiments, the first promoter is a viral promoter. In some embodiments, the viral promoter is a pp65b promoter. In some embodiments, the vector is a CMV vector, and the CMV is Towne HCMV. In some embodiments, the polynucleotide encoding the conjugate polypeptide comprises a nucleotide sequence selected from the group consisting of SEQ ID NO:2, SEQ ID NO:7, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NO:28.

In another aspect, the present disclosure provides a conjugate polypeptide comprising an antigen from a pathogen linked to a ligand or antibody fragment that specifically binds to a surface protein present on an immune cell.

In some embodiments of the conjugate polypeptide, the surface protein is CD2, CD3, CD4, or CD5. In some embodiments, the surface protein is CD2 or CD3. In some embodiments, the immune cell is a T cell or an antigen presenting cell (APC). In some embodiments, the ligand is an ectodomain of a cell adhesion molecule. In some embodiments, the cell adhesion molecule is CD58. In some embodiments, the surface protein is an abundant T-cell surface protein involved in signal transduction and/or adhesion. In some embodiments, the ligand or antibody fragment specifically binds to a surface protein preferentially or only expressed by T cells. In some embodiments, the antibody fragment is an antibody-derived scFv chain.

In some embodiments, the conjugate polypeptide further comprises a lipid anchor, a transmembrane segment, a multimerizing domain, or any combination of these elements. In some embodiments, the lipid anchor is a glycosylphosphatidylinositol anchor. In some embodiments, the addition of a lipid anchor is directed by a signal sequence. In some embodiments, the signal sequence is derived from CD55. In some embodiments, the transmembrane segment is derived from a PDGF receptor, glycophorin A, or SARS-CoV-2 spike protein. In some embodiments, the multimerizing domain is derived from T4 fibritin. In some embodiments, the multimerizing domain is an Fc domain. In some embodiments, the Fc domain is located at the C-terminus of the conjugate polypeptide. In some embodiments, the Fc domain is a human IgG1 Fc domain.

In some embodiments, the antibody fragment is an antibody-derived scFv chain, and the VH and VL regions of the scFv are separated by a flexible linker. In some embodiments, the flexible linker is 12 or more amino acids long, and wherein the conjugate polypeptide preferentially binds to the surface protein as a monomer. In some embodiments, the flexible linker is shorter than 12 amino acids long, and wherein the conjugate polypeptide preferentially binds to the surface protein as a multimer. In some embodiments, the multimer is stabilized by disulfide bonds between monomer units. In some embodiments, the flexible linker is 5 amino acids long. In some embodiments, the conjugate polypeptide further comprises a tPA leader sequence. In some embodiments, the tPA leader sequence is 23 amino acids long.

In some embodiments, the pathogen is a virus. In some such embodiments, the virus is SARS-CoV-2. In some embodiments, the antigen comprises a SARS-CoV-2 spike glycoprotein or a fragment thereof. In some embodiments, the fragment of the SARS-CoV-2 spike glycoprotein comprises an S1 domain or a receptor-binding domain (RBD). In some embodiments, the conjugate polypeptide comprises an amino acid sequence selected from the group consisting of SEQ ID NO: 1, SEQ ID NO:6, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, and SEQ ID NO:27.

In another aspect, the present disclosure provides a conjugate polypeptide comprising (i) a tissue plasminogen activator (tPA) signal sequence; (ii) a single-chain variable fragment (scFv) specifically binding to CD2, CD3, or CD4; (iii) a flexible linker; and (iv) a SARS-CoV-2 receptor binding domain (RBD).

In some embodiments, the conjugate polypeptide comprises the amino acid sequence of SEQ ID NO:6, SEQ ID NO: 9, SEQ ID NO:11, SEQ ID NO:13, SEQ ID NO:15, SEQ ID NO:17, SEQ ID NO:19, SEQ ID NO:21, SEQ ID NO:23, SEQ ID 25, or SEQ ID NO:27.

In another aspect, the present disclosure provides a polynucleotide encoding any of the herein-described conjugate polypeptides.

In some embodiments, the polynucleotide is codon optimized. In some embodiments, the polynucleotide comprises the nucleotide sequence of SEQ ID NO:2, SEQ ID NO:7, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NO:28.

In another aspect, the present disclosure provides an expression cassette comprising any of the herein-described polynucleotides. In some embodiments, the expression cassette comprises the nucleotide sequence of SEQ ID NO:8.

In another aspect, the present disclosure provides a vector comprising any of the herein-described polynucleotides or expression cassettes.

In some embodiments, the vector is a plasmid. In some embodiments, the vector is an adenoviral vector.

In another aspect, the present disclosure provides any of the herein-described diabodies, triabodies, tetrabodies, or dimers.

In another aspect, the present disclosure provides a vaccine comprising any of the herein-described conjugate polypeptides, polynucleotides, antigens, expression cassettes, vectors, diabodies, triabodies, tetrabodies, or dimers.

In another aspect, the present disclosure provides a method of inducing an immune response against a pathogen in a mammal, the method comprising administering to the mammal any of the herein-described vaccines.

In some embodiments, the vaccine is administered subcutaneously or by electroporation. In some embodiments, the method induces a neutralizing antibody response in the mammal against the antigen present within the conjugate polypeptide, and the neutralizing response is substantially greater than any antibody-dependent enhancement of infectivity (ADEI) induced in the mammal by the vaccine. In some embodiments, the vaccine does not substantially induce ADEI in the mammal. In some embodiments, the method induces both CD4+ and CD8+ T cell responses against the second antigen.

In some embodiments, the method comprises administering to the mammal by electroporation of a DNA prime comprising any of the herein-described vectors, e.g., a plasmid, encoding any of the herein-described conjugate polypeptides, followed by a boost with any of the herein-described vectors, e.g., an adenoviral vector, encoding any of the herein-described antigens, e.g., RBD. In some embodiments, the boost is performed after about 28 days. In some embodiments, the mammal is a human.

Numerous embodiments of the present disclosure, including compositions and methods for their preparation and administration, are presented herein.

BRIEF DESCRIPTION OF THE DRAWINGS

FIG. 3A: Balance of CD4 and CD8 responses following adenovirus- vs. CMV-vectored immunization. CMV vaccines (faint solid lines for individual traces; dark solid line for median) elicit comparable CD4 and CD8 responses (ratio >1) while adenoviral vectors elicit a lower relative frequency of CD4 responses (dotted lines). FIG. 3B: Example of balanced CD4+ and CD8+ T-cell responses following CMV-vectored immunization (top) but not adenovirus-vectored immunization (bottom). Shown are CD4+ or CD8+ cells (left and right, respectively) responding to vaccine antigen stimulation with cytokine production, two weeks after immunization.

FIG. 5. B cells reactive with anti-CD3-linked immunogen receive indiscriminate help.

Figure 1:
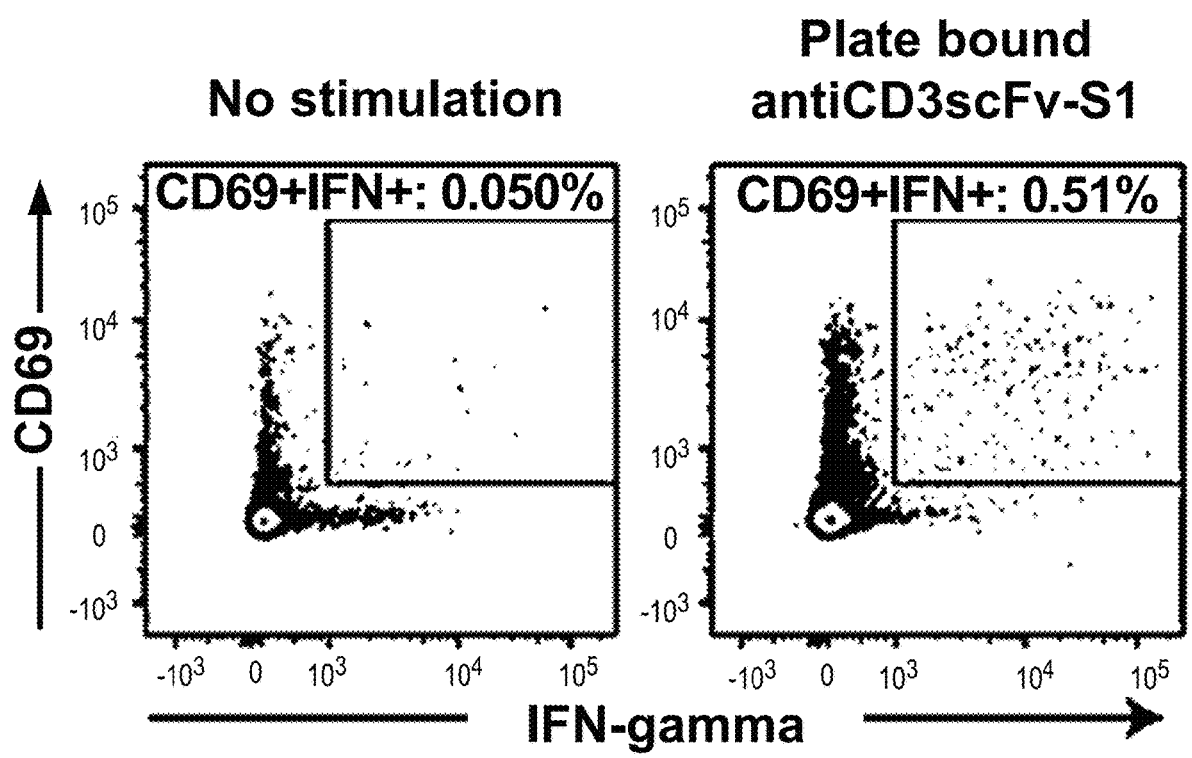
FIG. 1. Stimulation of T cells by anti-CD3 scFv linked to the SARS-CoV-2 S1 domain. Left, incubation of T cells in culture without stimulation leads to limited CD69 expression on the cell surface and negligible interferon-gamma production. Right, incubation of T cells in the presence of plate-bound antiCD3scFv-S1 leads to increased CD69 and interferon production, indicating that the antiCD3scFv-S1 molecule is capable of engaging CD3 complex and activating T-cell signaling. Scales run from $-10^3$ to $10^5$ on both the x and y axes.

Further examples of desired, intended, and/or protective immune responses that can be induced according to recombinant polynucleotides, compositions, and methods of the present disclosure include, but are not limited to, those involving class Ia-, class Ib-, or class II-restricted CD4$^+$ T cells; class Ia-, class Ib-, or class II-restricted CD8$^+$ T cells; cytokine-producing T cells (e.g., T cells that produce IFN-gamma, TNF-alpha, IL-1-beta, IL-2, IL-4, IL-5, IL-10, IL-13, IL-17, IL-18, or IL-23); CCR7$^-$CD8$^+$ T cells (e.g., effector-memory cells); CXCR5$^+$ T cells (i.e., those homing to B cell follicles); CD4$^+$ regulatory T cells; CD8$^+$ regulatory T cells; antigen-specific T follicular helper cells; antibody production; NK cells; NKG2C$^+$ NK cells; CD57$^+$ NK cells; FcR-gamma-negative NK cells; and NK-CTL cells, i.e., CD8$^+$ T cells expressing molecules typical of NK cells, such as NKG2A.

The term "cytomegalovirus" or "CMV" refers to viruses that include members of the Cytomegalovirus genus of viruses (within the order Herpesvirales, family Herpesviridae, subfamily Betaherpesvirinae). The term includes, but is not limited to, Human cytomegalovirus (HCMV; also known as Human herpesvirus 5 (HHV-5)), Simian cytomegalovirus (SCCMV or AGMCMV), Baboon cytomegalovirus (BaCMV), Owl monkey cytomegalovirus (OMCMV), Squirrel monkey cytomegalovirus (SMCMV), and Rhesus cytomegalovirus (RhCMV) that infects macaques.

The term "antigen-presenting cell" or "APC" refers to a cell that displays or presents an antigen, or a portion thereof, on the surface of the cell. Typically, antigens are displayed or presented with a major histocompatibility complex (MHC) molecule. Almost all cell types can serve as APCs, and APCs are found in a large number of different tissue types. Professional APCs, such as dendritic cells, macrophages, and B cells, present antigens to T cells in a context that most efficiently leads to their activation and subsequent proliferation. Many cell types present antigens to cytotoxic T cells.

An "immune cell" can be any cell of the immune system, including T cells such as helper T cells, CD4$^+$ T cells, CD8$^+$ T cells, TH1, TH2, TH17, and Treg cells, antigen presenting cells (APCs), B cells, granulocytes including basophils, eosinophils, and neutrophils, mast cells, monocytes, macrophages, dendritic cells, and natural killer (NK) cells.

An "infectious disease antigen" refers to any molecule originating from an infectious disease-causing organism that can induce an immune response (e.g., in a subject). For example, an infectious disease antigen can originate from a virus, bacterium, fungus, protozoan, helminth, or parasite, and can be, for example, a bacterial wall protein, a viral capsid or structural protein (e.g., a retroviral envelope protein, such as an HIV or SIV env protein), or a portion thereof. In some embodiments, the infectious disease antigen is a viral infectious disease antigen from SARS-CoV-2.

As used herein, the terms "polynucleotide," "nucleic acid," and "nucleotide," refer to deoxyribonucleic acids (DNA) or ribonucleic acids (RNA) and polymers thereof. The term includes, but is not limited to, single-, double-, or multi-stranded DNA or RNA, genomic DNA, cDNA, and DNA-RNA hybrids, as well as other polymers comprising purine and/or pyrimidine bases or other natural, chemically modified, biochemically modified, non-natural, synthetic, or derivatized nucleotide bases. Unless specifically limited, the term encompasses nucleic acids containing known analogs of natural nucleotides that have similar binding properties as the reference nucleic acid. Unless otherwise indicated, a particular nucleic acid sequence also implicitly encompasses conservatively modified variants thereof (e.g., degenerate codon substitutions), homologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "vector" and "expression vector" refer to a nucleic acid construct, generated recombinantly or synthetically, with a series of specified nucleic acid elements that permit transcription of a particular nucleic acid sequence (e.g., encoding an antigen and/or fusion protein as described herein) in a host cell or engineered cell. In some embodiments, a vector includes a polynucleotide to be transcribed, operably linked to a promoter. Other elements that may be present in a vector include those that enhance transcription (e.g., enhancers), those that terminate transcription (e.g., terminators), those that confer certain binding affinity or antigenicity to a protein (e.g., recombinant protein) produced from the vector, and those that enable replication of the vector and its packaging (e.g., into a viral particle). In some embodiments, the vector is a viral vector (i.e., a viral genome or a portion thereof). A vector may contain nucleic acid sequences or mutations, for example, that increase tropism and/or modulate immune function. An "expression cassette" comprises a coding sequence, operably linked to a promoter, and optionally a polyadenylation sequence.

The terms "polypeptide," "peptide," and "protein" are used interchangeably herein to refer to a polymer of amino acid residues. All three terms apply to amino acid polymers in which one or more amino acid residues are an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The terms "subject," "individual," and "patient" are used interchangeably herein to refer to a vertebrate, preferably a mammal, more preferably a human. Mammals include, but are not limited to, murines, mice, rats, simians, humans, farm animals, sport animals, and pets. Tissues, cells and their progeny of a biological entity obtained in vivo or cultured in vitro are also encompassed.

A "ligand" is a molecule that binds to and forms a complex with a biomolecule, e.g., a receptor protein, thereby altering the biomolecule's conformation and, as a result, its functional state. For the purposes of the present disclosure, a ligand is typically a polypeptide that is present within a larger conjugate polypeptide, together with an antigen. A ligand can be derived from a larger molecule, e.g., the ectodomain of a cell adhesion protein that interacts with another cell adhesion protein on the surface of immune cells. An example of a ligand for the purposes of the present disclosure is the first extracellular domain (or ectodomain) of CD58, referred to as 1dCD58, which can bind to CD2. For the purposes of the present disclosure, a ligand is not an antibody such as a monoclonal antibody.

As used herein, the term "administering" includes oral administration, topical contact, administration as a suppository, intravenous, intraperitoneal, intramuscular, intralesional, intratumoral, intrathecal, intranasal, intraosseous, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, intraosseous, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit and/or a prophylactic benefit. "Therapeutic benefit" means any therapeutically relevant improvement in or effect on one or more diseases, conditions, or symptoms under treatment. Therapeutic benefit can also mean to effect a cure of one or more diseases, conditions, or symptoms under treatment. Furthermore, therapeutic benefit can also mean to increase survival. For prophylactic benefit, the compositions may be administered to a subject at risk of developing a particular disease, condition, or symptom, or to a subject reporting one or more of the physiological symptoms of a disease, even though the disease, condition, or symptom may not yet be present.

The term "therapeutically effective amount" or "sufficient amount" refers to the amount of a system, recombinant polynucleotide, or composition described herein that is sufficient to effect beneficial or desired results. The therapeutically effective amount may vary depending upon one or more of: the subject and disease condition being treated, the weight and age of the subject, the severity of the disease condition, the immune status of the subject, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired therapeutic effect in a subject suffering from a disease such as an infectious disease or cancer. The desired therapeutic effect may include, for example, amelioration of undesired symptoms associated with the disease, prevention of the manifestation of such symptoms before they occur, slowing down the progression of symptoms associated with the disease, slowing down or limiting any irreversible damage caused by the disease, lessening the severity of or curing the disease, or improving the survival rate or providing more rapid recovery from the disease. Further, in the context of prophylactic treatment the amount may also be effective to prevent the development of the disease.

The term "pharmaceutically acceptable carrier" refers to a substance that aids the administration of an active agent to a cell, an organism, or a subject. "Pharmaceutically acceptable carrier" also refers to a carrier or excipient that can be included in the present compositions and that causes no significant adverse toxicological effect on the patient. Non-limiting examples of pharmaceutically acceptable carriers include water, sodium chloride (NaCl), normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also comprise or consist of substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor, etc. In some instances, the carrier is an agent that facilitates the delivery of a polypeptide, fusion protein, or polynucleotide to a target cell or tissue. One of skill in the art will recognize that other pharmaceutical carriers are also useful in the present methods and compositions.

The term "vaccine" refers to a biological composition that, when administered to a subject, has the ability to produce an acquired immunity to a particular pathogen or disease in the subject. Typically, one or more antigens, fragments of antigens, or polynucleotides encoding antigens or fragments of antigens that are associated with the pathogen or disease of interest are administered to the subject. Vaccines can comprise, for example, inactivated or attenuated organisms (e.g., bacteria or viruses), cells, proteins that are expressed from or on cells (e.g., cell surface or other proteins produced by cells (e.g., tumor cells)), proteins that are produced by organisms (e.g., toxins), or portions of organisms (e.g., viral envelope proteins or viral genes encoding various antigens). In some instances, cells are engineered to express proteins such that, when administered as a vaccine, they enhance the ability of a subject to acquire immunity to a particular cell type (e.g., enhance the ability of a subject to acquire immunity to a cancer cell) or to an organism that causes an infectious disease such as a virus, a bacterium, a fungal organism, a protozoan, or a helminth. As used herein, the term "vaccine" includes, but is not limited to, systems and recombinant polynucleotides of the present disclosure, as well as viral particles, host cells, and pharmaceutical compositions that comprise systems or recombinant polynucleotides as described herein.

The terms "Pac 1 site" and "Pac2 site" refer to cis-acting polynucleotide sequences in the direct terminal repeats of herpesvirus genomes, including cytomegalovirus genomes, that are recognized by the encapsidation machinery to initiate packaging and direct cleavage of genome concatemers into single, unit-length genomes (see, e.g., Fields Virology 6th edition, 2013, Knipe and Howley, eds.).

3. Vaccines

The present disclosure provides vaccines for generating an immune response against antigens from any type of pathogen. The antigen against which an immune response is generated (e.g., in a subject) will depend on the particular disease(s) for which prophylactic and/or therapeutic benefit is sought. In some embodiments, the antigen is an infectious disease antigen, such as a viral, bacterial, protozoal, helminthic, or fungal pathogen. In particular embodiments, the antigen is a viral antigen, e.g., from a coronavirus such as SARS-CoV-2. In some embodiments, the antigen is a tumor-associated antigen.

In some embodiments, an immune response (e.g., a desired, intended, or protective immune response, e.g., in a subject) is induced against a viral antigen (e.g., a viral infectious disease antigen). In some embodiments, an immune response is induced against a bacterial antigen (e.g., a bacterial infectious disease antigen). In some embodiments, an immune response is induced against a fungal antigen (e.g., a fungal infectious disease antigen). In some embodiments, an immune response is induced against a protozoal antigen (e.g., a protozoal infectious disease antigen). In some embodiments, an immune response is induced against a helminthic antigen (e.g., a helminthic infectious disease antigen). In some embodiments, an immune response is induced against a tumor-associated antigen. In some embodiments, the antigen is a bacterial, viral, fungal, protozoal, tumor-associated and/or helminthic antigen. In particular embodiments, the antigen is a viral antigen from a coronavirus, e.g., SARS-CoV-2.

The present vaccines can take on any of a number of forms, including through the administration of proteins, peptides, and nucleic acids including RNA or DNA encoding one or more antigens as described herein.

Immunogenic Conjugates

In particular embodiments, the vaccine comprises an "immunogenic conjugate" or "conjugate polypeptide" or "conjugate agent" comprising an antigen linked to a ligand or antibody fragment that binds to a surface protein present on an immune cell. For example, the antigen can be linked to an antibody fragment that specifically binds to a protein that is abundant on the surface of T cells. In some embodiments, the ligand is the ectodomain of a cell adhesion molecule. Any protein that is abundant on the surface of immune cells, including T cells such as helper T cells, can be targeted by the ligand or antibody fragment. In some embodiments, the protein bound by the ligand or antibody fragment is involved in signal transduction and/or adhesion. Examples of surface proteins that can be bound by the moiety include CD2 (see, e.g., NCBI Gene ID 914, or UNIProt P06729), CD3, including any CD3 subunit, i.e., CD3-epsilon (see, e.g., NCBI Gene ID 916, or UNIProt P07766), CD3-gamma (see, e.g., NCBI Gene ID 917, or UNIProt P09693, CD3-delta (see, e.g., NCBI Gene ID 915, or UNIProt P04234), or CD3-zeta (CD247; see, e.g., NCBI Gene ID 919, or UNIProt P20963), CD4 (see, e.g., NCBI Gene ID 920, or UNIProt P01730), and CD5 (see, e.g., NCBI Gene ID 921, or UNIProt P06217). Without being bound by the following theory, it is believed that, in some embodiments, such conjugate polypeptides can bridge B cells specific to the antigen with T cells, or other immune cells, in the vicinity of the B cells, and thereby elicit stronger antibodies than those obtained by vaccination using the antigen alone.

The antigen can be any immunogenic antigen from the pathogen, i.e., containing one or more epitopes that can stimulate a B-cell (antibody) or T-cell immune response and be specifically bound by antibodies and/or T cells in the subject. In particular embodiments, the antigen present within the immunogenic conjugate generates a robust antibody response in the subject. For example, for vaccination against a coronavirus such as SARS-CoV-2, the antigen can comprise a spike glycoprotein or a fragment thereof. In some such embodiments, the fragment comprises an S1 domain, a receptor-binding domain (RBD), or a fragment thereof (see, e.g., Ou et al., (2020) Nat. Commun. 11(1):1620; Walls et al. (2020) Cell 181(2):281-292; Lan et al. (2020) Nature doi: 10.1038/s41586-020-2180-5; Yuan et al. (2020) Science doi: 10.1126/science.abb7269; NCBI Accession Nos. QIG55857.1, 6VYB_C, 6VYB_B, 6VYB_A, or any of the SARS-CoV-2 spike glycoprotein entries in the NCBI database). In particular embodiments, the antigen comprises the SARS-CoV-2 RBD.

The antigen is linked to a ligand or antibody fragment that can bind to surface protein present on immune cells. In some embodiments, the surface protein is an abundant surface protein on T cells that is involved in signal transduction and/or adhesion. In some embodiments, the surface protein is present on a T cell or an antigen-presenting cell (APC). In some embodiments, the surface protein is preferentially expressed by T cells (e.g., relative to other immune cells). In some embodiments, the surface protein is substantially exclusively expressed by T cells (i.e., is expressed by T cells and not significantly expressed by other immune cells). In some embodiments, the ligand is a protein that naturally binds to a surface protein on immune cells, e.g., is the natural ligand for an immune cell receptor, or is a derivative or fragment of the natural ligand. In some embodiments, the ligand is the extracellular domain (ectodomain) or a cell adhesion molecule, e.g., CD58. For example, in some embodiments, the ligand is the 95 residue membrane-distal N-terminal domain of CD58 (1dCD58), which is entirely responsible for adhesion to CD2. For the purposes of the present disclosure, ligands do not include antibodies, e.g., monoclonal antibodies.

In some embodiments, the antibody fragment is a fragment of a monoclonal antibody. In some embodiments, the antibody fragment is a chimeric antibody fragment. In some embodiments, the antibody fragment is a humanized antibody fragment. In some embodiments, the antibody fragment is a human antibody fragment. In some embodiments, the antibody fragment is an antigen-binding fragment, such as a F(ab')2, Fab', Fab, scFv, and the like. The term "antibody fragment" can also encompass multi-specific and hybrid antibodies, with dual or multiple antigen or epitope specificities. In some embodiments, the antibody fragment is a nanobody, or single-domain antibody (sdAb), comprising a single monomeric variable antibody domain, e.g., a single VHH domain. In particular embodiments, the antibody fragment is an scFv, e.g., an anti-CD2, anti-CD3, or anti-CD4 scFv. For example, in some embodiments the fragment is an scFv derived from an anti-CD2 antibody such as LO-CD2a. In some embodiments the fragment is an scFv derived from an anti-CD3 antibody such as SP34. In some embodiments, the fragment is an scFv derived from an anti-CD4 antibody such as hu5A8. In some embodiments, the scFv is derived from a humanized antibody.

In some embodiments, e.g., where the antibody fragment is an scFv, the VH and VL domains of the antibody are separated by a flexible linker. In some embodiments, the flexible linker is 12 amino acids or longer, e.g., 15 amino acids in length. In such embodiments, the VH and VL domains are typically capable of folding properly, allowing the conjugate polypeptide to act as (e.g., bind to the surface protein) a monomer. In other embodiments, the flexible linker is less than 12 amino acids in length, e.g., 5, 6, 7, 8, 9, 10, or 11 amino acids in length. In such embodiments, the VH and VL regions can have insufficient length to fold properly as a monomer, promoting the formation of multimers, e.g., diabodies, triabodies, tetrabodies, etc. In some embodiments, the present disclosure comprises diabodies, triabodies, or tetrabodies formed between scFv antibody fragments as described herein. In some embodiments, such multimers are stabilized by disulfide bonds between monomer units.

For preparing an antibody fragment that binds to the surface protein, many techniques known in the art can be used. See, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2nd ed. 1986)). In some embodiments, antibodies are prepared by immunizing an animal or animals (such as mice, rabbits, or rats) with an antigen for the induction of an antibody response. For generating monoclonal antibodies, the B cells are fused with myeloma cells, which are subsequently screened for antigen specificity.

The genes encoding the heavy and light chains of an antibody of interest can be cloned from a cell, e.g., the genes encoding a monoclonal antibody can be cloned from a hybridoma and used to produce a recombinant monoclonal antibody, from which an antibody fragment can be generated. Gene libraries encoding heavy and light chains of monoclonal antibodies can also be made from hybridoma or plasma cells. Additionally, phage or yeast display technology can be used to identify antibodies and heteromeric Fab fragments that specifically bind to selected antigens (see, e.g., McCafferty et al., Nature 348:552-554 (1990); Marks et al., Biotechnology 10:779-783 (1992); Lou et al.m PEDS 23:311 (2010); and Chao et al., Nature Protocols, 1:755-768 (2006)). Alternatively, antibodies and antibody sequences may be isolated and/or identified using a yeast-based antibody presentation system, such as that disclosed in, e.g., Xu et al., Protein Eng Des Sel, 2013, 26:663-670; WO 2009/036379; WO 2010/105256; and WO 2012/009568. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can also be adapted to produce antibodies.

In some embodiments, antibody fragments (such as a Fab, a Fab', a F(ab')2, a scFv, nanobody, or a diabody) are generated. In a particular embodiment, the antibody fragment is an scFv (single-chain variable fragment). scFvs are recombinant polypeptides comprising the variable regions of light ($V_L$) and heavy ($V_H$) immunoglobulin chains. In some embodiments, the VH and VL sequences are joined by a flexible linker sequence. See, e.g., Nelson (2010) MAbs. 2(1):77-83. Various techniques have been developed for the production of antibody fragments, such as proteolytic digestion of intact antibodies (see, e.g., Morimoto et al., J. Biochem. Biophys. Meth., 24:107-117 (1992); and Brennan et al., Science, 229:81 (1985)) and the use of recombinant host cells to produce the fragments. For example, antibody fragments can be isolated from antibody phage libraries. Alternatively, Fab'-SH fragments can be directly recovered from E. coli cells and chemically coupled to form F(ab')2 fragments (see, e.g., Carter et al., BioTechnology, 10:163-167 (1992)). According to another approach, F(ab')2 fragments can be isolated directly from recombinant host cell culture. Other techniques for the production of antibody fragments will be apparent to those skilled in the art.

Methods for measuring binding affinity and binding kinetics are known in the art. These methods include, but are not limited to, solid-phase binding assays (e.g., ELISA assay), immunoprecipitation, surface plasmon resonance (e.g., Biacore™ (GE Healthcare, Piscataway, NJ)), kinetic exclusion assays (e.g., KinExA®), flow cytometry, fluorescence-activated cell sorting (FACS), BioLayer interferometry (e.g., Octet™ (FortéBio, Inc., Menlo Park, CA)), and western blot analysis.

In some embodiments, the affinity agent is a peptide, e.g, a peptide that binds to the T-cell surface protein. In some embodiments, the agent is a peptide aptamer. Peptide aptamers are artificial proteins that are selected or engineered to bind to specific target molecules. Typically, the peptides include one or more peptide loops of variable sequence displayed by the protein scaffold. Peptide aptamer selection can be made using different systems, including the yeast two-hybrid system. Peptide aptamers can also be selected from combinatorial peptide libraries constructed by phage display and other surface display technologies such as mRNA display, ribosome display, bacterial display and yeast display. See, e.g., Reverdatto et al., 2015, Curr. Top. Med. Chem. 15:1082-1101.

In some embodiments, the agent is an affimer. Affimers are small, highly stable proteins, typically having a molecular weight of about 12-14 kDa, that bind their target molecules with specificity and affinity similar to that of antibodies. Generally, an affimer displays two peptide loops and an N-terminal sequence that can be randomized to bind different target proteins with high affinity and specificity in a similar manner to monoclonal antibodies. Stabilization of the two peptide loops by the protein scaffold constrains the possible conformations that the peptides can take, which increases the binding affinity and specificity compared to libraries of free peptides. Affimers and methods of making affimers are described in the art. See, e.g., Tiede et al., eLife, 2017, 6:e24903. Affimers are also commercially available, e.g., from Avacta Life Sciences.

The antigen and ligand/antibody fragment can be directly or indirectly linked to one another in a number of ways. For example, in some embodiments, the antigen and ligand/antibody fragment are directly (covalently) linked, e.g., through a chemical linker or by virtue of being present in a single fusion protein. Methods for linking polypeptides to one another, e.g., for linking an antigen to a ligand/antibody fragment, are known and the art and are available from commercial suppliers, e.g., a protein-protein conjugation kit from TriLink BioTechnologies, from Vector Laboratories, from Kerafast, from SydLabs, from INTERCHIM, or others.

In particular embodiments, an antigen and a ligand/antibody fragment are present within a single fusion protein. For example, in particular embodiments, the immunogenic conjugate is a fusion protein that comprises an antigen and an anti-CD3 scFv antibody fragment. In some embodiments, the fusion protein also comprises a flexible linker separating the antigen and scFv sequence. The fusion protein can be expressed in vitro, purified, formulated, and administered in protein form using standard molecular biology and pharmaceutical methods, or can be administered as a polynucleotide encoding the fusion protein, as described in more detail elsewhere herein.

In some embodiments, in particular when the fusion protein is administered via administration of a polynucleotide encoding the fusion protein, the fusion protein comprises a tPA leader sequence, e.g., a tPA leader sequence of 23 amino acids in length (see, e.g., UniProt P00750; Kou et al. (2017) Immunol. Lett. 190:51-57; Wang et al. (2011) Appl. Microbiol. Biotech. 91(3):731-740; Delogu et al. (2002) Microbial Immun. Vacc. Doi: 10.1128/IAI.70.1.292-

302.2002). In some such embodiments, the tPA leader sequence comprises a 22P/A enhancing mutation (see, e.g., Wang et al. (2011).

In some embodiments, the antigen and the ligand/antibody fragment present within a conjugate polypeptide or fusion protein are separated by a flexible linker. Suitable linkers for separating protein domains are known in the art, and can comprise, e.g., glycine and serine residues, e.g., from 2-20 glycine and/or serine residues. In one embodiment, the flexible linker comprises a $(Gly_4Ser)_n$ flexible peptide linker, e.g., a $(Gly_4Ser)_3$ linker comprising the sequence

GGGGSGGGGSGGGGS. (SEQ ID NO: 5)

In some embodiments, the conjugate polypeptide comprises a domain such as a lipid anchor, a transmembrane segment, a multimerizing domain, or a combination of two or more of these domains. Examples of lipid anchors include, e.g., glycosylphosphatidylinositol anchors. In some embodiments, the addition of a lipid anchor such as a glycosylphosphatidylinositol anchor is directed by a signal sequence, such as a signal sequence derived from CD55. Examples of suitable transmembrane segments include, but are not limited to, transmembrane segments derived from a PDGF receptor, glycophorin A, or the SARS-CoV-2 spike protein. Examples of multimerization domains include, e.g., domains derived from T4 fibritin and Fc domains, e.g., a human IgG Fc domain. In some embodiments, the present disclosure comprises dimers or other multimers formed between the present conjugate polypeptides comprising multimerizing, e.g., T4 fibritin or Fc domains. In some embodiments, multimers are stabilized by disulfide bonds between monomer units. In some embodiments, an Fc or other domain is located at the C-terminus of the conjugate polypeptide.

In some embodiments where the vaccine comprises polynucleotides encoding a fusion protein, and wherein the polynucleotide is present within a viral vector such as a CMV vector, the coding sequence for the fusion protein is operably linked to a late promoter, e.g., a CMV pp65b promoter. Without being bound by the following theory, it is believed that expressing an antigen, e.g., an immunogenic conjugate, via a powerful late promoter such as pp65b, elicits robust antibody responses but only weak T-cell responses.

In some embodiments, the antigen and ligand/antibody fragment (also referred to as an "affinity agent") are indirectly linked, i.e., linked through non-covalent interactions that bridge the two entities. For example, the antigen and ligand/antibody fragment can be linked through a second, "bridging" antibody or fragment thereof. In some embodiments, the antigen is a membrane protein that is embedded in a nanodisc, and the bridging antibody is a bispecific antibody fragment that binds both to (i) either the antigen itself or to a membrane scaffolding protein within the nanodisc, and (ii) the T cell surface protein. Nanodiscs are synthetic membrane systems comprising a lipid bilayer that is surrounded by amphipathic proteins called membrane scaffolding proteins (MSPs). Any nanodisc system can be used in the present methods, including any MSPs such as apoA1-derived MSPs or amphipathic peptides. In some embodiments, synthetic nanodiscs are used. The preparation and use of nanodiscs is known in the art and is described, e.g., in Bayburt et al. (2002) FEBS Letters 584(9):1721-1727; Denisov et al. (2004) J. Am. Chem. Soc. 126(11): 3477-3487; Grinkova et al. (2010) PEDS 23(11):843-848; Midtgaard et al. (2016) Soft Matter 10(5): 738-752; Larsen et al. (2016) Soft Matter 12(27): 5937-5949; Kondo et al. (2016) Colloids and Surfaces B: Biointerfaces 146:423-430; Knowles et al. (2009) J. Am. Chem. Soc. 131(22):7484-7485; Oluwole et al. (2017) 33(50):14378-14388; Rouck et al. (2017) FEBS Lett. 591(14):2057-2088; Denisov & Sligar (2016) Nat. Struct. Mol. Biol. 23(6):481-486; the entire disclosures of each of which are herein incorporated by reference.

In some embodiments, the conjugate polypeptide comprises an amino acid sequence as shown in SEQ ID NO:1, SEQ ID NO:6, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, or SEQ ID NO:27, or an amino acid sequence comprising at least about 70%, 75%, 80%, 85%, 90%, 95%, 96%, 97%, 98%, 99%, or more identity to SEQ ID NO:1, SEQ ID NO:6, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, or SEQ ID NO:27.

Additional Antigens

In some embodiments, the vaccines comprise a second antigen, which can be present together with or in the place of the immunogenic conjugate. When both antigens are present (i.e., the immunogenic conjugate and the second antigen), the antigens can be administered together, i.e., within the same vaccine, or independently, e.g., formulated separately and administered at the same time, e.g., during a single clinical visit, or at different times, e.g., on different days. One or both antigens can be administered in protein form or in polynucleotide form (i.e., as polynucleotides encoding the two antigens). In some embodiments, when administered in polynucleotide form, the coding sequence for the immunogenic conjugate and the coding sequence for the second antibody are present within a single vector, each of them being operably linked to a promoter. In some embodiments, the second antigen is administered as a polynucleotide encoding the antigen, operably linked to a constitutive promoter, e.g., a mammalian promoter such as EF-1 alpha (see, e.g., Wang et al. (2017) J. Cell Mol. Med 21(11):3044-3054; Edmonds et al. (1996) J. Cell Sci. 109 (11):2705-2714; NCBI Gen ID 1915; the entire disclosures of which are herein incorporated by reference). Without being bound by the following theory, it is believed that expressing the second antigen in the cytoplasmic compartment of the cell elicits a robust T-cell response, but with minimal accompanying antibody responses.

In some embodiments, when the pathogen is a coronavirus such as SARS-CoV-2, the second antigen comprises an E (envelope protein, see, e.g., NCBI Gene ID 43740570), M (membrane glycoprotein, see, e.g., NCBI Gene ID 43740571), or N (nucleocapsid phosphoprotein, see, e.g., NCBI Gene ID 43740575), or a fragment thereof. In some embodiments, the second antigen comprises a fusion protein comprising the E and M proteins of a coronavirus such as SARS-CoV-2, or a fragments of the E and/or M proteins. Other suitable SARS-CoV-2 antigens include nsp3, nsp4, or nsp6, or fragments thereof. In particular embodiments, the vaccine comprises codon-optimized coding sequences for the N protein and/or the fusion protein comprising the E and M proteins of SARS-CoV-2 (e.g., as shown in SEQ ID NOS: 3 and 4).

Nucleic Acid Vaccines

In some embodiments, nucleic acid vaccines, e.g., DNA vaccines, are used to introduce the immunogenic conjugate and/or second antigen. Accordingly, in some embodiments, the present disclosure provides polynucleotides encoding any of the herein-described conjugate polypeptides. In some embodiments, the DNA vaccines are prepared as DNA vectors or plasmids. In some embodiments, the DNA vaccines are prepared as recombinant viruses, e.g., by modifying a parent virus to incorporate exogenous genetic material, e.g., one or more polynucleotides encoding one or more antigens as described herein. A non-limiting list of suitable viruses that can be used for the purposes of the present disclosure include lentiviruses, (e.g., HIV, HIV-1, HIV-2, FIV, BIV, EIAV, MW, CAEV, SIV), adenoviruses and adeno-associated viruses, alphaviruses, herpesviruses (e.g., cytomegalovirus), flaviviruses, and poxviruses. For methods and examples concerning the use of suitable viral vectors, see, e.g., U.S. Pat. Nos. 5,219,740, 7,250,299, 7,608,273, 6,465,634, 7,811,812, 5,744,140, 8,124,398, 5,173,414, 7,022,519, 7,125,705, 6,905,862, 7,989,425, 6,468,711, 7,015,024, 7,338,662, 5,871,742, and 6,340,462. In such embodiments, the viruses are typically recombination-competent (i.e., capable of reproducing in an infected host cell). Modification of such viruses and vectors or plasmids for the preparation of the present DNA vaccines can be achieved using standard molecular biology techniques, e.g., as taught in Sambrook et al. (1989) "Molecular Cloning: A Laboratory Manual" ($2^{nd}$ ed. Cold Spring Harbor Press) and Ausubel et al. (Eds.) (2000-2010) "Current Protocols in Molecular Biology" (John Wiley and Sons).

In some embodiments, the polynucleotides encode an amino acid sequence as shown in SEQ ID NO:1, SEQ ID NO:6, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, or SEQ ID NO:27, or an amino acid sequence comprising at least about 70%, 75%, 80%, 85%, 90%, 95%, 96%, 97%, 98%, 99%, or more identity to SEQ ID NO:1, SEQ ID NO:6, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, or SEQ ID NO:27. In some embodiments, the polynucleotides comprise a nucleotide sequence as shown in SEQ ID NO:2, SEQ ID NO:7, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO: 26, or SEQ ID NO:28, or nucleotide sequence comprising at least about 70%, 75%, 80%, 85%, 90%, 95%, 96%, 97%, 98%, 99%, or more identity to SEQ ID NO:2, SEQ ID NO:7, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO: 26, or SEQ ID NO:28.

In particular embodiments, the DNA vaccines involve cytomegalovirus (CMV) vectors, e.g. self-launching CMV DNA vectors ($_{SL}$CMV) as described in, e.g., U.S. Provisional Application No. 62/842,419, filed on May 2, 2019, the entire disclosure of which is herein incorporated by reference. Self-launching CMV vaccines are administered as CMV genomes that "launch" vectored vaccine replication in vivo, resulting in strong immune responses having the unique character associated with CMV infection. $_{SL}$CMV vectors can comprise one or more of numerous features, including: (i) being based on the Towne HCMV strain, which has been proven safe for use in humans of all ages; (ii) providing immune responses in CMV-seropositive and -seronegative individuals due to CMV capacity for superinfection and proprietary deletions to the CMV genome; (iii) providing T-cell responses of extraordinary breadth and intensity that "paint" the vaccine antigen; (iv) having a proven capacity to elicit balanced responses including antibodies, CD4$^+$ T cells, and CD8$^+$ T cells—without reliance on or dominance of any single effector response; providing localization of responding T cells to mucosal surfaces due to effector-memory phenotype; (v) allowing engineering of new vaccine candidates in weeks to months; and (vi) providing a single manufacturing process based on plasmid production in E. coli.

In contrast to most vaccine types, which do not elicit large numbers of memory CD4$^+$ T cells, the present CMV-vectored vaccines do, as shown in the Examples below. Further, T cells responding to CMV-vectored vaccines localize to airways among other effector sites and can be recovered, e.g., by bronchoalveolar lavage (12). CMV-responsive T cells recapitulate other essential features of cells shown to be protective against SARS-CoV-1, including CXCR3 expression, IFN-γ production, and IL-10 production (13).

In $_{SL}$CMV vectors, utilizing a CMV vector in its DNA form for vaccination requires an alteration in the current CMV BAC construct, so that the BAC backbone can be excised without recombinase or nuclease expression in vivo. CMV has a relatively strict packaging limit due to the need to package unit-length genomes into an icosahedral capsid. In some embodiments, the CMV BAC utilizes an endogenous recombinase gene placed within the BAC portion of the DNA construct. Upon transfection of mammalian cells, the recombinase is expressed and excises the BAC replication machinery from the replicating genomes. To make a BAC DNA vector suitable for in vivo delivery in humans, the CMV genome termini are re-organized to enable excision of the BAC without the requirement for expression of a recombinase. In particular, the reconfigured BAC constructs utilize the viral terminase complex to eliminate the bacterial origin of replication during the packaging step of CMV replication. In some embodiments, the location of the BAC origin and replication machinery is located between the viral direct repeats.

Accordingly, in one embodiment, the disclosure provides a self-launching HV (e.g., CMV) recombinant polynucleotide comprising one or more polynucleotides encoding one or more antigens (or conjugate polypeptides) as described herein, and including (a) a herpesvirus (HV) genome or a substantial portion thereof; (b) a sequence comprising an origin of replication that functions in a single-celled organism; (c) one or more terminase complex recognition loci (TCRL) comprising a recombinantly introduced polynucleotide sequence that can direct cleavage by an HV terminase complex; wherein the HV genome or portion thereof is separated from the sequence comprising an origin of replication by a TCRL; wherein the HV genome or portion thereof abuts a TCRL at at least one extremity; and wherein the sequence comprising the origin of replication abuts a TCRL at at least one extremity; and (d) one or more polynucleotides encoding one or more antigens, operably linked to a promoter. In one embodiment, the recombinant polynucleotide comprises a polynucleotide encoding an immunogenic conjugate (e.g., an antigen fused to a polypeptide that specifically binds to an abundant T-cell surface protein), operably linked to a late promoter such as pp65b, and/or a polynucleotide encoding an antigen, operably linked to a constitutive promoter such as EF-1 alpha.

As used herein, the "extremity" of a specific genomic region or element in a vector, such as a genome or portion thereof, refers to either end of the region or element, beyond which a different region or element (or the end of the nucleic acid molecule) is present. For example, in a circular vector, in some embodiments, one end (or extremity) of the HV genome can be directly adjacent to a first end of a first TCRL element, and the other end (or extremity) of the HV genome can be directly adjacent to a first end of a second TCRL element. In the same circular vector, one end (or extremity) of the origin-containing region can be directly adjacent to a second end of the first TCRL element, and the other end (or extremity) of the origin-containing region can be directly adjacent to a second end of the second TCRL element. In some embodiments, the CMV vectors as used herein do not comprise a viral IL-10 gene.

It will be appreciated that the polynucleotides can be circular or linear, and that additional elements can be present, e.g., present between an HV genome or substantial portion thereof and a sequence comprising a BAC or YAC origin of replication, e.g., genetic elements present between a TCRL abutting an HV genome or substantial portion thereof and a (BAC or YAC) origin of replication that functions in a single-celled organism.

Antigen Coding Sequences

The recombinant polynucleotides of the disclosure, e.g., viral vectors, comprise nucleic acid sequences encoding antigens, e.g., a conjugate polypeptide as described herein, and/or a coronavirus antigen such as the spike protein, E, M, or N proteins, or combinations and/or fragments thereof, as described herein. Rapid progress in the studies of various genomes has made possible a cloning approach where a human or other model organism DNA sequence database can be searched for any gene segment that has a certain percentage of sequence homology to a known nucleotide sequence, such as one encoding an antigen, etc. Any DNA sequence so identified can be subsequently obtained by chemical synthesis and/or a polymerase chain reaction (PCR) technique such as the overlap extension method. For a short sequence, completely de novo synthesis may be sufficient; whereas further isolation of full length coding sequence from a human or other model organism cDNA or genomic library using a synthetic probe may be necessary to obtain a larger gene.

Alternatively, a nucleic acid sequence can be isolated from a cDNA or genomic DNA library (e.g., human or rodent cDNA or human, rodent, bacterial, or viral genomic DNA library) using standard cloning techniques such as polymerase chain reaction (PCR), where homology-based primers can often be derived from a known nucleic acid sequence. Commonly used techniques for this purpose are described in standard texts, e.g., Sambrook and Russell, supra.

cDNA libraries may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene*, 25: 263-269 (1983); Ausubel et al., supra). Upon obtaining an amplified segment of nucleotide sequence by PCR, the segment can be further used as a probe to isolate the full-length polynucleotide sequence encoding the protein of interest from the cDNA library. A general description of appropriate procedures can be found in Sambrook and Russell, supra.

A similar procedure can be followed to obtain a full-length sequence encoding a protein of interest from a human or other model organism genomic library. Genomic libraries are commercially available or can be constructed according to various art-recognized methods. As a non-limiting example, to construct a genomic library, the DNA is first extracted from a tissue of the organism. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage vectors. These vectors and phages are packaged in vitro. Recombinant phages are analyzed by plaque hybridization as described in Benton and Davis, *Science*, 196: 180-182 (1977). Colony hybridization is carried out as described by Grunstein et al., *Proc. Natl. Acad. Sci. USA*, 72: 3961-3965 (1975).

In particular embodiments, polynucleotides encoding the antigens (e.g., immunogenic conjugates and/or other antigens) are present within expression cassettes, i.e., are operably linked to one or more promoters. Any promoter capable of driving expression of the polynucleotides in one or more cells of a subject can be used, including inducible and constitutive promoters. In some embodiments, a CMV promoter is used. In particular embodiments, a late viral promoter such as pp65b is used to drive the expression of the immunogenic conjugate. In particular embodiments, a constitutive mammalian promoter such as EF1-alpha is used to drive the expression of the second antigen as described herein. In some embodiments, the EF1-alpha promoter includes the first intron of the EF1-alpha gene. The vectors can comprise other regulatory sequences, e.g., terminators, translational regulatory sequences such as ribosome binding sites and internal ribosome entry sites, enhancers, silencers, insulators, boundary elements, replication origins, matrix attachment sites and locus control regions, etc. The use of such elements are well known in the art.

In some embodiments, a recombinant polynucleotide of the present disclosure contains a nucleic acid sequence that encodes a selectable marker. A selectable marker is useful, for example, when a polynucleotide as described herein is being recombinantly modified, especially when it is desirable to screen a population of modified polynucleotides (e.g., using bacterial, yeast, plant, or animal cells) for those that have incorporated the desired modification(s). Whether the polynucleotide is recombinantly modified within a cell (e.g., a bacterial cell, for example, using Red/ET recombination) or is recombinantly modified and subsequently introduced into a cell (e.g., bacterial, yeast, plant, or animal cell) for screening, the selectable marker can be used to identify which cells contain polynucleotides that have incorporated a modification of interest. Taking antibiotic resistance genes as an example of a selectable marker, treating the cells that contain the recombinant polynucleotides with the antibiotic will identify which cells contain recombinant polynucleotides that have incorporated the antibiotic resistance gene (i.e., the cells that survive after antibiotic treatment must have incorporated the antibiotic resistance gene). If desired, the recombinant polynucleotides can be further screened (e.g., purified from the cells, amplified, and sequenced), in order to verify that the desired modification has been recombinantly introduced into the polynucleotide at the correct position.

When the selectable marker is an antibiotic resistance gene, the gene can confer resistance to chloramphenicol, Zeocin, ampicillin, kanamycin, tetracycline, or another appropriate antibiotic that will be known to one of skill in the art. In some embodiments, a selectable marker is used that produces a visible phenotype, such as the color of an organism or population of organisms. As a non-limiting example, the phenotype can be examined by growing the organisms (e.g., cells or other organisms that contain the recombinant polynucleotide) and/or their progeny under conditions that result in a phenotype, wherein the phenotype may not be visible under ordinary growth conditions.

In some embodiments, the selectable marker used for identifying cells that contain a polynucleotide containing a modification of interest is a fluorescently tagged protein, a chemical stain, a chemical indicator, or a combination thereof. In other embodiments, the selectable marker responds to a stimulus, a biochemical, or a change in environmental conditions. In some instances, the selectable marker responds to the concentration of a metabolic product, a protein product, a drug, a cellular phenotype of interest, a cellular product of interest, or a combination thereof.

The size of a recombinant polynucleotide will depend on the particular antigen(s) and other proteins that are being encoded, the presence and choice of regulatory sequences and/or expression vectors (e.g., viral vectors), the choice and position of different elements such as TCRLs, etc. Additionally, the size of a recombinant polynucleotide will depend on whether the nucleic acid sequences encoding the antigen and other proteins are present within the same recombinant polynucleotide or separate recombinant polynucleotides.

In some embodiments, a recombinant polynucleotide is between about 1 kilobase and about 300 kilobases (e.g., about 1, 1.1, 1.2, 1.3, 1.4, 1.5, 1.6, 1.7. 1.8, 1.9, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 kilobases) in length. In some embodiments, the recombinant polynucleotide is greater than about 300 kilobases in length.

In some embodiments, a recombinant polynucleotide present in a system of the present disclosure is about 1 kilobase to about 300 kilobases, about 1 kilobase to about 250 kilobases, about 1 kilobase to about 200 kilobases, about 1 kilobase to about 150 kilobases, about 1 kilobase to about 100 kilobases, about 1 kilobase to about 50 kilobases, about 1 kilobase to about 40 kilobases, about 1 kilobase to about 30 kilobases, about 1 kilobase to about 20 kilobases, about 1 kilobase to about 10 kilobases, about 50 kilobases to about 300 kilobases, about 50 kilobases to about 250 kilobases, about 50 kilobases to about 200 kilobases, about 50 kilobases to about 150 kilobases, about 50 kilobases to about 100 kilobases, about 100 kilobases to about 300 kilobases, about 100 kilobases to about 250 kilobases, about 100 kilobases to about 200 kilobases, about 100 kilobases to about 150 kilobases, about 150 kilobases to about 300 kilobases, about 150 kilobases to about 250 kilobases, about 150 kilobases to about 200 kilobases, about 200 kilobases to about 300 kilobases, or about 200 kilobases to about 250 kilobases in length.

General Recombinant Technology

Basic texts disclosing general methods and techniques in the field of recombinant genetics, e.g., for the preparation, maintenance, and culture of recombinant vectors or plasmids, include Sambrook and Russell, *Molecular Cloning, A Laboratory Manual* (3rd ed. 2001); Kriegler, Gene *Transfer and Expression: A Laboratory Manual* (1990); and Ausubel et al., eds., *Current Protocols in Molecular Biology* (1994).

For nucleic acids, sizes are given in either kilobases (kb) or base pairs (bp). In some instances, these are estimates derived from agarose or acrylamide gel electrophoresis, from sequenced nucleic acids, or from published DNA sequences. For proteins, sizes are given in kilodaltons (kDa) or amino acid residue numbers. In some instances, protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a protein domain or gene of interest can be verified after cloning or subcloning using, e.g., the chain termination method for sequencing double-stranded templates of Wallace et al., *Gene* 16: 21-26 (1981).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, PCR Technology, CRC Press Inc. 1994) to amplify a segment of nucleotide sequence from a cDNA or genomic library. Using the amplified segment as a probe, the full-length nucleic acid encoding a protein of interest is obtained.

Upon acquiring a nucleic acid sequence encoding a protein of interest, the coding sequence can be further modified by a number of well-known techniques such as restriction endonuclease digestion, PCR, and PCR-related methods to generate coding sequences, including mutants and variants derived from the wild-type protein. The polynucleotide sequence encoding the desired polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding a protein of interest. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

Codon Optimization

In some embodiments, a nucleic acid sequence encoding a protein of interest (e.g., an antigen or other protein) is codon optimized. The term "codon optimization" refers to altering a nucleic acid sequence, without changing the encoded amino acid sequence, in such a way that codon bias (i.e., the preferential use of particular codons that can vary between species) is reduced or rebalanced. In some embodiments, codon optimization increases translational efficiency (e.g., of an antigen or other protein). As a non-limiting example, leucine is encoded by six different codons, some of which are rarely used. By rebalancing codon usage (e.g., within a reading frame), preferred leucine codons can be selected over rarely used codons. The nucleic acid sequence encoding the protein (e.g., antigen or other protein) of interest is altered such that the rarely used codons are converted to preferred codons.

Rare codons can be defined, for example, by using a codon usage table derived from the sequenced genome of a host species, i.e., the species in which the protein (e.g., an antigen) will be expressed. See, e.g., the codon usage table obtained from Kazusa DNA Research Institute, Japan (www.kazusa.or.jp/codon/) used in conjunction with software, e.g., "Gene Designer 2.0" software, from DNA 2.0 (www.dna20.com/) at a cut-off threshold of 15%.

Codon optimization may also be employed to modulate GC content, e.g., to increase mRNA stability or reduce secondary structure; or otherwise minimize codons that may result in stretches of sequence that impair expression of the protein of interest (e.g., an antigen or other protein).

4. Formulation and Vaccination Methods

Subjects

The present methods and compositions can be used for the vaccination of any subject, e.g., a human or other mammal, that could benefit from an enhanced immune response against infection, e.g., infection by a coronavirus such as SARS-CoV-2. In some embodiments, the subject is male. In some embodiments, the subject is female. In some embodiments, the subject is an adult (e.g., an adult male). In some embodiments, the subject is an adolescent. In some embodiments, the subject is a child. In some embodiments, the subject is above 60, 70, or 80 years of age.

In some embodiments, the subject has not been infected with the pathogen, e.g., SARS-CoV-2, and the methods and compositions are used to enhance the subject's immune defenses against the pathogen in order to prevent future infection. In other embodiments, the subject is already infected with the pathogen, and the methods are used to enhance the subject's immune response against the pathogen in order to slow or potentially reverse the original infection.

Pharmaceutical Compositions

The present disclosure provides compositions comprising an immunogenic component (e.g., a DNA vaccine or one or more immunogenic polypeptides) capable of inducing immunity against a targeted agent (e.g., antigen or immunogenic conjugate comprising an antigen), and a pharmaceutically acceptable carrier. In some embodiments, the vaccines further comprise one or more adjuvants or compounds. As such, the present disclosure provides pharmaceutical compositions for inducing an immune response in a subject. In some embodiments, the composition comprises one or more polynucleotides encoding one or more proteins, e.g., a coronavirus antigen and/or immunogenic conjugate, and a pharmaceutically acceptable carrier. In some embodiments, the composition comprises one or more polypeptide antigens, e.g., an immunogenic conjugate as described herein, and/or a coronavirus antigen comprising, e.g., a spike protein, E, M, or N protein, a fragment thereof, or a combination thereof, and a pharmaceutically acceptable carrier. In some embodiments, the composition further comprises an adjuvant.

The compositions may be formulated for, e.g., injection, inhalation, or topical administration, e.g., facilitating direct exposure of host cells and tissues to the immunogenic component. In some embodiments, the compositions, e.g., DNA vaccines, are formulated for subcutaneous injection. In some embodiments, the compositions, e.g., DNA vaccine, are formulated as naked DNA (see, e.g., U.S. Pat. Nos. 6,265,387, 6,972,013, and 7,922,709).

In particular embodiments, the DNA vaccines are prepared as DNA vectors or plasmids. In some embodiments, the compositions, e.g., DNA vaccine, are prepared as recombinant viruses, e.g., by modifying a parent virus to incorporate exogenous genetic material, e.g., one or more polynucleotides encoding one or more antigens as described herein. In some embodiments, the virus is a herpesvirus such as CMV, an adenovirus, or an adeno-associated virus (AAV). Self-launching CMV ($_{SL}$CMV) vectors can be prepared, e.g., by culturing *E. coli* comprising the vector, lysing the cultured bacterial cells, purifying the vector while ensuring that endotoxins are absent or below the pyrogenic threshold (e.g., 5 endotoxin units/kg body weight), and formulating the vector for administration. In some embodiments, proteins encoding the present antigens are produced in vitro using standard molecular biology techniques and are purified prior to vaccine formulation as described herein.

In some embodiments, a nucleic acid vaccine is formulated with an in vivo transfection agent, e.g. comprising one or more reagents that can protect the nucleic acid from degradation in vivo and facilitate delivery of the nucleic acid to cells. Suitable examples of such agents include, but are not limited to, in vivo-jetPEI™ (Polyplus), TurboFed™ (Thermo Scientific), LIPID™ (Altogen Biosystems), GenJet™ Plus or PepJet™ Plus (SignaGen), DogtorMag™ (OZ Biosciences), Avalanche™ (EZ Biosystems), and others, and can be used according to the manufacturers' instructions.

The pharmaceutical compositions of the disclosure may comprise a pharmaceutically acceptable carrier. In certain aspects, pharmaceutically acceptable carriers are determined in part by the particular composition being administered, as well as by the particular method used to administer the composition. Accordingly, there is a wide variety of formulations of pharmaceutical compositions that are suitable for use in the present methods and compositions (see, e.g., REMINGTON'S PHARMACEUTICAL SCIENCES, 18TH ED., Mack Publishing Co., Easton, PA (1990)).

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

The pharmaceutical compositions are administered in a manner compatible with the dosage formulation, and in such amount as will be therapeutically or prophylactically effective. The quantity to be administered depends on a variety of factors including, e.g., the age, body weight, physical activity, hereditary characteristics, general health, sex, and diet of the individual, the condition or disease to be treated or prevented, and the stage or severity of the condition or disease. In certain embodiments, the size of the dose may also be determined by the existence, nature, and extent of any adverse side effects that accompany the administration of a therapeutic or prophylactic agent(s) in a particular individual. Other factors that can influence the specific dose level and frequency of dosage for any particular patient include the activity of the specific compound employed, the metabolic stability and length of action of that compound, the mode and time of administration, and the rate of excretion.

In some embodiments, the vaccines comprise an adjuvant, i.e., a compound administered to a subject in conjunction with an antigen for enhancing an immune response to the antigen. Adjuvants can increase the immunogenicity of vaccines in any of a number of ways, and can include inorganic compounds such as salts, e.g., aluminum salts, as well as organic compounds and mixtures of compounds, including extracts and preparations, e.g., Freund's incomplete adjuvant, squalene, MF59, monophosphoryl lipid A, QS-21.

Generally, for administering the compound (e.g., vaccine or adjuvant) for therapeutic or prophylactic (e.g. vaccination) purposes, the compound is given at a therapeutically or prophylactically effective dose. In particular, an effective amount of a pharmaceutical composition is an amount that is sufficient to obtain an enhanced immune response against the antigen or pathogen from which the antigen is derived, e.g., in view of any of the parameters or indices described herein, and/or a sufficient amount to enhance the immunity of a subject to infection from the pathogen or to the propagation of an already-existing infection in the subject.

In certain embodiments, the dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for humans and other mammals (e.g., an ampoule), each unit containing a predetermined quantity of a therapeutic or prophylactic agent calculated to produce the desired onset, tolerability, and/or therapeutic or prophylactic effects, in association with a suitable pharmaceutical excipient. In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the therapeutic or prophylactic compound.

Methods for preparing such dosage forms are known to those skilled in the art (see, e.g., REMINGTON'S PHARMACEUTICAL SCIENCES, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Administration

In some embodiments, prevention and/or treatment includes administering compositions as described herein directly to a subject. As a non-limiting example, pharmaceutical compositions (e.g., comprising a vaccine as described herein and a pharmaceutically acceptable carrier) can be delivered directly to a subject (e.g., by local injection or systemic administration).

Compositions of the present disclosure may be administered as a single dose or as multiple doses, for example two doses administered at an interval of about one month, about two months, about three months, about six months, or about 12 months. Other suitable dosage schedules can be determined by a medical practitioner.

In some embodiments, additional compounds or medications can be co-administered to the subject. Such compounds or medications can be co-administered for the purpose of alleviating signs or symptoms of the disease being treated, reducing side effects caused by induction of the immune response, etc.

The present pharmaceutical compositions can be administered locally or systemically to the subject, e.g., intraperitoneally, intramuscularly, intra-arterially, orally, intravenously, intracranially, intrathecally, intraspinally, intralesionally, intranasally, subcutaneously, intracerebroventricularly, topically, and/or by inhalation. In particular embodiments, the compositions are administered by electroporation (e.g., for the priming DNA vaccine) or subcutaneously (e.g., for the boost).

The present vaccines can be administered any of a number of times, e.g., 1, 2, 3, 4, 5 or more times, and following any of a number of vaccination regimens, e.g., every 1, 2, 3, 4, 5, 6, 7, 8, 9, 10 or more weeks. In a particular embodiment, the vaccine is administered as a DNA prime, e.g., with a plasmid encoding a conjugate polypeptide as described herein, which is followed by a boost, e.g., after about 4 weeks, e.g., with an adenoviral vector encoding an antigen. DNA vaccines can be administered at any of a number of levels, e.g., 4 mg of plasmid DNA vector per subject per vaccination, or 1, 2, 3, 4, 5, 6, 7, 8, 9, 10 or more mg of plasmid DNA vector per subject per vaccination, or 1-10, 1-20, 1-8, 1-7, 2-6, 3-5 mg or plasmid DNA vector per subject per vaccination.

Assessing Immune Responses

The immune response of the subject receiving a vaccine of the disclosure can be detected, characterized, or quantified in any of a number of ways. For example, any of the assays described in any of the Examples to detect the presence of a polynucleotide of the disclosure in cells of the subject can be detected, to detect and characterize antibodies or T-cells specific to the present vaccines, or to assess the protection afforded by the vaccine against infection by a pathogen, can be used. In some embodiments, particularly in embodiments where a nucleic acid vector is used to deliver the present antigens, the presence and level of vector sequences can be assessed, e.g., by measuring sequences using qPCR from, e.g., blood or saliva samples from a subject. The levels of the nucleic acids can also be detected from different tissues of the subject, e.g., as obtained from a biopsy or by lavage of mucosal tissues.

In some embodiments, the immune response of a subject is assessed by immunophenotyping, e.g., by assessing T-cell memory-effector subsets, NK cells with adaptive characteristics (e.g., FcεRIy$^{low}$ "memory" NK cells), T cells with innate characteristics (e.g., NKG2A⁺ cells), or antigen-presenting cells (e.g., monocytes expressing CD80/83/86). Such cells can be assessed, e.g., using flow cytometry as described in the Examples.

The immune response of a subject can also be assessed by characterizing antigen-specific T-cell responses from the subject. For example, PBMC or LNMC cells can be stimulated with one or more antigens from the vaccine, optionally in conjunction with inhibitors such as VL9 peptide or anti-HLA antibodies, as described in the Examples. After a suitable amount of time, e.g., 16 hours, the cells can be assessed using antibodies to, e.g., CD3, CD4, CD8, CCR7, CD95, IL-2, IL-17, IFN-γ, and/or TNF-α. Cytokine-secreting CD4⁺ and/or CD8⁺ cells can be assessed using, e.g., flow cytometry.

In some embodiments, antibodies obtained from the subject can be assessed, e.g., by detecting binding to antigens using ELISA. In some embodiments, neutralizing or enhancing antibodies are tested using a RVP (reporter virus particle) assay. In particular embodiments, the present vaccines elicit strong neutralizing antibody responses and low or absent enhancing responses. In some embodiments, e.g., where vaccination strategies are tested in model animals, a challenge assay using the pathogen can be used, as described in the Examples.

Any of parameters or effects described in the Examples or elsewhere herein (e.g., neutralizing antibody production, specific T cell responses, protection against a pathogen, etc.), can be used to assess the efficacy of a vaccine as described herein. In some embodiments, a vaccine of the disclosure leads to an increase of at least about 20%, 25%, 30%, 40%, 50%, 60%, 70%, 75%, 80%, 90%, 100%, 150%, 200%, 250%, 300%, or more in any of the herein-described parameters or effects relative to a control value (e.g., to the value observed in a subject not receiving a vaccine of the disclosure). In some embodiments, a vaccine as described herein does not substantially induced an antibody-dependent enhancement of infectivity (ADEI) in the subject. In some embodiments, a vaccine induces a neutralizing antibody response in the subject that is substantially greater than any ADEI induced in the subject.

Any number of diseases can be prevented and/or treated using the present compositions and/or methods. In some embodiments, an infectious disease is prevented and/or treated. In some embodiments, a bacterial infectious disease is prevented and/or treated. In some embodiments, a viral infectious disease is prevented and/or treated. In some embodiments, a fungal infectious disease is prevented and/or treated. In some embodiments, a protozoal infectious disease is prevented and/or treated. In some embodiments, a helminthic infectious disease is prevented and/or treated. In some embodiments, a cancer is prevented and/or treated. In some embodiments, a bacterial, viral, fungal, protozoal, and/or helminthic infectious disease is prevented and/or treated. In some embodiments, a coronavirus infectious disease is prevented and/or treated. In some embodiments, COVID-19 (i.e., the disease caused by SARS-CoV-2 infection) is prevented or treated.

5. Kits

In another aspect, kits are provided herein. In some embodiments, the kit comprises a vaccine of the disclosure (e.g., a vaccine comprising one or more of the present immunogenic conjugates or antigens, or comprising a vector comprising polynucleotides encoding one or more antigens or immunogenic conjugates of the disclosure, and optionally a pharmaceutically acceptable carrier). In some embodiments, the kit comprises an adjuvant. In some embodiments, the kit is for inducing an immune response against an antigen, e.g., a coronavirus spike, E, M, or N protein, a fragment thereof, or a combination thereof. In other embodiments, the kit is for preventing or treating a disease, e.g., COVID-19. In some embodiments, the kit is for inducing a B-cell (i.e., antibody) response against one or more antigens. In some embodiments, the kit is for inducing a T-cell response against one or more antigens. In some embodiments, the kit is for inducing a B-cell response against one antigen (e.g., an antigen present in an immunogenic conjugate as described here) and a T-cell response against a second antigen (e.g., a second antigen as described herein).

Kits of the present disclosure can be packaged in a way that allows for safe or convenient storage or use (e.g., in a box or other container having a lid). Typically, the present kits include one or more containers, each container storing a particular kit component such as a reagent, a control sample, and so on. The choice of container will depend on the particular form of its contents, e.g., a kit component that is in liquid form, powder form, etc. Furthermore, containers can be made of materials that are designed to maximize the shelf-life of the kit components. As a non-limiting example, kit components that are light-sensitive can be stored in containers that are opaque.

In some embodiments, the kit contains one or more elements, e.g. syringe, useful for administering compositions (i.e., a pharmaceutical composition as described herein) to a subject. In yet other embodiments, the kit further comprises instructions for use, e.g., containing directions (i.e., protocols) for the practice of the present methods (e.g., instructions for using the kit for enhancing an immune response in a subject to an antigen from a pathogen such as SARS-CoV-2). While the instructional materials typically comprise written or printed materials they are not limited to such. Any medium capable of storing such instructions and communicating them to an end user is contemplated by this disclosure. Such media include, but are not limited to electronic storage media (e.g., magnetic discs, tapes, cartridges, chips), optical media (e.g., CD ROM), and the like. Such media may include addresses to internet sites that provide such instructional materials.

6. EXAMPLES

The present disclosure will be described in greater detail by way of specific examples. The following examples are offered for illustrative purposes only, and are not intended to limit the disclosure in any manner. Those of skill in the art will readily recognize a variety of noncritical parameters which can be changed or modified to yield essentially the same results.

Example 1. A Conjugate Polypeptide Vaccine Comprising the SARS-CoV-2 S1 Domain Linked to an Anti-CD3 Single-Chain Variable Fragment This example provides a conjugate polypeptide that is capable of binding to both B cells with surface receptors reactive to the SARS-CoV-2 spike protein "S1" domain and to T cells bearing the abundant T-cell surface protein, CD3. When included in an anti-SARS-CoV-2 vaccine regimen such as those described below, this conjugate polypeptide elicits antibody responses to the S1 domain that can contribute to protection against COVID-19.

SARS-CoV-2 enters cells through the activities of a spike protein (S) which has receptor-binding (S1) and membrane fusion (S2) regions. The SARS-CoV-2 spike shows many features of conventional class-I fusion proteins, including the presence of distinct heptad repeats within the fusion domain. Antibodies to the S1 domain can block infection with SARS-CoV-2 by blocking interaction of the spike protein with its receptor, the ACE2 protein. CD3 is a multimeric protein complex composed of four polypeptide chains (epsilon, gamma, delta, and zeta) that associates with the T-cell receptor (TCR) and plays a critical role in transducing activating signals from the TCR to the inside of the T-cell.

Figure 5:
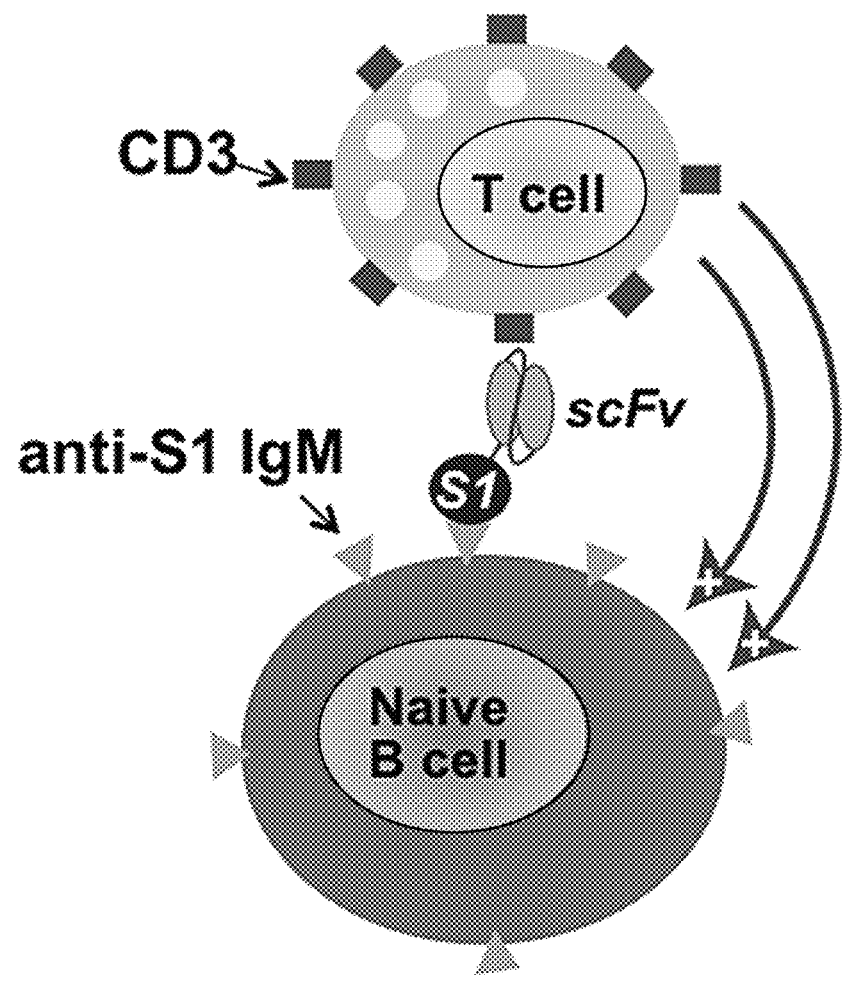

We created a conjugate polypeptide comprising the S1 region of the SARS-CoV-2 spike and a CD3-binding polypeptide (see, e.g., FIG. 5) by fusing coding sequences for the following protein elements: tissue plasminogen activator signal sequence (to permit secretion of the conjugate polypeptide from the cell), an anti-CD3 scFv derived from the murine anti-CD3 antibody, SP34 (see, e.g., US Patent Application Publication No. 2016/0068605 A1); a flexible linker; and SARS-CoV-2 S1 (codon optimized). The resulting amino acid sequence is shown as SEQ ID NO. 1. A codon-optimized nucleic-acid sequence for this polypeptide (SEQ ID NO. 2) was synthesized and cloned into the pUC19 plasmid downstream of the EF1-alpha promoter sequence (including its first intron) and upstream of the SV40 poly-adenylation sequence.

To test the CD3-binding function of this conjugate polypeptide, the resulting plasmid was transfected into 293 cells by calcium phosphate precipitation. A supernatant from the transfected cells was applied to tissue-culture plates to allow binding of secreted proteins to the surface of the plate, resulting in an immobilized array of such secreted proteins, which if bound to TCRs should send activating signals to T cells. We applied T cells from rhesus macaques to coated wells or control wells. Staining with fluorescent antibodies and data collection on a flow cytometer revealed that the immobilized conjugate polypeptide activated T cells, resulting in both CD69 up-regulation on the cell surface and interferon-gamma production intracellularly (FIG. 1). This result confirmed binding of the conjugate polypeptide to CD3 molecules on the T-cell surface.

Example 2. Providing a SARS-CoV-2 Vaccine Candidate

The present example provides a SARS-CoV-2 vaccine candidate that (i) simultaneously provokes T-cell and antibody responses, to minimize the risk of antibody-dependent enhancement; (ii) is proven effective in macaques; and (ii) is ready for future phase-I testing in humans. The vaccine platform combines rapid development (DNA administration) with broad, robust T-cell responses (due to CMV vector) and neutralizing antibody responses to the spike S1 domain.

Traditional vaccine development for previously unknown pathogens takes years, but preservation of human health may require a faster response—on the scale of months (1). Accelerated development is complicated, however, by the lack of adequate animal models for emerging pathogens; the danger of antibody-dependent enhancement of infectivity (ADEI), which can occur whenever sub-optimal antibody responses are induced (2); and by the difficulty of developing new manufacturing processes for subunit, attenuated, or vectored vaccines.

The self-launching CMV DNA platform ($_{SL}$CMV) mitigates or eliminates these complications, permitting rapid development of new vaccines that elicit immune responses of extraordinary breadth and power, localized to the mucosal surfaces threatened by SARS-CoV-2. The vaccines are administered as cytomegalovirus genomes that "launch" vectored vaccine replication in vivo, resulting in strong immune responses having the unique character associated with CMV infection. Features of $_{SL}$CMV include: (i) Based on the Towne HCMV strain, proven safe for use in humans of all ages; (ii) Immune responses in CMV-seropositive and -seronegative individuals due to CMV capacity for super-infection and proprietary deletions to the CMV genome; (iii) T-cell responses of extraordinary breadth and intensity that "paint" the vaccine antigen; (iv) Proven capacity to elicit balanced responses including antibodies, $CD4^+$ T cells, and $CD8^+$ T cells—without reliance on or dominance of any single effector response; (v) Localization of responding T cells to mucosal surfaces due to effector-memory phenotype; (vi) Engineering of new vaccine candidates in weeks to months; and (vii) Single manufacturing process based on plasmid production in E. coli.

Most coronavirus vaccines under development are designed to elicit antibodies. Such vaccine strategies must be undertaken with caution due to possible antibody-dependent enhancement (ADEI), especially when antibody levels are low (2). Highly concentrated antisera against SARS-CoV-1 were shown to neutralize the virus, whereas diluted antibodies caused ADEI in human promonocyte cell cultures. On the other hand, T cell responses often target highly conserved internal proteins and are long lived. Indeed, airway memory $CD4^+$ T cells were shown to mediate protective immunity against SARS-CoV-1 and MERS-CoV. We hypothesize that self-launching CMV DNA vaccines against SARS-CoV-2 can provide broad and protective adaptive immunity localized to mucosal surfaces.

Part 1: Characterize Immune Responses in Rhesus Macaques to Self-Launching CMV/SARS-CoV-2 Vaccines Designed to Provoke T-Cell or Antibody Responses.

Transgenes in CMV-vectored vaccines that are driven by constitutive promoters elicit robust T-cell responses but little or no accompanying antibody response; transgenes expressed from a powerful late promoter such as pp65b elicit robust antibody responses and weak T-cell responses. Using these strategies, we created candidate $_{SL}$CMV DNA vaccines that are designed to elicit dominant T-cell responses to SARS-CoV-2 E, M, and N proteins and strong neutralizing-antibody responses to the spike S1 domain. The latter candidates express the spike S1 domain either unmodified or linked to anti-CD3 scFv, which physically links B cells producing anti-S1 antibodies to T cells capable of providing help. Adaptive immune responses are followed systemically and at mucosal surfaces over time. Production of neutralizing vs. enhancing antibodies is monitored using reporter virus particle (RVP) assays.

Part 2: Evaluate Protective Efficacy of $_{SL}$CMV/SARS-CoV-2 Vaccines Against the Davis Isolate of SARS-CoV-2 in Rhesus Macaques.

SARS-CoV-2 isolated from a patient is grown and characterized, and pathogenesis of the virus is assessed in monkeys. We test the protective efficacy of the T-cell and B-cell vaccines created in Part 1 by challenging vaccinated animals with SARS-CoV-2. T- and B-cell vaccines are tested separately or together, to test the relative contributions of each arm of the adaptive immune system to protection vs. disease enhancement.

Part 3: Test Safety and Potential Efficacy of Self-Launching Human CMV-Vectored Vaccines in Macaques.

It has been recently been shown that human CMV (HCMV)-vectored vaccines elicit strong effector-memory T-cell responses in macaques. We therefore create HCMV-vectored vaccines as candidates for future human clinical trials, develop GMP processes for production, and test an $_{SL}$HCMV regimen for efficacy in macaques. The HCMV-vectored vaccines to be used for this in-vivo experiment will be selected based on the outcome of protection studies using $_{SL}$RhCMV in Part 2.

Significance

Rapid vaccine development for emerging infectious threats is an unmet need: Traditional vaccine development for previously unknown pathogens is slowed by fundamental biological issues that are not easily resolved. Most importantly, though induction of high-titer neutralizing antibodies (nAbs) would seem an obvious approach, we do not know what titer of nAbs would be protective in practice, nor how this threshold varies across the extremes of age and comorbidities. For any emerging pathogen we do not know if poor antibody responses, which are particularly likely in the old and young, may lead to antibody-dependent enhancement of infectivity (ADEI).

Immune correlates of successful vaccination against SARS-CoV-2 are poorly defined: Most coronavirus vaccines presently under development target the most variable part of the spike glycoprotein and induce antibody responses only against the virus present in the vaccine. SARS-CoV-1 escape mutants develop in the presence of single anti-receptor binding domain (RBD) nAbs or combinations of two nAbs both in vitro and in mice (2,3). Vaccines that exclusively elicit antibodies must additionally be approached with caution due to possible ADEI, especially when antibody levels are low (4). Highly concentrated antisera against SARS-CoV-1 were shown to neutralize virus infectivity, whereas diluted antibodies caused ADEI in human promonocyte cultures, leading to cytopathic effects and increased levels of TNF-α, IL-4, and IL-6 (5-7). Vaccine candidates based on the full-length SARS-CoV-1 spike were demonstrated to induce non-neutralizing antibodies and the immunized animals were not protected. Instead they experienced adverse effects like enhanced hepatitis, increased morbidity, and stronger inflammatory responses (8,9).

T-cell responses elicited by CoV vaccines also play crucial roles in protection and clearance. Clearance of MERS-CoV infection was impossible in T cell-deficient mice, but was achieved in mice lacking B cells (10). Further, airway memory CD4$^+$ T cells were shown to mediate protective immunity against SARS-CoV-1 and MERS-CoV (11). Most vaccine types do not elicit large numbers of memory CD4$^+$ T cells—but CMV-vectored vaccines do, as shown below. The T cells responding to CMV-vectored vaccines localize to airways among other effector sites and are recovered by bronchoalveolar lavage (12). CMV-responsive T cells recapitulate other essential features of cells shown to be protective against SARS-CoV-1, including CXCR3 expression, IFN-γ production, and IL-10 production (13).

CMV-vectored vaccines can elicit robust antibody responses: Although CMV vaccines elicit weak antibody responses to some transgenes driven by heterologous promoters, CMV infections and vaccinations elicit robust antibody responses to proteins expressed under control of the endogenous pp65b promoter. The promoter is one of the most active in the late phase of CMV infection, after DNA replication. It has been found, for example, that 4/4 rhesus macaques vaccinated with a CMV vaccine carrying the Ebola virus glycoprotein (GP) under control of the pp65b promoter produced GP-specific antibodies, which were boosted after a second vaccine administration (21). The high levels of GP antibodies induced by RhCMV/EBOV-GP and their ability to undergo IgG class switching indicates the presence of sufficient CD4$^+$ T-helper function. Three of these four macaques having the highest anti-GP titer were protected against lethal EBOV challenge.

An important characteristic of CMV vectors for their use against emerging pathogens is the capacity for re-administration to previously exposed individuals. This ability enables repeated use of CMV-vectored vaccines to protect against a series of emerging threats over time.

Impracticality of conventional CMV vaccines for use against emerging pathogens: Despite their immunologic advantages, practical obstacles prevent rapid development of CMV vaccines for human clinical use, when those vaccines are delivered as live virus. The most significant problem is the tremendous difficulty of producing a uniform test article, at scale, from a slow-growing and mutable betaherpesvirus (29).

Innovation

Vaccination with CMV vector in its nucleic acid form: While transfection with CMV genomic DNA is the cornerstone of many in vitro techniques, and other investigators have experimented with delivery of herpes-virus genomes as plasmids within *Salmonella* organisms (26), to our knowledge delivery of naked or chemically complexed CMV genomic DNA as a vaccine has not been attempted. We demonstrate below that gene expression, genome replication, viremia, and immune responses occur after administration of CMV BAC DNA.

Figure 2:
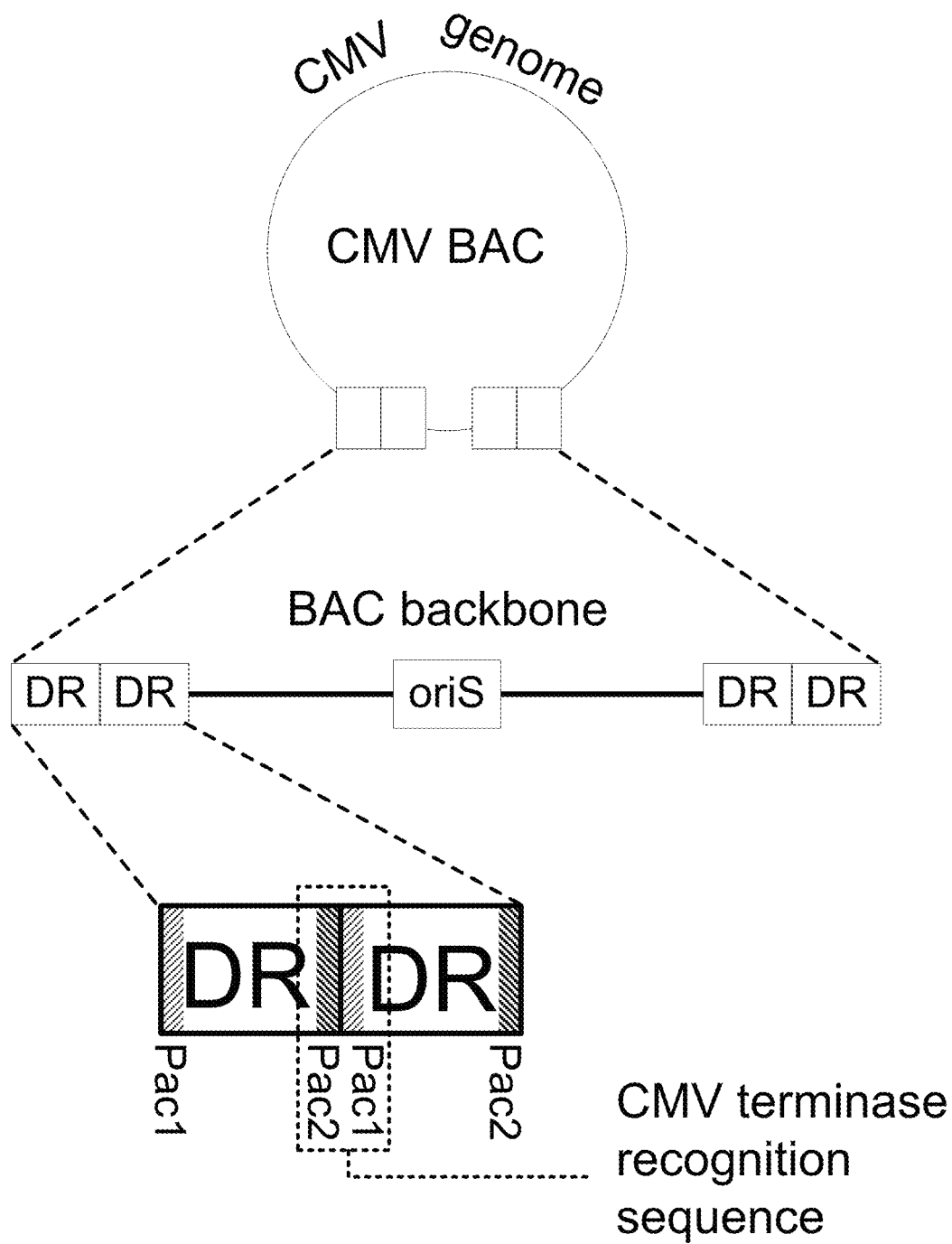
FIG. 2. Cartoon depicting self-launching RhCMV BAC DNA constructs. In the depicted construct, each terminase complex recognition locus (TCRL) consists of two DR repeats. The two TCRLs flank BAC sequences, including the prokaryotic origin of replication, oriS.

Placement of the BAC origin of replication at a CMV genome terminus to allow BAC excision by the CMV terminase complex: To utilize a CMV vector in its DNA form for vaccination requires an alteration in the current CMV BAC construct, so that the BAC backbone can be excised without recombinase or nuclease expression in vivo. CMV has a relatively strict packaging limit due to the need to package unit-length genomes into an icosahedral capsid. The current CMV BAC utilizes an endogenous recombinase gene placed within the BAC portion of the DNA construct. Upon transfection of mammalian cells, the recombinase is expressed and excises the BAC replication machinery from the replicating genomes. To make a BAC DNA vector suitable for in vivo delivery in humans, we re-organized the CMV genome termini to enable excision of the BAC without the requirement for expression of a recombinase. Our reconfigured BAC constructs utilize the viral terminase complex to eliminate the bacterial origin of replication during the packaging step of CMV replication (FIG. 2). We have moved the location of the BAC origin and replication machinery from its current location (RhCMV US1/2) to between terminase complex recognition loci (TCRLs) that comprise viral direct repeats. We show below that this arrangement permits efficient replication and packaging of the vaccine genomes after introduction to host cells in vivo.

Novel improved RhCMV-SIV vaccine: First-generation RhCMV-SIV vectors carry an intact, endogenous viral IL-10 gene, which suppresses host immune responses (27-31). We have created a second-generation RhCMV vector platform—viral IL-10-deficient RhCMV or RhCMVdIL10—that has unique immunologic features and can protect wtRhCMV-negative infant macaques while first-generation vaccines do not (27).

Figure 3A:
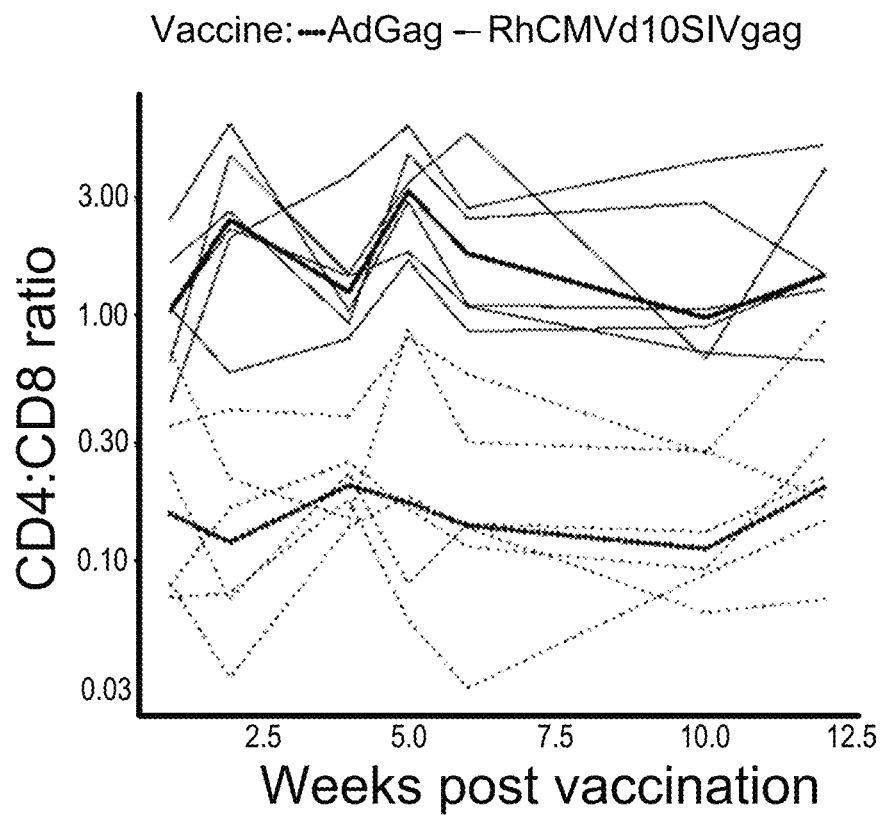
FIGS. 3A-3B. CMV-vectored vaccines lacking UL111A elicit strong CD4+ and CD8+ T-cell responses at mucosal surfaces.
Figure 3B:
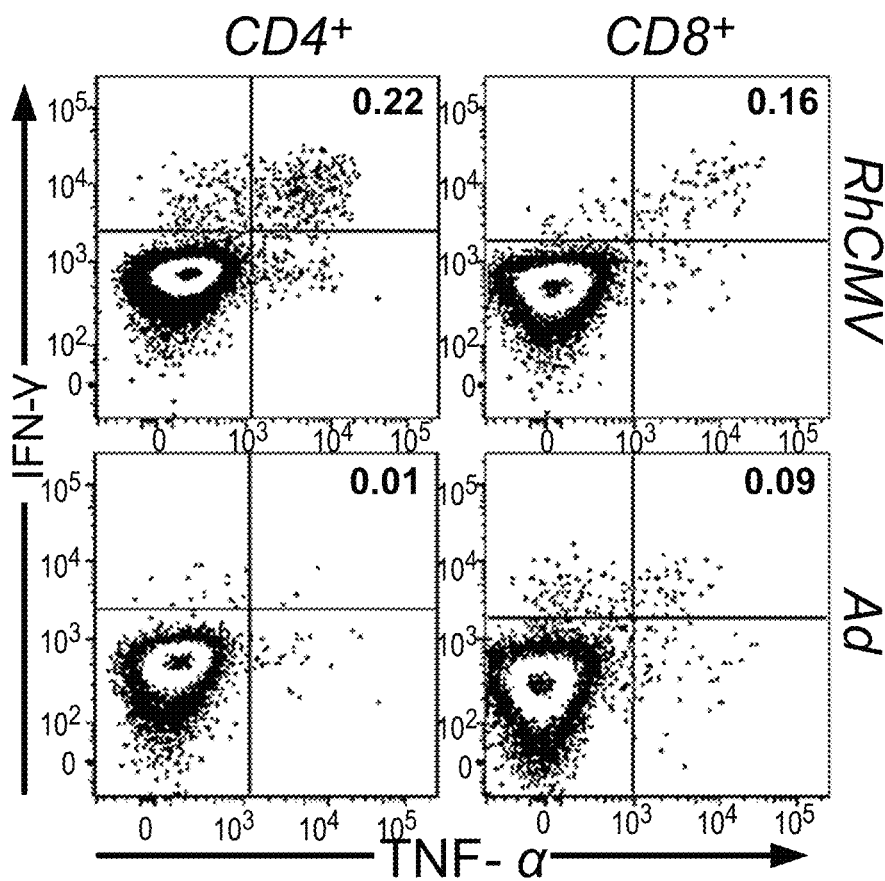
Figure 4:
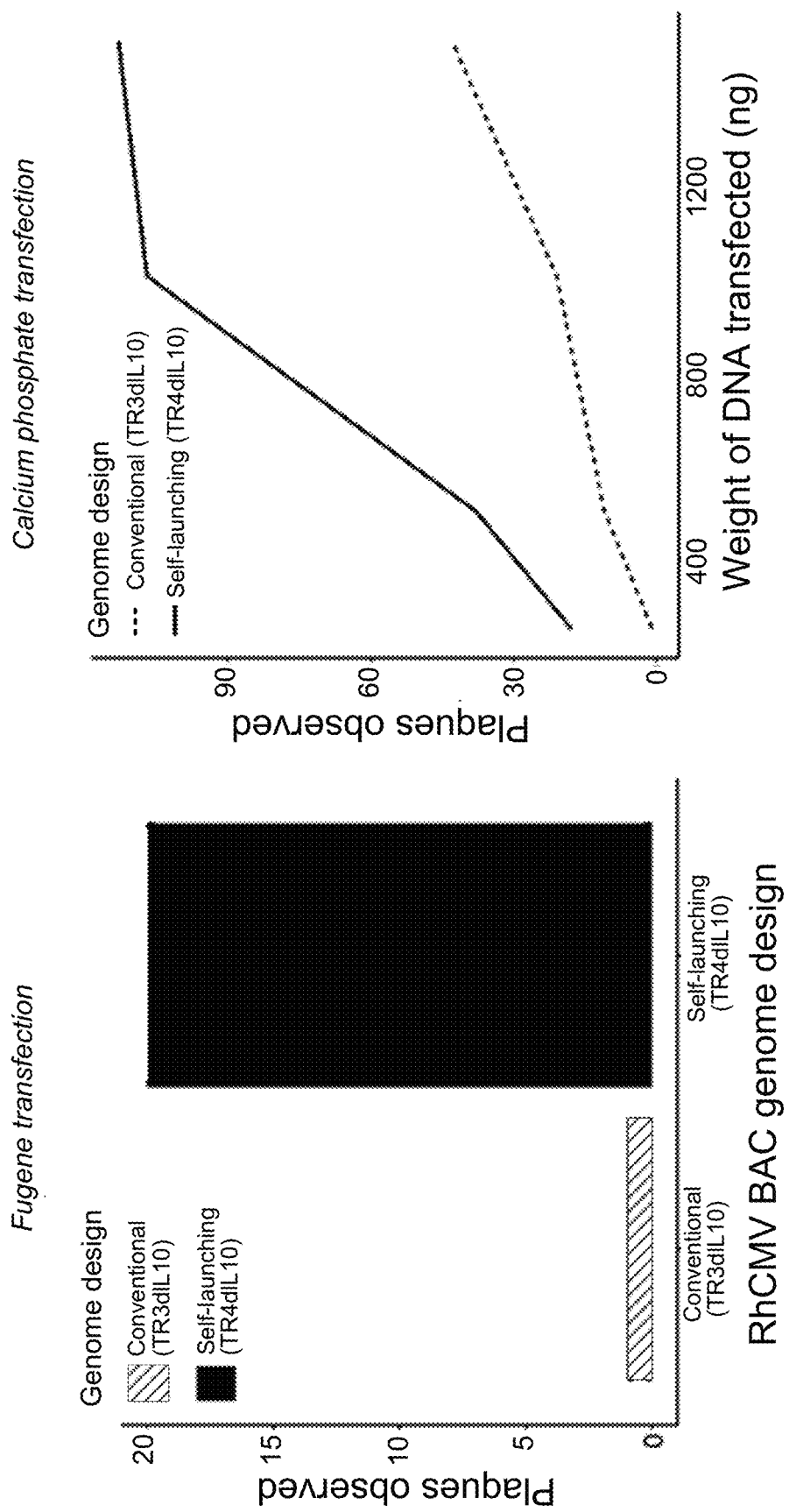
FIG. 4. Introduction of terminase complex recognition loci (TCRLs) surrounding the BAC origin of replication provides superior conversion of CMV BAC genomic DNA to replicating virus in vitro. Left, transfection of one microgram of CMV BAC genomic DNA using FuGene 6 leads to production of only one plaque when using conventional CMV BAC genomic DNA (TR3dIL10), but 20 plaques when using a self-launching construct with CMV TCRLs surrounding the BAC origin (TR4dIL10) as in FIG. 2. Right, using calcium phosphate-mediated transfection, comparison of plaque formation across a range of input DNA amounts. The self-launching genome with TCRLs surrounding the BAC origin is superior at every DNA-input level.

Example 3. CMV-Vectored Vaccines Elicit Uniquely Broad and Strong T-Cell Responses in the CD4 and CD8 Compartments T effector-memory (TEM) cells are the predominant type of T cell in mucosal effector sites (14). CMV infections are associated with lifelong, high-frequency $CD4^+$ and $CD8^+$ T cell responses, in the effector-memory compartment, that protect against CMV pathology but do not eliminate the CMV infection or prevent CMV superinfection (15-19). TEM cells elicited by CMV-vectored vaccines, furthermore, recognize diverse and unusual epitopes, including dominant responses to epitopes restricted by class E and class II major histocompatibility complex (MEW) molecules (20). T cells responding to CMV vaccines recognize more than three times as many peptide epitopes as those responding to other vaccine types, resulting in responses that "paint" the vaccine antigen and should prevent pathogen escape (20). Although much published work has focused on $CD8^+$ T-cell responses, CMV vaccines stimulate equivalently strong $CD4^+$ T-cell responses, a feature not seen with other vectored vaccines (FIG. 3A). Critically, the unique abundance of responsive $CD4^+$ T cells in the airways of vaccines (FIG. 3B) fits the requirements described for protection against SARS-CoV-1 (11).

Figure 6:
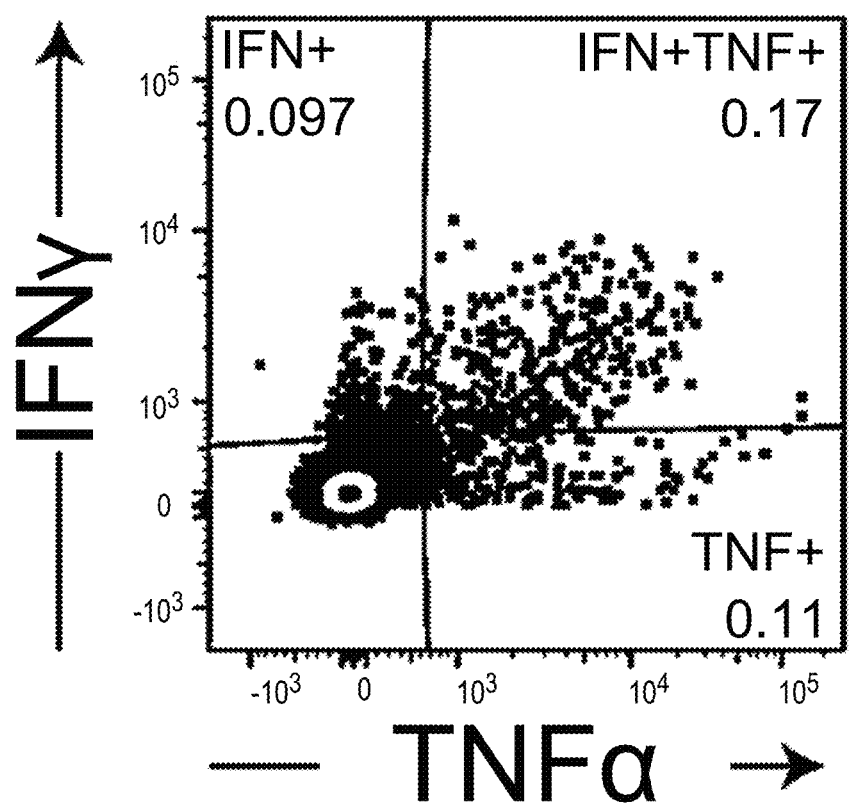
FIG. 6. Vaccination with 100 µg of RhCMVdIL10 vaccine BAC DNA subcutaneously is sufficient to elicit immune responses. Shown are immune responses to pRhCMV-MA-GEA4 seen as early as one week after priming.

Example 4. DNA-Based, Self-Launching CMV-Vectored Vaccines can be Rapidly Engineered and Manufactured for Broad Protection Against Emerging Threats To allow for manipulation using prokaryotic genetics, RhCMV-SIV vaccines are maintained as circular bacterial artificial chromosomes (BACs) containing vector genomic DNA with an embedded BAC origin of replication (ori), flanked by recognition signals for a site-specific recombinase or restriction enzyme. Excision of the BAC origin, in vitro or by site-specific recombination following transfection, is required for efficient replication and packaging. We re-engineered these vectors to contain a BAC origin outside the viral genome and flanked by CMV terminase complex recognition loci, allowing automatic excision by CMV terminase as the vector begins to replicate (FIG. 2). The new vectors therefore do not require either in vitro digestion or Cre recombinase expression and are delivered to vaccine recipients as stable, circular DNA molecules. Upon reaching a recipient-cell nucleus, these CMV vaccine genomes enter the viral replication cycle and produce a cascade of virions that provoke protective immune responses identical to those elicited by CMV-vectored vaccines delivered as virions. Indeed, the resulting vaccine responses arise earlier and are often stronger than those elicited by virions, most likely due to administration of more vaccine genomes by a factor of 10,000 (FIG. 6).

Example 5. Characterize Immune Responses in Rhesus Macaques to Self-Launching CMV/SARS-CoV-2 Vaccines Designed to Provoke T-Cell or Antibody Responses We hypothesize that self-launching RhCMV vaccines will generate T-cell responses as broad as those administered in virion form, and that linkage of the SARS-CoV-2 S1 immunogen to an anti-CD3 scFv fragment will increase the speed and potency of NAb responses.

The rationale for this hypothesis is that we have demonstrated that SLRhCMV vaccines are launched into replicating virus that can be detected in blood for weeks after administration, and that we expect these forms to elicit T-cell responses (in group B) as broad as those elicited by conventional encapsidated CMV (~90 peptides per 1000 vs 12 for adenoviral vectors).

Figure 7:
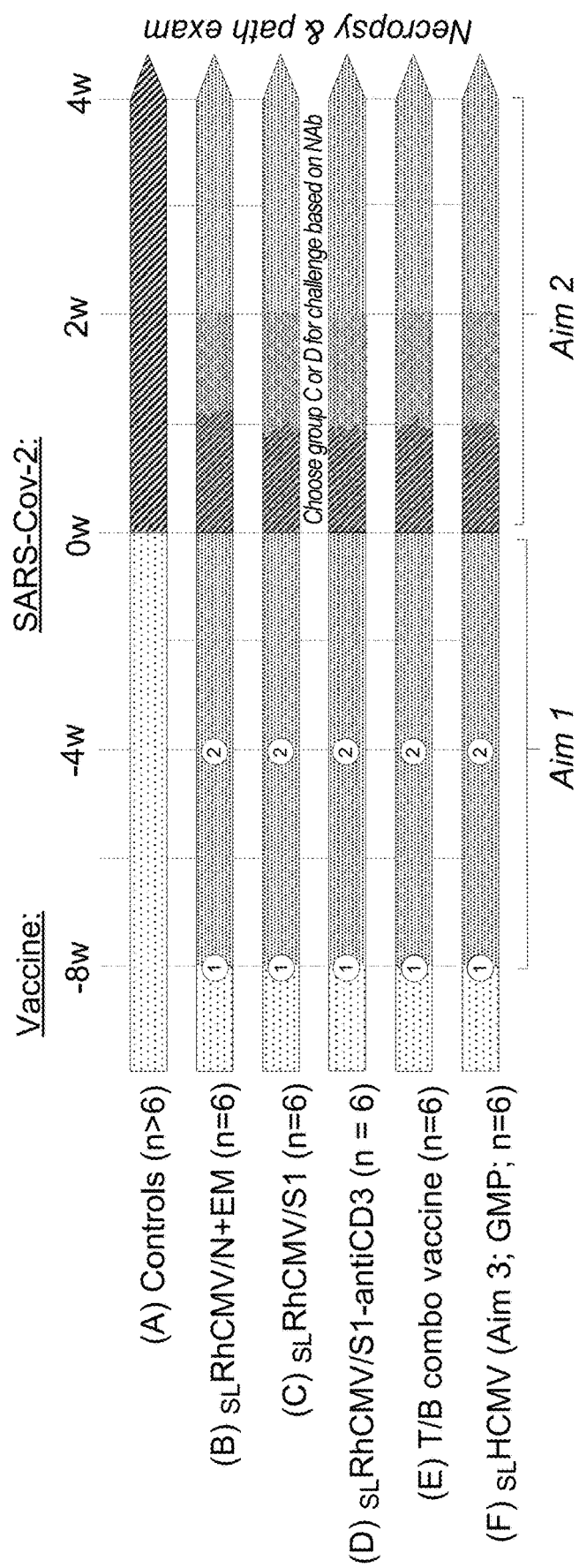
FIG. 7. Overview of protocol.

With respect to the SLCMV vaccines designed to elicit B-cell responses (groups C-D), we compare the secreted spike S1 domain to the same protein linked to an scFv fragment that binds to CD3 (FIG. 7). The result is a molecule that can "bridge" S1-specific B cells and any T cell in the vicinity. Our preliminary data show that idiotypes linked to anti-CD3 in a bispecific antibody rapidly elicit very strong anti-idiotype antibodies. Thus we expect delivery of the spike S1 domain linked to an anti-CD3 scFv to elicit stronger antibodies than S1 alone.

We test immune responses to three candidate vaccine components, all of which are administered twice, eight and four weeks before challenge (FIG. 7). The T-cell component contains a mixture of SLRhCMV/N and SLRhCMV/EM vaccines. We assess the strength and breadth of T-cell responses to these vaccines (group B), to provide data for a later examination of correlates of protection. There are two candidate B-cell components (groups C and D), of which one will be chosen for efficacy testing in Example 6, due to induction of stronger neutralizing antibody responses and/or reduction in enhancement. Finally, we test a regimen consisting of the T-cell vaccine (SLRhCMV/N+EM and the chosen B-cell vaccine, administered together).

Vaccine Construction

SLRhCMV/N, SLRhCMV/EM, SLRhCMV/S1, and SLRhCMV/S1-antiCD3 are generated as self-launching BAC constructs bound by CMV terminase recognition sites as illustrated in FIG. 2. All coding sequences are codon-optimized versions of those found in SARS-CoV-2. The N and EM fusion protein cassettes are expressed under control of the EF-1alpha promoter, including its first intron, and have been recombined into the Rh213/214 region of the RhCMV genome, a location that we have repeatedly used and observed predominant T-cell responses. The S1 and S1-antiCD3scFv cassettes are expressed under control of the endogenous late RhCMV pp65b promoter and preceded by the 23-aa tPA leader sequence to encourage efficient secretion. The S1-antiCD3 fusion employs a humanized scFv region derived from the anti-CD3 clone SP34, which is a clone that we have previously employed for construction of bispecific antibodies.

Endotoxin-free BAC (vaccine) DNA is purified from cultures of *Escherichia coli* using alkaline lysis with Triton X-114 followed by two sequential isopycnic centrifugations. Endotoxin concentrations are measured using a Limulus amebocyte lysate (LAL) assay to ensure that they are below the pyrogenic threshold (5 endotoxin units/kg body weight) (32).

Vaccine Administration

Our preliminary data (FIG. 6) show that vaccination with 100 μg of RhCMVdIL10 vaccine BAC DNA subcutaneously is sufficient to elicit immune responses. BAC DNA is formulated with in vivo-jetPEI (Polyplus) according to manufacturer instructions. Briefly, 100 μg of DNA (50 μg each of RhCMVdIL10-SIVgag and -SIVenv) and 16 μL in vivo-jetPEI are separately diluted into 5% glucose solutions (1 ml), then mixed and incubated for 15 minutes.

RhCMV Vector Replication and Shedding

Vaccine-derived RhCMV DNA is measured weekly in blood and saliva samples by qPCR using our published protocols (16,33). These measurements provide an assessment of the replication and dissemination of the BAC DNA-encoded viral vector. Dissemination to various tissues is assessed by qPCR at necropsy following SARS-CoV-2 challenge in Example 6.

Immunophenotyping

The immunophenotypes of greatest interest are T-cell memory-effector subsets, which contain the greatest fraction of cells responding to RhCMV and RhCMV/SIV vaccines; NK cells with adaptive characteristics (i.e., FcεRIγ low "memory" NK); T cells with innate characteristics (NKG2A$^+$); and antigen-presenting cells, especially monocytes, expressing CD80/83/86. All of these cell populations are altered after wild-type or vaccine-strain RhCMV infection. All are assessed using a set of three flow cytometry panels used in our previously published work to examine antigen-presenting, T, and NK cells (34).

Antigen-Specific T Cell Responses

Assay wells containing up to 1M PBMC or LNMC cells are stimulated with vehicle (negative control for DMSO toxicity), overlapping RBD, S1, E, M, and/or N peptides (Intavis), or PMA/ionomycin (positive control). Inhibitors such as VL9 peptide or anti-HLA-antibodies are applied one hour before stimulation begins and added again with the peptide stimulus. After 16 h the cells are stained using fixable live-dead stain as well as antibodies reactive to CD3, CD4, CD8, CCR7, CD95, IL-2, IL-17, IFN-γ, and TNF-α. The fraction of cytokine-secreting CD4$^+$ and CD8$^+$ T cells is determined by cytometry on, e.g., a BD Fortessa or FACSymphony.

Antibody Responses

Induction of binding antibodies to the spike S1 domain is measured by ELISA on weekly plasma samples according to our published protocols (16). Neutralizing or enhancing antibodies are tested by RVP assay.

Combination T- and B-Cell Vaccine (Group E)

The binding and neutralizing antibody responses in groups C-D are fully characterized, and the group having superior neutralizing titers and lower or no enhancement is chosen for SARS-CoV-2 challenge (see, Example 6). Furthermore, after selecting the best candidate for induction of Nabs, the TB combination vaccine group (group E) is formed. This group receives combined vaccination with SLRhCMV/N, SLRhCMV/EM, and the chosen B-cell vaccine.

Interpretation of Data

We hypothesize that our SLRhCMV vaccines, delivered as DNA, elicit robust T- and B-cell responses and that the latter responses are stronger with the antigen is linked to anti-CD3 scFv. To determine if those responding cells are found in the most relevant tissue, lung, we perform bronchoalveolar lavage and assay T-cells that can be recovered from the airway.

Based on the ADEI that has previously been observed with other RNA viruses causing respiratory infection, including SARS-CoV-1, it is possible that some animals could display enhancement of the RVP assay after vaccination. Such a result would be important both for understanding the immunopathogenesis of COVID-19 and for interpreting the outcome of challenge experiments described below.

Statistical Analysis

Non-parametric Kruskal-Wallis tests are used to test between-group differences in summary measures or outcomes at single times. For longitudinal results, e.g., testing association between T-cell and antibody responses, generalized linear mixed models (GLMMs) are used as the analysis framework, with random effects correcting for the within-animal correlation induced by serial measurements.

Example 6. Evaluate Protective Efficacy of SLCMV/SARS-CoV-2 Vaccines Against the Davis Isolate of SARS-CoV-2 in Rhesus Macaques We hypothesize that strong T-cell responses localized to airways protect against SARS-CoV-2 and additionally against antibody-dependent enhancement. The rationale for this hypothesis is that T-cell responses are the body's most important defense against intracellular parasites and would be expected to protect against SARS-CoV-2, if present in the virus's target tissues at high enough frequency. Indeed, it has previously been shown that airway memory CD4$^+$ T cells mediate protective immunity against both SARS-CoV-1 and MERS-CoV (see, e.g., Zhao, *Immunity* 44:1379). Furthermore, ADEI is thought to occur to due enhanced uptake of virus into cells, which as a result are co-opted and permit productive replication—however, virus internalized due to ADEI should be susceptible to elimination by T cells.

We developed a uniform challenge and monitoring protocol so that consistent sets of virologic, immunologic, and pathologic data may be leveraged across experiments. Macaques vaccinated as shown in the diagram (groups B-E in FIG. 7) will be challenged at least 8 weeks after priming vaccination and followed by repeated clinical assessments; radiography; collection of respiratory and mucosal secretions (e.g., by bronchoalveolar lavage, tracheal wash, or nasal wash) as well as saliva, urine, and stool; blood draws; and tissue collection (see, e.g., www.biorxiv.org/content/10.1101/2020.07.07.191007v1).

Virus for Infections

A virus stock produced by expanding the SARS CoV-2 isolate that we obtained from the UC Davis patient will be used for animal inoculations, designated 2019-nCOV/USA-CA9/2020. If outgrowth of that virus is insufficient, we will instead use the SARS CoV-2 isolate USA-WA1/2020 (BEI Resources). To infect animals, approximately 6×10$^6$ TCID50 in total will be instilled into the conjunctiva, nostrils, and trachea of anesthetized monkeys in 5 ml of 0.9% sterile saline to recapitulate relevant transmission routes of COVID-19.

Sampling and Assays

Body temperature, weight, and activity are monitored throughout. CBCs and serum chemistry are obtained on all blood samples to monitor host responses and organ function. The sampling schedule is designed to comprehensively characterize viral shedding, cytokine responses, and adaptive immunity to understand how changes in these parameters reflect lung pathology. The sampling schedule and procedures have been used successfully by us to characterize influenza A infection in macaques. Intensive sampling during the first week enables us to study acute virology and host responses. Because ACE2 is expressed in the gastrointestinal and genitourinary tracts of rhesus and humans, in addition to respiratory secretions, we evaluate virus shedding in saliva, urine, and stool. At necropsy (d28) we collect all relevant tissues including salivary glands, lung, lymph nodes, kidney, and gut to evaluate virus localization and immune responses by PCR, molecular histology (IHC, ISH), and cytometry. Tissues are evaluated for gross pathology, histopathology, and tissue vRNA levels. Necropsies are performed by a board-certified pathologist.

Viral RNA is recovered from respiratory-tract samples using Thermo's MagMAX Viral/Pathogen Nucleic Acid Isolation kit (as recommended by the CDC for COVID-19) and quantified by amplification of a segment of the SARS-CoV-2 nucleoprotein (N) gene. The specific RT-PCR assay to be used in these studies is under evaluation. The CNPRC team is comparing the sensitivity, specificity, and reproducibility of validated RT-PCR assays from CDC, UCD Health Clinical labs, Wisconsin NPRC, and commercial vendors. We select the most consistent assay. Immunologic analysis are performed as described above, in Example 5.
Interpretation of Data If our hypothesis is correct, then group B animals are protected against SARS-CoV-2 vaccination, despite having mounted an immune response that consists almost exclusively of T cells. Group C or D animals (whichever is chosen in Example 5) may also be protected but we are alert to the possibility of ADEI, which would be indicated by increased viral loads, shedding, or pathologic findings in animals with moderate antibody titers, whether or not they are shown to be enhancing in the RVP assay.
Statistical Analysis Summary findings or those assessed at individual time points, e.g., at necropsy, are assessed using non-parametric tests, with p values adjusted according to Benjamini and Hochberg. Longitudinal results are evaluated with linear mixed models (with generalization if necessary), with random effects accommodating the within-animal dependence induced by serial measurements.

Example 7. Test Safety and Potential Efficacy of Self-Launching Human CMV-Vectored Vaccines in Macaques We hypothesize that SLHCMV vaccines can be produced at 10-20 gram scale in a GMP process, can be safely administered to macaques, and can protect against SARS-CoV-2 challenge. The rationale for this hypothesis is that, surprisingly, it has recently been shown that attenuated HCMV vectors can elicit and maintain T effector-memory responses against inserted antigens in rhesus macaques (see, e.g., Caposio Sci Rep 9:19236). Thus the rhesus macaque model may offer a setting in which to test efficacy of candidate SLHCMV vaccines, produced under GMP conditions, against SARS-CoV-2. If the HCMV-vectored vaccines can be proven safe and effective in macaques then they would be candidates for later clinical trials.

SLHCMV versions of all four vaccines administered to macaques of groups B-D in Example 5 are engineered. In addition, after challenge of groups B-E, GMP production is undertaken of those SLHCMV vaccines that form part of the optimal regimen. For example, if the animals in group B are best protected against pathology, production is undertaken of SLHCMV/N and SLHCMV/EM. The resulting GMP products are sent to UC Davis for vaccination of macaques and efficacy testing against SARS-CoV-2.
SLHCMV Vaccine Genomes The HCMV vaccine genomes being engineered are based on the Towne vaccine strain due to its excellent safety record. The vaccine are orthologous to the RhCMV genomes engineered at Davis. The viral interleukin-10 gene is absent in both cases; sequences are inserted in an intergenic region near US28 for elicitation of T-cell responses; and are instead placed under control of the pp65b promoter for elicitation of antibody responses. The BACs carry codon-optimized SARS-CoV-2 sequences driven by the same promoters.

The plasmid backbone sequence used allows maintenance of the plasmid at approximately single copy (in DH10B cells employing oriS to maintain the plasmid) or at ~15-30 copies (after induction of TrfA expression and its interaction with the alternative oriV origin). The BAC DNA is purified at laboratory scale by double sequential CsCl equilibrium gradient centrifugation followed by dialysis into PBS. The integrity of the plasmid preps is confirmed by restriction enzyme footprinting, PCR amplification of expression cassettes, and deep sequencing after tagmentation.

GMP production is undertaken with a CMO partner. Upstream process development focuses on optimizing transformation and culture conditions to ensure maximum homogeneity of the test article. Downstream process development (purification after cell growth) focuses on adaptation of the CsCl-dependent process used in the laboratory to iodixanol.
Testing the Optimal SLHCMV Vaccine Regimen in Macaques (Group F)

SLHCMV vaccines are given in the same combination and at the same dose used in one of groups B-E. Immunoassays, SARS-CoV-2 challenge, and pathologic evaluation are carried out identically.
Interpretation of Data Our hypothesis predicts that SLHCMV vaccines are produced in a GMP process at sufficient scale and purity to permit eventual testing in phase-I human trials. In addition, we believe that SLHCMV-vectored vaccines could demonstrate efficacy in the rhesus macaque model. Such an outcome is perhaps counter-intuitive but is possible, based on publications in the literature demonstrating that HCMV can complete its life cycle in rhesus fibroblasts (43) and can elicit strong TEM responses in macaques.

Immune responses to SLHCMV vaccines in macaques are also of interest because they likely reflect responses achieved with minimal spread of the vaccine, as would be seen when using a fully inactivated HCMV-vectored vaccine in humans. Despite the evidence for some genome replication, the HCMV (Towne) based vaccines should be capable of minimal or no systemic spread in macaques. Thus, contrasting immune responses to RhCMV- vs. Towne-vectored antigens should reveal which qualities of immune response rely on immunomodulation alone, and which depend on vector spread.
Statistical Analysis The statistical analysis is centered on characteristics of vaccine preparations. Our previous experience suggests that single-copy BACs have mutation rates similar to other plasmids, that is, below the level of detection by amplicon sequencing (~0.1%) (46-50), imposed by the error rates of the polymerases. SLHCMV genome replication in macaques is determined by any of (i) vaccine virus sequences in plasma one week after prime or boost, (ii) gB expression in biopsy tissue from the injection site (HCMV gB-specific Abs; gB as a late gene is expressed only after genome replication), or (iii) anamnestic antibody response to HCMV gB defined by doubling of titer in the month following boost.

Example 8. A Conjugate Polypeptide Vaccine Comprising the SARS-CoV-2 RBD Domain Linked to an Anti-CD3 Single-Chain Variable Fragment We designed a conjugate polypeptide vaccine, designated s3-RBD (SEQ ID NO. 6), that is a fusion protein between a humanized anti-CD3 single-chain variable fragment (scFv) derived from the SP34 clone and the SARS-CoV-2 receptor binding domain (RBD), both preceded by a tissue plasminogen activator (tPA) signal sequence to enable secretion. RBD is a segment of the SARS-CoV-2 spike protein responsible for its binding to the human receptor, ACE2, and is a frequent target of neutralizing antibodies. s3-RBD has the capacity to bind both RBD-responsive B cells (via their cell-surface, RBD-specific antigen receptors) and helper T cells (via CD3). Without being bound by the following theory regarding the specific mechanism of action, we hypothesize that engagement of pairs or clusters of these cognate receptors on B and T cells should result in the activation of both cell types, in turn driving the continued development of the B cells. B cells that receive T-cell help are more likely to undergo somatic hypermutation and eventually develop into producers of high-affinity, RBD-specific antibodies.

To immunize rhesus macaques with a genetic vaccine expressing s3-RBD, we prepared a codon-optimized open reading frame with the nucleotide sequence given in SEQ ID NO. 7. This sequence was synthesized and then placed into an expression cassette downstream of the human EF-1-alpha promoter sequence and upstream of an SV40-derived polyadenylation signal (resulting in the complete expression cassette sequence given in SEQ ID NO. 8), using techniques known to those skilled in the art. The plasmid containing the expression cassette was prepared free of endotoxin at medium scale for administration as a DNA vaccine. The expression cassette was also cloned into the E1 region of a type-35 adenovirus shuttle plasmid, which permits transfer of DNA sequences into an E1, E3-deleted type-35 adenoviral vector.

Figure 8:
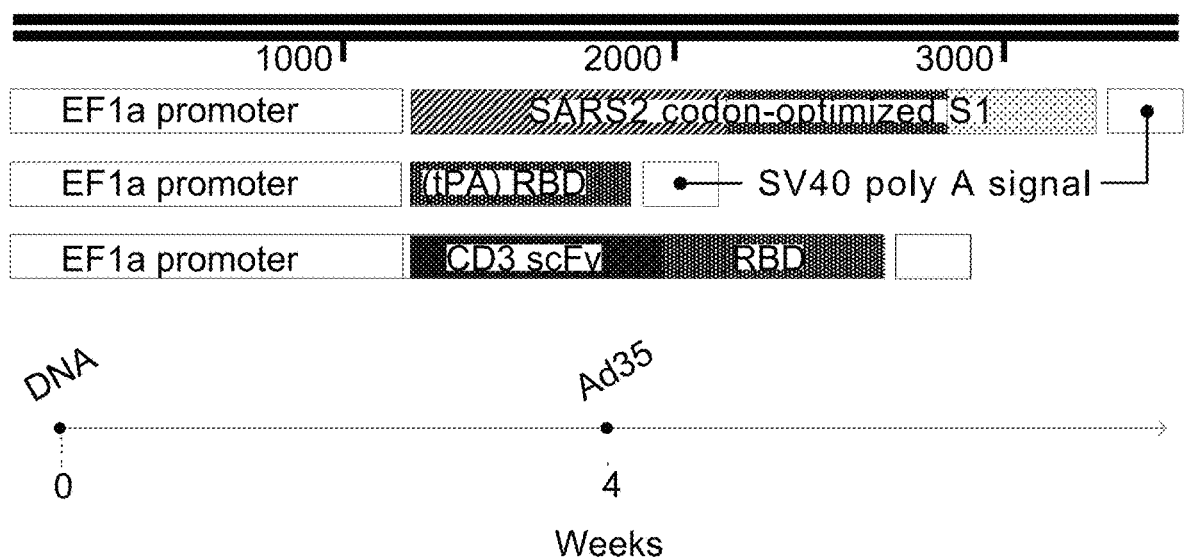
FIG. 8. Expression cassettes and experimental design. Upper, design of expression cassettes coding for the SARS-CoV-2 spike S1 domain (top, light grey), receptor-binding domain (middle, grey), or anti-CD3 scFv-RBD fusion protein (s3-RBD, black). Middle, these cassettes were delivered to rhesus macaques as electroporated DNA at day 0 of the vaccination protocol; the animals were boosted with adenovirus type 35 (Ad35) vector at approximately day 28. Lower, three macaques per group received 1 mg of DNA expressing S1, RBD, or s3-RBD at priming and $10^{12}$ particles of Ad35/S1 or Ad35/RBD at boosting.

To evaluate immune responses to our s3-RBD immunogen in the context of a genetic vaccine in non-human primates, we performed immunizations of nine monkeys using an electroporated-DNA prime (day 0) and Ad35-vectored boost (day 28; FIG. 8). The immunogens tested were the SARS-CoV-2 S1 domain, RBD domain alone, or s3-RBD, all expressed from codon-optimized ORFs under control of an EF-1 alpha promoter. A tPA signal sequence was placed upstream of both the isolated RBD domain and s3-RBD fusion protein to enable their secretion (FIG. 8).

Figure 9:
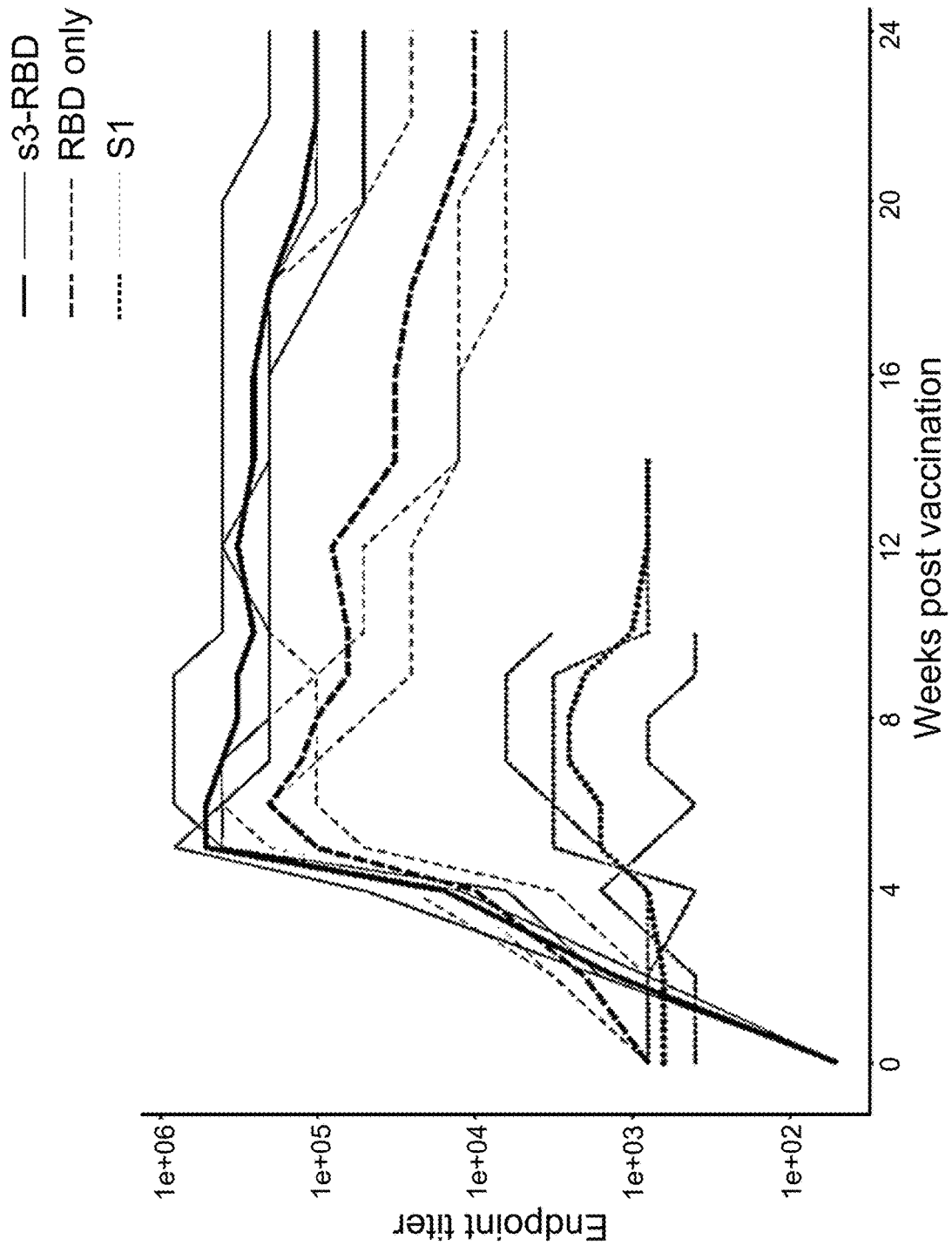
FIG. 9. Binding antibodies detected by endpoint-dilution ELISA assay. Responses of individual vaccinated macaques are shown with thinner lines; geometric mean responses by group are shown with thicker lines (S1 in dotted black, RBD alone in dashed gray, s3-RBD in solid black). Vaccination with DNA at week 0 and Ad35 at week 4 leads to binding antibody responses, above the week-0 background, in all recipients of the RBD and s3-RBD constructs. Recipients of s3-RBD priming exhibit superior responses that are both higher on average and in ⅔ cases higher than the best response developed in the RBD group. The geometric mean response to s3-RBD is 10 times higher than the geometric mean response to RBD by 24 weeks after vaccination.

Assessment of binding antibodies by ELISA during the vaccination protocol demonstrated both superiority of the RBD domain for immunization (vs. the entire S1 domain), and superior performance of the s3-RBD construct vs. RBD alone (FIG. 9). Surprisingly, the S1 immunogen performed very poorly, eliciting detectable binding and neutralizing antibodies in only one of three vaccine recipients. Note that low binding-antibody responses against S1 were appreciable by ELISA in two animals (FIG. 9) but were insignificant when compared to much higher responses in the other groups; neutralizing activity was detected in one of these two S1-recipient animals (FIG. 9, dotted black line). Immune responses to the RBD domain alone were detectable in all three animals receiving the genetic vaccines encoding it, at all post-boost time points (FIG. 9, dashed gray line). Binding antibody responses were highest, however, in the group receiving s3-RBD (FIG. 9, solid black line).

Figure 10:
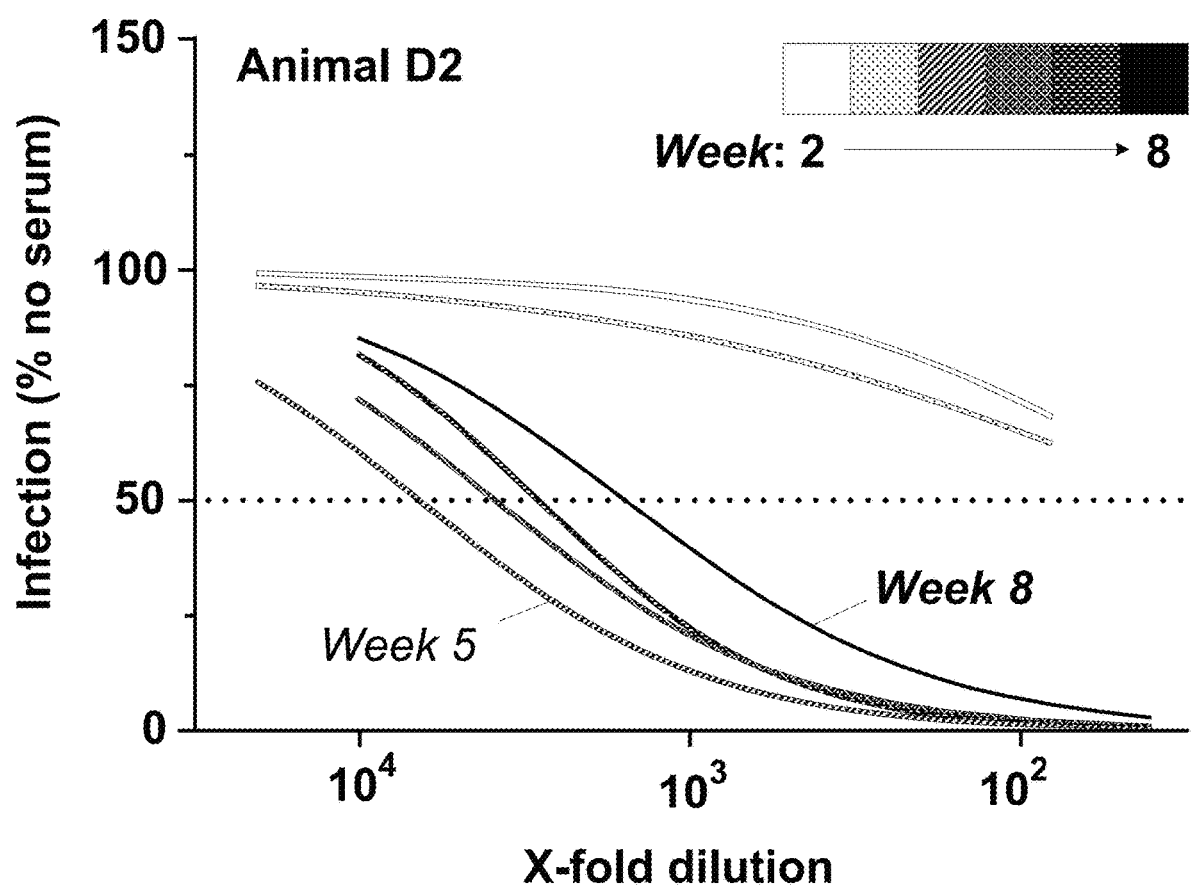
FIG. 10. A reporter virus particle (RVP/pseudovirus) assay tests inhibition of infection by pseudotyped lentiviral particles bearing the SARS-CoV-2 spike by various dilutions of sera. Curves are then generated and the neutralizing titer 50 (NT50) read as the dilution of serum required to obtain 50% inhibition. In this example vaccination leads to high neutralizing titers beginning at week 5 post priming.
Figure 11:
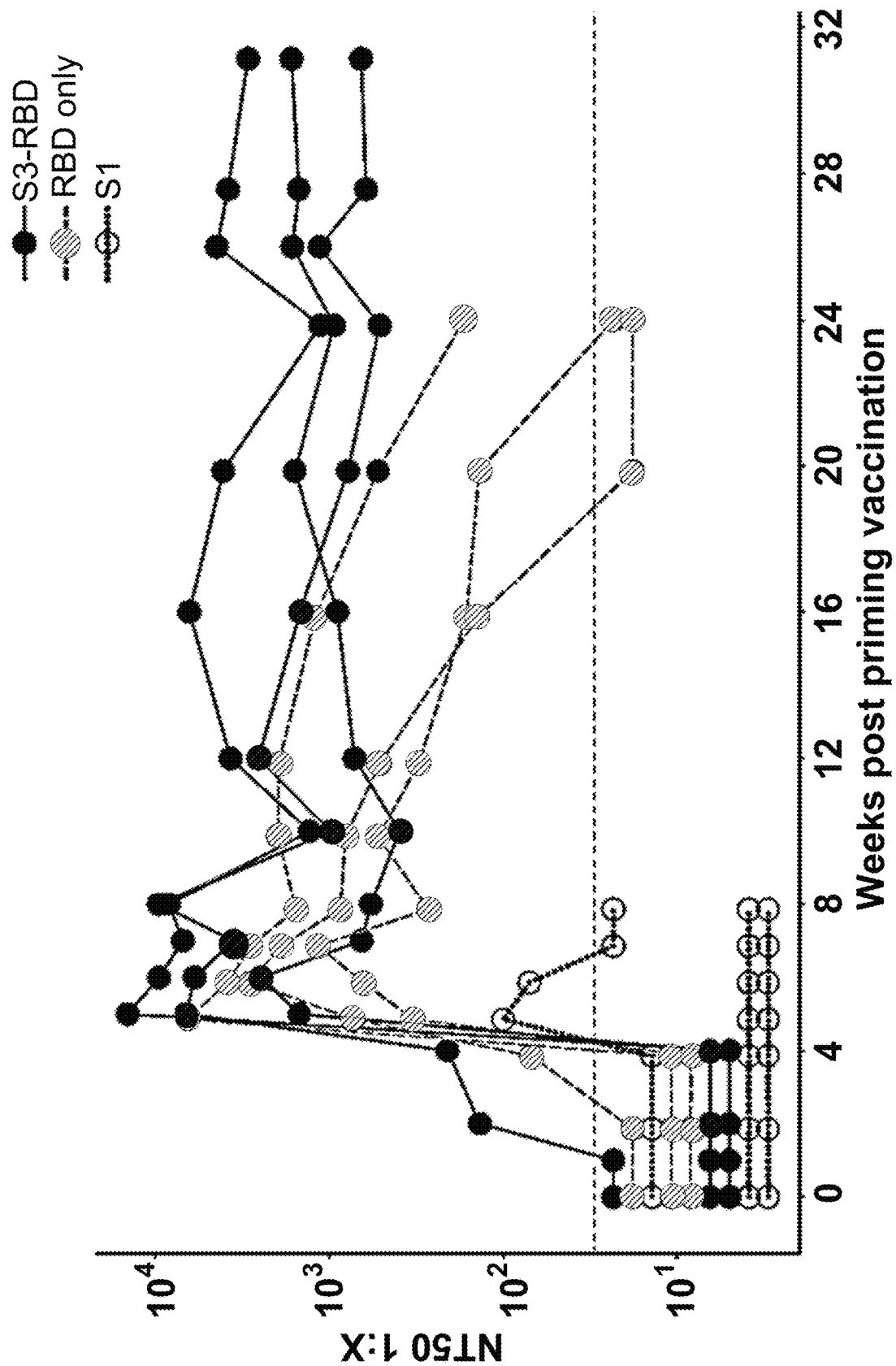
FIG. 11. Longitudinal pseudovirus neutralizing assays results demonstrate superior induction of neutralizing antibodies by s3-RBD (black solid traces). At week 5 after priming vaccination the geometric mean titer (GMT) is at least four-fold higher in the s3-RBD group than in the RBD group (solid black vs. dashed gray lines). One animal in the s3-RBD group generated a neutralizing antibody titer exceeding the upper limit of the assay, so the true advantage of s3-RBD is greater. Furthermore, most recipients of RBD alone have a neutralizing antibody titer below the limit of detection by 24 weeks post vaccination, while all s3-RBD recipients maintain high neutralizing titers through 32 weeks.

Neutralizing activity was tested against pseudotyped lentiviral particles, which are lentiviral particles lacking their native envelope proteins but bearing SARS-CoV-2 spike protein instead. Examples of the curves generated are shown in FIG. 10 for one animal. The neutralizing titer 50 (NT50) is taken for each curve as the dilution at which infection is reduced to 50%. In FIG. 10, no NT50 is detected at the first two time points but sera from all subsequent time points demonstrate neutralization by reducing infectivity of the pseudotyped particles below 50%. All RBD vaccine recipients manifested neutralizing titers in the pseudovirus assay, with animal D2 having a peak titer of 1:6539 (FIG. 11), which is approximately the 90th percentile of convalescent people (Moore and Klasse, 2020). As in the ELISA assay for binding antibody, however, recipients of the s3-RBD-expressing genetic vaccine achieved the highest neutralizing titers, which in 2 of 3 cases exceeded all RBD-recipient animals, at most time points after the fourth week (FIG. 11). Indeed, the geometric mean titer in s3-RBD-recipient animals exceeded that in RBD recipients by at least 4 fold. The actual fold increase is higher because one s3-RBD-recipient animal generated antibodies at a titer exceeding maximum that was quantifiable in the assay (1:10240). The neutralizing antibody response in s3-RBD recipients also demonstrates impressive durability, with all animals maintaining neutralization through 32 weeks after the first immunization (FIG. 11). In contrast, in ⅔ recipients of RBD alone, neutralizing activity falls below the limit of detection in our assay by 24 weeks.

In some reported cases, immune responses to membrane-associated antigens (e.g., because those antigens carry a glycosylphosphatidylinositol anchor or a membrane-spanning segment) are better than immune responses to the same antigens in secreted form. We therefore created a conjugate polypeptide comprising an anti-CD3 scFv fragment, the RBD of the B.1.351 ("South African") strain of SARS-CoV-2, and a transmembrane segment from the human PDGF receptor. The resulting amino acid sequence is shown as SEQ ID NO. 25. A codon-optimized nucleic-acid sequence for this polypeptide (SEQ ID NO. 26) was synthesized and cloned into the pUC19 plasmid downstream of the EF1-alpha promoter sequence (including its first intron) and upstream of the SV40 polyadenylation sequence.

Figure 13B:
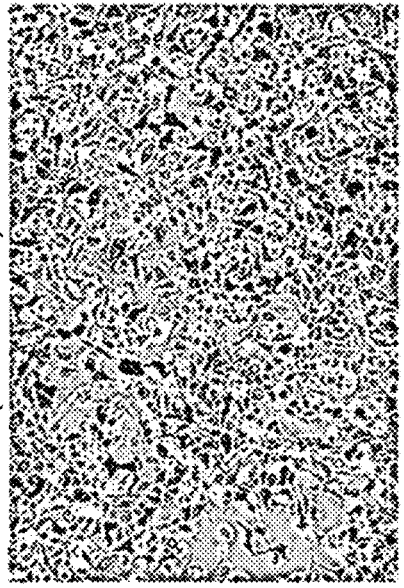
FIGS. 13A-13D. Host cells transduced with 1dCD58-RBD(B.1.351) or s3-RBD(B.1.351)-PDGFRtm produce immunoreactive RBD. This assay det methods of the present disclosure are typically desired, intended, and/or protective immune responses. The term includes the production of antibodies against an antigen, e.g., neutralizing antibodies, as well as the development, maturation, differentiation, and activation of immune cells (e.g., B cells and T cells). In some instances, an immune response comprises increasing the number or activation of MHC class E and/or class II restricted CD4$^+$ and/or CD8$^+$ T cells (e.g., in a subject). The term also includes increasing or decreasing the expression or activity of cytokines that are involved in regulating immune function. As another non-limiting example, an immune response can comprise increasing the expression or activity of interferon-gamma and/or tumor necrosis factor-alpha (e.g., in a subject).
Figure 13D:
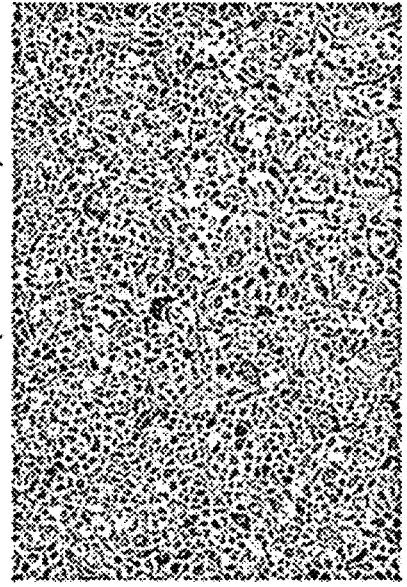
Figure 13A:
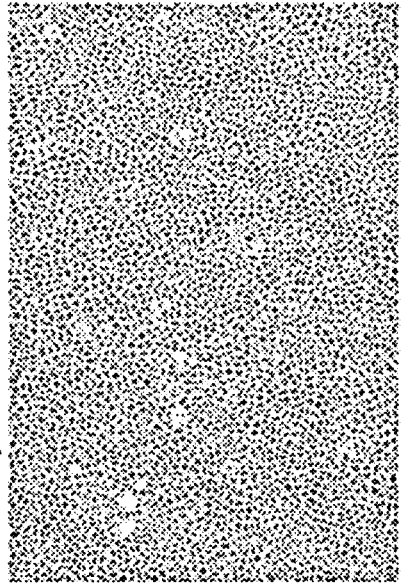

We next verified that the s3-RBD(B.1.351)-PDGFRtm conjugate polypeptide (SEQ ID NO. 25) contains immunoreactive RBD(B.1.351) when expressed in human cells, which is presumably required for induction of an anti-RBD (B.1.351) antibody response in human subjects. The plasmid encoding s3-RBD(B.1.351)-PDGFRtm was transfected into the human embryonic kidney cell line, 293, and presence of immunoreactive RBD(B.1.351) protein in the cells was verified two days later by antibody staining using the following procedure. On assay day −1, 350,000 cells per well were seeded in 6-well plates. On day 0, polyethyleneimine (PEI) transfection mix was prepared by addition of 150 microliters 0.1 mg/ml PEI in DMEM to 3 mcg DNA in an equal volume of DMEM; the mix was incubated for 20 minutes at room temperature; 2.7 ml of complete medium were added; the medium with complexed DNA was added to washed 293 cells in 6-well plates; and the plates were returned to the incubator for overnight incubation. On day 1, the transfection mix was removed from cells, the cells washed, and 2 ml fresh medium were added. On day 2, the cells were fixed with 5% PFA, washed in buffer containing 0.05% Triton X-100 to permeabilize, incubated with anti-RBD primary antibody for 2 hours, washed again, incubated with HRP-conjugated secondary antibody for 2 hours, washed, incubated with TrueBlue HRP substrate for 5-15 minutes, and finally quenched in water. The result (FIG. 13D) demonstrates that the s3-RBD(B.1.351)-PDGFRtm construct successfully produces the conjugate polypeptide including immunoreactive RBD(B.1.351).

Example 9. A Conjugate Polypeptide Vaccine Comprising the SARS-CoV-2 RBD Domain Linked to an Anti-CD3 Single-Chain Variable Fragment and an Antibody Fc Region Multivalent antigen display can drive stronger, longer-lasting antibody responses through efficient cross-linking of B-cell receptors (BCRs) and improved antigen trafficking, endocytic uptake, and eventually presentation (Brinkkemper Vaccines 7, 2019; Tokatlian Science 363:649, 2019). Repetitive epitopes both have higher effective avidity for BCRs and can cross-link the receptors, effectively activating B-cells (Cimica Clin Immunol 183:99, 2017; Zabel J Immunol 192:5499, 2014). Spacing of 5-10 nm of 15-20 hapten molecules is ideal for B-cell activation (Vogelstein PNAS 79:395, 1982). Multimeric antigens are most commonly produced ex vivo, as protein, but can also be produced by a genetic vaccine in vivo.

One method for improving the immunogenicity of vaccine antigens, for example, is to present them on nanoparticles (NPs) of 25-50 nm diameter. The licensed human papillomavirus and HBsAg vaccines involve NPs, as do efforts to create influenza and respiratory syncytial virus (RSV) vaccines (Darricarrere J Virol 92, 2018; Hsia Nature 535:136, 2016; Kanekiyo Nat Immunol 20:362, 2019; Marcandalli Cell 176:1420, 2019). Studies in animals have shown that NP presentation, compared with the delivery of the same antigens as soluble proteins, substantially improves the quantity and quality of Ab responses (Brinkkemper Vaccines 7, 2019). Thus, NP display of RSV antigens enhanced NAb titers over 10-fold (Marcandalli Cell 176: 1420, 2019). NP presentation also allows the creation of multivalent, antigenically mosaic immunogens, which can improve NAb breadth by increasing the avidity of interactions specifically with the most cross-reactive BCRs, as shown for influenza HA (Kanekiyo Nat Immunol 20:362, 2019).

The immunoglobulin "fragment crystallizable" or Fc is a dimerizing molecule; therefore, when an immunogen is expressed as a fusion protein with Fc the result is dimeric molecule likely to have greater immunogenicity for the reasons given above. Fc regions can also be modified to polymerize into well-defined complexes containing twelve fused partners (Mekhaiel Sci Rep 1:124). Furthermore, the presence of an Fc domain markedly increases the plasma half-life of a fusion protein, owing to its interaction with the salvage neonatal Fc-receptor, as well as to the slower renal clearance for larger molecules (Roopenian & Akilesh, 2007 and Kontermann, 2011). The attached Fc domain also enables these molecules to interact with Fc-receptors (FcRs) found on immune cells, a feature that is particularly important for their use in oncological therapies and vaccines (Nimmerjahn & Ravetch, 2008).

To allow expression of multimeric s3-RBD and to achieve other benefits conferred by the Fc domain, we therefore designed a protein molecule consisting of the conjugate polypeptide vaccine, s3-RBD, fused at its C-terminus to the human IgG1 Fc domain, termed "s3-RBD-Fc" (SEQ ID NO. 9). We next prepared a codon-optimized ORF capable of expressing s3-RBD-Fc (SEQ ID NO. 10).

To test the immunogenicity of s3-RBD-Fc, this ORF is engineered into an expression cassette that is transferred into appropriate DNA and adenoviral vectors, which are administered to rhesus macaques.

Example 10. A Dimerizing Conjugate Polypeptide Vaccine Comprising the SARS-CoV-2 RBD Domain Linked to an Anti-CD3 Single-Chain Variable Fragment Forming a Diabody s3-RBD comprises an anti-CD3 scFv fragment, which itself comprises the heavy- and light-chain variable regions, VH and VL, from the monoclonal antibody SP34. To form a functional monomeric scFv fragment, these VH and VL regions are separated by a flexible linker that is needed to allow the two domains to achieve the proper three-dimensional configuration needed for CD3 binding. To allow proper folding of monomeric scFv, the linker length is conventionally >12 amino acids and most often 15 amino acids (Wang Antibodies 8:43, 2019).

Shorter linkers joining the two variable domains can dictate the formation of multimeric scFv molecules, because the shorter linkers have insufficient length to permit folding of a monomer with VH and VL regions correctly related in space. Reduction of the length of the linker joining the two variable domains to below 8-12 residues favours dimeric assembly of the VH-VL fragments, generating diabodies with two antigen-binding sites (Holliger et al., 1993; Kortt et al., 1994; Aflthan et al., 1995). Further reduction of the linker sequence to less than five amino acids has been shown to result in the generation of tri- or tetrameric molecules (triabodies, tetrabodies) (Iliades et al., 1997; Kortt et al., 1997; Pei et al., 1997; Le Gall et al., 1999; Dolezal et al., 2000; Hudson and Kortt, 1999).

We therefore designed a dimerizing form of s3-RBD by reducing the length of the VH-VL linker to five amino acids (SEQ ID NO. 11). We prepared a codon-optimized ORF that codes for this dimerizing form of the conjugate polypeptide immunogen (SEQ ID NO. 12). This codon-optimized ORF is engineered successively into an expression cassette and into DNA and adenoviral vectors, which are administered to animals for immunogenicity testing.

In evaluating the reported crystal structures of diabodies, significant structural diversity was evident, suggesting instability of the diabody structure (Kim Sci Rep 6:34515, 2016). In the crystal structures of diabodies, the light chains do not contribute to the interaction between the Fv domains and the two heavy chains form a relatively small interaction interface. In order to use diabodies as general and reliable mediators of artificial protein assemblies, it was proposed that predictable orientation and distance between the antigen-binding sites (e.g., CD3-binding sites) would be advantageous. Nonetheless, many diabodies of the simplest design, i.e., with a linker sequence reduced to five amino acids, had interaction interfaces between the Fv domains that appeared to be too small to have stable structures (Moraga Cell 160:1196, 2015; Perisic Structure 2:1217, 1994). It was shown that diabody structure could be made more rigid and predictable by substitution of an arginine residue in the EF loop and introduction of one or more disulfide bridges between the Fv domains.

We next designed a dimerizing form of s3-RBD with greater predicted stability by reducing the length of the VH-VL linker to five amino acids, substituting a positively charged lysine residue in the EF loop, and introduction of a cysteine residue that can form a disulfide bridge (SEQ ID NO. 13). We prepared a codon-optimized ORF that codes for this dimerizing form of the conjugate polypeptide immunogen having enhanced stability (SEQ ID NO. 14). This codon-optimized ORF is engineered successively into an expression cassette and into DNA and adenoviral vectors, which are administered to animals for immunogenicity testing.

Figure 12:
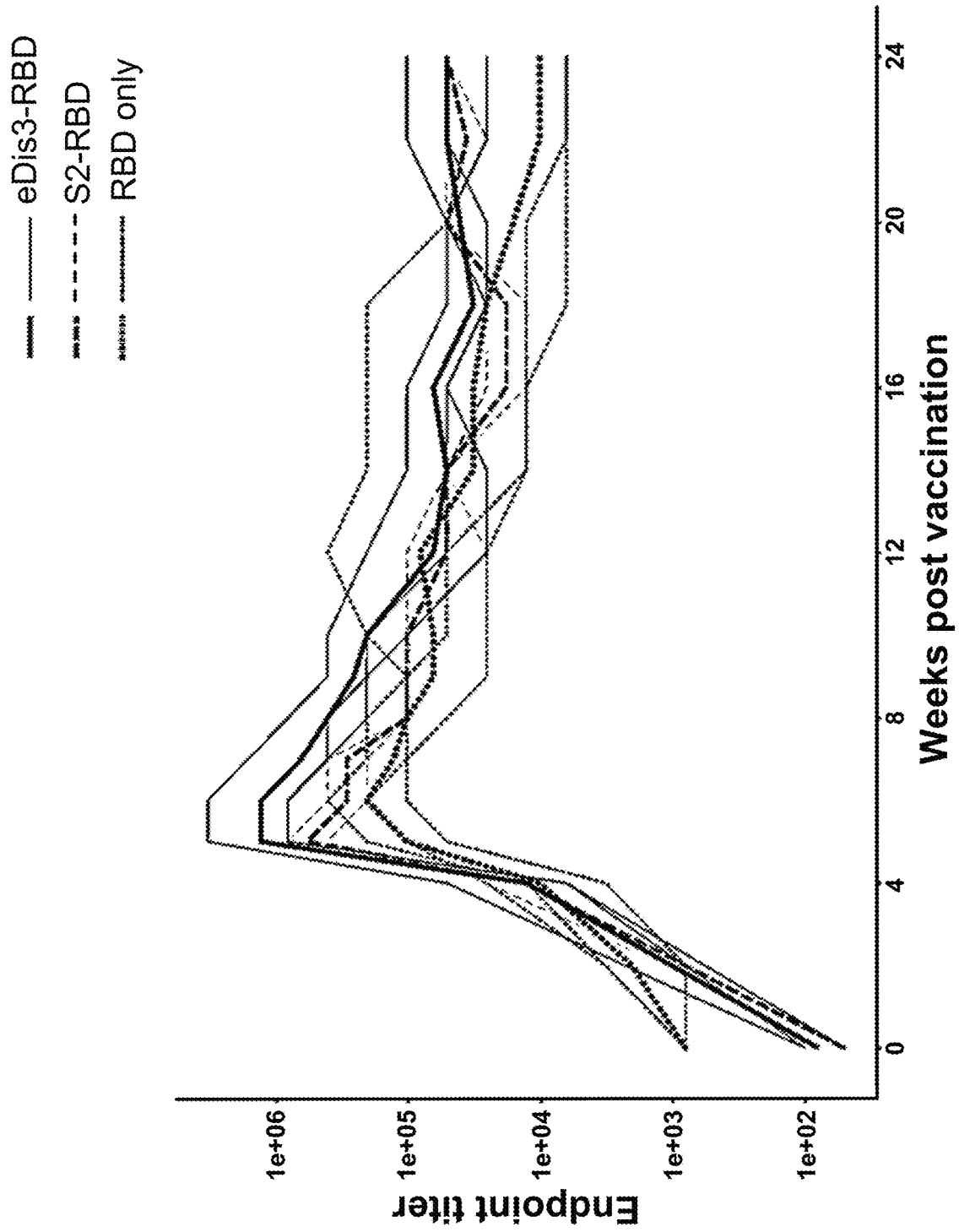
FIG. 12. Binding antibodies detected by endpoint-dilution ELISA assay in macaques primed using RBD alone, s2-RBD (i.e., antiCD2-RBD conjugate polypeptide), or eDis3-RBD (enhanced diabody antiCD3-RBD conjugate polypeptide). Responses of individual vaccinated macaques are shown with thinner lines; geometric mean responses by group are shown with thicker lines (RBD in dotted black, s2-RBD in dashed gray, eDis3-RBD in solid black). As compared to RBD alone, recipients of either s2-RBD or eDis3-RBD priming exhibit superior responses that reach a higher peak and are maintained at a higher level after 24 weeks.

The plasmid DNA molecule coding for the enhanced dimerizing antiCD3-RBD conjugate polypeptide, also called eDis3-RBD, was administered to three rhesus macaques as a DNA vaccine (by electroporation of 1 mg of DNA at day 0); boosting immunization was provided at day 28 with a type-35 adenovector coding for RBD alone (FIG. 12). Antibody responses in these macaques were compared those obtained using RBD alone for priming and boosting. The results demonstrate both improved peak antibody responses using eDis3-RBD (6.3-fold increase in geometric mean) and increased durable antibody responses remaining 24 weeks after vaccination (5-fold increase in geometric mean; FIG.

12, compare solid black average line for eDis3-RBD to dotted black average line for RBD alone).

Example 11. A Conjugate Polypeptide Vaccine Comprising the SARS-CoV-2 RBD Domain Linked to an Anti-CD2 Single-Chain Variable Fragment CD2 is an adhesion molecule found on the surface of T cells and natural killer (NK) cells. CD2 binds to other adhesion molecules expressed on the surface of other cells, including LFA-3 (CD58). CD2 functions as a co-stimulatory molecule, which means that signals sent via CD2 cooperate with those sent by TCR engagement to induce cell proliferation and cytokine production in resting T cells. A close association of CD2 with the CD3-TCR complex appears to be essential for optimal T-cell responses. CD2 is also an important adhesive molecule, which binds to LFA-3 and thereby causes antigen-independent cell adhesion, expansion of naïve T helper cells, and induction of IFN-gamma production in memory cells. In addition to LFA-3, CD2 can interact with CD48 and CD59.

We created a conjugate polypeptide comprising the RBD of SARS-CoV-2 spike and a CD2-binding polypeptide by fusing coding sequences for the following protein elements: tissue plasminogen activator signal sequence (to permit secretion of the conjugate polypeptide from the cell), an anti-CD2 scFv derived from the rat anti-CD2 antibody, LO-CD2a (see, e.g., U.S. Pat. No. 6,849,258); a flexible linker; and SARS-CoV-2 RBD (codon optimized). The resulting amino acid sequence is shown as SEQ ID NO. 15. A codon-optimized nucleic-acid sequence for this polypeptide (SEQ ID NO. 16) is synthesized and cloned into the pUC19 plasmid downstream of the EF1-alpha promoter sequence (including its first intron) and upstream of the SV40 polyadenylation sequence.

The plasmid DNA molecule coding for antiCD2-RBD conjugate polypeptide, also called s2-RBD, was administered to two rhesus macaques as a DNA vaccine (by electroporation of 1 mg of DNA at day 0); boosting immunization was provided at day 28 with a type-35 adenovector coding for RBD alone (FIG. 12). Antibody responses in these macaques were compared those obtained using RBD alone for priming and boosting. The results demonstrate both improved peak antibody responses using s2-RBD (2.8-fold increase in geometric mean) and increased durable antibody responses remaining 24 weeks after vaccination (5-fold increase in geometric mean; FIG. 12, compare dashed gray average line for s2-RBD to dotted black average line for RBD alone).

Example 12. A Dimerizing Conjugate Polypeptide Vaccine Comprising the SARS-CoV-2 RBD Domain Linked to an Anti-CD2 Single-Chain Variable Fragment Forming a Diabody A dimerizing form of anti-CD2 scFv-RBD was designed by reducing the length of the VH-VL linker to five amino acids (SEQ ID NO. 17). We prepared a codon-optimized ORF that codes for this dimerizing form of the conjugate polypeptide immunogen (SEQ ID NO. 18). This codon-optimized ORF is engineered successively into an expression cassette and into DNA and adenoviral vectors, which are administered to animals for immunogenicity testing.

We next designed a dimerizing form of anti-CD2 scFv-RBD with greater predicted stability by reducing the length of the VH-VL linker to five amino acids and introducing a cysteine residue that can form a disulfide bridge (SEQ ID NO. 19). The anti-CD2 scFv used in this construct does not have a positively charged residue at the critical position in the EF loop that is predicted to cause instability. We prepared a codon-optimized ORF that codes for this enhanced-stability, dimerizing form of anti-CD2 scFv-RBD (SEQ ID NO. 20). This codon-optimized ORF is engineered successively into an expression cassette and into DNA and adenoviral vectors, which are administered to animals for immunogenicity testing.

Example 13. A Conjugate Polypeptide Vaccine Comprising the SARS-CoV-2 RBD Domain Linked to the N-Terminal Domain of LFA-3, which Binds to CD2

Conjugate polypeptide immunogens for delivery in genetic vaccines can be designed using any protein sequence that will bind to an appropriate cell-surface receptor in the vaccine recipient. The 179-residue ectodomain of human CD58 consists of two extracellular immunoglobulin-like domains anchored to the membrane through either a transmembrane segment or a glycosyl phosphatidylinositol (GPI) linker (Dustin et al., 1987b; Wallich et al., 1998). The 95 residue membrane-distal N-terminal domain of CD58 (1dCD58) is entirely responsible for the adhesion to CD2 (Sun et al.).

We created a conjugate polypeptide comprising the RBD of SARS-CoV-2 spike and a CD2-binding polypeptide by fusing coding sequences for the following protein elements: tissue plasminogen activator signal sequence (to permit secretion of the conjugate polypeptide from the cell), the first extracellular domain of human CD58, 1dCD58; a flexible linker; and SARS-CoV-2 RBD (codon optimized). The resulting amino acid sequence is shown as SEQ ID NO. 21. A codon-optimized nucleic-acid sequence for this polypeptide (SEQ ID NO. 22) is synthesized and cloned into the pUC19 plasmid downstream of the EF1-alpha promoter sequence (including its first intron) and upstream of the SV40 polyadenylation sequence.

We also created a conjugate polypeptide comprising the RBD of the B.1.351 ("South African") strain SARS-CoV-2 and a CD2-binding polypeptide by fusing coding sequences for tissue plasminogen activator signal sequence, 1dCD58, a flexible linker, and SARS-CoV-2 RBD(B.1.351) (i.e., RBD from SARS-CoV-2 strain B.1.351). The resulting amino acid sequence is shown as SEQ ID NO. 23. A codon-optimized nucleic-acid sequence for this polypeptide (SEQ ID NO. 24) is synthesized and cloned into the pUC19 plasmid downstream of the EF1-alpha promoter sequence (including its first intron) and upstream of the SV40 polyadenylation sequence.

Figure 13C:
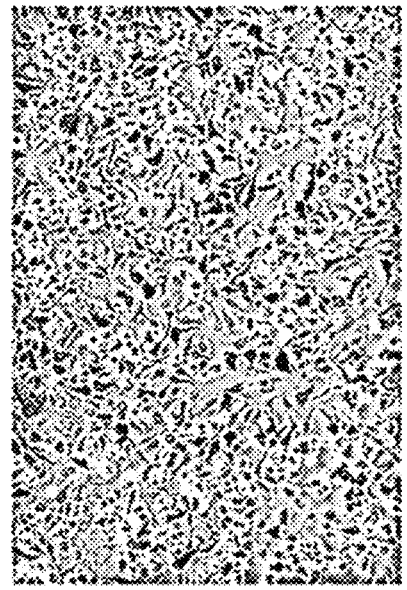

We next verified that the 1dCD58-RBD(B.1.351) conjugate polypeptide (SEQ ID NO. 23) contains immunoreactive RBD(B.1.351) when expressed in human cells, which is presumably required for induction of an anti-RBD(B.1.351) antibody response in human subjects. The plasmid encoding 1dCD58-RBD(B.1.351) was transfected into the human embryonic kidney cell line, 293, and the presence of immunoreactive RBD(B.1.351) protein in the cells was verified two days later by antibody staining using the following procedure. On assay day −1, 350,000 cells per well were seeded in 6-well plates. On day 0, polyethyleneimine (PEI) transfection mix was prepared by addition of 150 microliters 0.1 mg/ml PEI in DMEM to 3 mcg DNA in an equal volume of DMEM; the mix was incubated for 20 minutes at room temperature; 2.7 ml of complete medium were added; the medium with complexed DNA was added to washed 293 cells in 6-well plates; and the plates were returned to the incubator for overnight incubation. On day 1, the transfection mix was removed from cells, the cells washed, and 2 ml fresh medium were added. On day 2, the cells were fixed with 5% PFA, washed in buffer containing 0.05% Triton X-100 to permeabilize, incubated with anti-RBD primary antibody for 2 hours, washed again, incubated with HRP-conjugated secondary antibody for 2 hours, washed, incubated with TrueBlue HRP substrate for 5-15 minutes, and finally quenched in water. The result (FIG. 13C) demonstrates that the 1dCD58-RBD(B.1.351) construct successfully produces the conjugate polypeptide including immunoreactive RBD(B.1.351).

Example 14. A Conjugate Polypeptide Vaccine Comprising the SARS-CoV-2 RBD Domain Linked to an Anti-CD4 Single-Chain Variable Fragment CD4 is a glycoprotein found on the surface of helper T cells, as well as some monocytes, macrophages, and dendritic cells. As a member of the immunoglobulin superfamily, it comprises four immunoglobulin domains, known as $D_1$ to $D_4$, exposed on the surface of the cell. The $D_1$ domain contributes to an interaction with the beta$_2$ domain of MHC class II molecules that defines much of the biology of helper T cells, which respond to peptides presented on MEW class II molecules by antigen-presenting cells. CD4 is also the primary entry receptor for the HIV-1 envelope glycoprotein.

We created a conjugate polypeptide comprising the RBD of SARS-CoV-2 spike and a CD4-binding polypeptide by fusing coding sequences for the following protein elements: tissue plasminogen activator signal sequence (to permit secretion of the conjugate polypeptide from the cell); an anti-CD4 scFv derived from the humanized mouse anti-CD4 antibody, hu5A8 (see, e.g., AIDS Res Hum Retro 13:933); a flexible linker; and SARS-CoV-2 RBD (codon optimized). The resulting amino acid sequence is shown as SEQ ID NO. 27. A codon-optimized nucleic-acid sequence for this polypeptide (SEQ ID NO. 28) is synthesized and cloned into the pUC19 plasmid downstream of the EF1-alpha promoter sequence (including its first intron) and upstream of the SV40 polyadenylation sequence.

REFERENCES FOR EXAMPLES 1-7

1. De Groot, A. S., L. Einck, L. Moise, M. Chambers, J. Ballantyne, R. W. Malone, M. Ardito, and W. Martin, Making vaccines "on demand": a potential solution for emerging pathogens and biodefense? Hum Vaccin Immunother, 2013. 9(9): p. 1877-84.
2. Ma, C., L. Wang, X. Tao, N. Zhang, Y. Yang, C. K. Tseng, F. Li, Y. Zhou, et al., Searching for an ideal vaccine candidate among different MERS coronavirus receptor-binding fragments—the importance of immunofocusing in subunit vaccine design. Vaccine, 2014. 32(46): p. 6170-6176.
3. Sui, J., M. Deming, B. Rockx, R. C. Liddington, Q. K. Zhu, R. S. Buie, and W. A. Marasco, Effects of human anti-spike protein receptor binding domain antibodies on severe acute respiratory syndrome coronavirus neutralization escape and fitness. J Virol, 2014. 88(23): p. 13769-80.
4. Katzelnick, L. C., L. Gresh, M. E. Halloran, J. C. Mercado, G. Kuan, A. Gordon, A. Balmaseda, and E. Harris, Antibody-dependent enhancement of severe dengue disease in humans. Science, 2017. 358(6365): p. 929-932.
5. Haagmans, B. L., J. M. van den Brand, V. S. Raj, A. Volz, P. Wohlsein, S. L. Smits, D. Schipper, T. M. Bestebroer, et al., An orthopoxvirus-based vaccine reduces virus excretion after MERS-CoV infection in dromedary camels. Science, 2016. 351(6268): p. 77-81.
6. Jaume, M., M. S. Yip, Y. W. Kam, C. Y. Cheung, F. Kien, A. Roberts, P. H. Li, I. Dutry, et al., SARS CoV subunit vaccine: antibody-mediated neutralisation and enhancement. Hong Kong Med J, 2012. 18 Suppl 2: p. 31-6.
7. Wang, S. F., S. P. Tseng, C. H. Yen, J. Y. Yang, C. H. Tsao, C. W. Shen, K. H. Chen, F. T. Liu, et al., Antibody-dependent SARS coronavirus infection is mediated by antibodies against spike proteins. Biochem Biophys Res Commun, 2014. 451(2): p. 208-14.
8. Czub, M., H. Weingartl, S. Czub, R. He, and J. Cao, Evaluation of modified vaccinia virus Ankara based recombinant SARS vaccine in ferrets. Vaccine, 2005. 23(17-18): p. 2273-9.
9. Weingartl, H., M. Czub, S. Czub, J. Neufeld, P. Marszal, J. Gren, G. Smith, S. Jones, et al., Immunization with modified vaccinia virus Ankara-based recombinant vaccine against severe acute respiratory syndrome is associated with enhanced hepatitis in ferrets. J Virol, 2004. 78(22): p. 12672-6.
10. Zhao, J., K. Li, C. Wohlford-Lenane, S. S. Agnihothram, C. Fett, J. Zhao, M. J. Gale, Jr., R. S. Baric, et al., Rapid generation of a mouse model for Middle East respiratory syndrome. Proc Natl Acad Sci USA, 2014. 111(13): p. 4970-5.
11. Zhao, J., J. Zhao, A. K. Mangalam, R. Channappanavar, C. Fett, D. K. Meyerholz, S. Agnihothram, R. S. Baric, et al., Airway Memory CD4(+) T Cells Mediate Protective Immunity against Emerging Respiratory Coronaviruses. Immunity, 2016. 44(6): p. 1379-91.
12. Hansen, S. G., C. Vieville, N. Whizin, L. Coyne-Johnson, D. C. Siess, D. D. Drummond, A. W. Legasse, M. K. Axthelm, et al., Effector memory T cell responses are associated with protection of rhesus monkeys from mucosal simian immunodeficiency virus challenge. Nat Med, 2009. 15(3): p. 293-9.
13. Tang, F., Y. Quan, Z. T. Xin, J. Wrammert, M. J. Ma, H. Lv, T. B. Wang, H. Yang, et al., Lack of peripheral memory B cell responses in recovered patients with severe acute respiratory syndrome: a six-year follow-up study. J Immunol, 2011. 186(12): p. 7264-8.
14. Picker, L. J., E. F. Reed-Inderbitzin, S. I. Hagen, J. B. Edgar, S. G. Hansen, A. Legasse, S. Planer, M. Piatak, Jr., et al., IL-15 induces CD4 effector memory T cell production and tissue emigration in nonhuman primates. J Clin Invest, 2006. 116(6): p. 1514-24.
15. Casazza, J. P., M. R. Betts, D. A. Price, M. L. Precopio, L. E. Ruff, J. M. Brenchley, B. J. Hill, M. Roederer, et al., Acquisition of direct antiviral effector functions by CMV-specific CD4+ T lymphocytes with cellular maturation. J Exp Med, 2006. 203(13): p. 2865-77.
16. Chan, K. S. and A. Kaur, Flow cytometric detection of degranulation reveals phenotypic heterogeneity of degranulating CMV-specific CD8+ T lymphocytes in rhesus macaques. J Immunol Methods, 2007. 325(1-2): p. 20-34.
17. Kern, F., E. Khatamzas, I. Surel, C. Frommel, P. Reinke, S. L. Waldrop, L. J. Picker, and H. D. Volk, Distribution of human CMV-specific memory T cells among the CD8pos. subsets defined by CD57, CD27, and CD45 isoforms. Eur J Immunol, 1999. 29(9): p. 2908-15.
18. Pitcher, C. J., S. I. Hagen, J. M. Walker, R. Lum, B. L. Mitchell, V. C. Maino, M. K. Axthelm, and L. J. Picker, Development and homeostasis of T cell memory in rhesus macaque. J Immunol, 2002. 168(1): p. 29-43.
19. Sylwester, A. W., B. L. Mitchell, J. B. Edgar, C. Taormina, C. Pelte, F. Ruchti, P. R. Sleath, K. H. Grabstein, et al., Broadly targeted human cytomegalovirus-specific CD4+ and CD8+ T cells dominate the memory compartments of exposed subjects. J Exp Med, 2005. 202(5): p. 673-85.
20. Hansen, S. G., J. B. Sacha, C. M. Hughes, J. C. Ford, B. J. Burwitz, I. Scholz, R. M. Gilbride, M. S. Lewis, et al., Cytomegalovirus vectors violate CD8+ T cell epitope recognition paradigms. Science, 2013. 340(6135): p. 1237874.
21. Marzi, A., A. A. Murphy, F. Feldmann, C. J. Parkins, E. Haddock, P. W. Hanley, M. J. Emery, F. Engelmann, et al., Cytomegalovirus-based vaccine expressing Ebola virus glycoprotein protects nonhuman primates from Ebola virus infection. Sci Rep, 2016. 6: p. 21674.
22. Sequar, G., W. J. Britt, F. D. Lakeman, K. M. Lockridge, R. P. Tarara, D. R. Canfield, S. S. Zhou, M. B. Gardner, and P. A. Barry, Experimental coinfection of rhesus macaques with rhesus cytomegalovirus and simian immunodeficiency virus: pathogenesis. J Virol, 2002. 76(15): p. 7661-71.
23. Boppana, S. B., L. B. Rivera, K. B. Fowler, M. Mach, and W. J. Britt, Intrauterine transmission of cytomegalovirus to infants of women with preconceptional immunity. N Engl J Med, 2001. 344(18): p. 1366-71.
24. Hansen, S. G., C. J. Powers, R. Richards, A. B. Ventura, J. C. Ford, D. Siess, M. K. Axthelm, J. A. Nelson, et al., Evasion of CD8+ T cells is critical for superinfection by cytomegalovirus. Science, 2010. 328(5974): p. 102-6.
25. Hansen, S. G., D. E. Zak, G. Xu, J. C. Ford, E. E. Marshall, D. Malouli, R. M. Gilbride, C. M. Hughes, et al., Prevention of tuberculosis in rhesus macaques by a cytomegalovirus-based vaccine. Nat Med, 2018. 24(2): p. 130-143.
26. Hansen, S. G., M. Piatak, Jr., A. B. Ventura, C. M. Hughes, R. M. Gilbride, J. C. Ford, K. Oswald, R. Shoemaker, et al., Immune clearance of highly pathogenic SIV infection. Nature, 2013. 502(7469): p. 100-4.
27. Hansen, S. G., E. E. Marshall, D. Malouli, A. B. Ventura, C. M. Hughes, E. Ainslie, J. C. Ford, D. Morrow, et al., A live-attenuated RhCMV/SIV vaccine shows long-term efficacy against heterologous SIV challenge. Sci Transl Med, 2019. 11(501).
28. Hansen, S. G., J. C. Ford, M. S. Lewis, A. B. Ventura, C. M. Hughes, L. Coyne-Johnson, N. Whizin, K. Oswald, et al., Profound early control of highly pathogenic SIV by an effector memory T-cell vaccine. Nature, 2011. 473 (7348): p. 523-7.
29. Knipe, D. M. and P. M. Howley, Fields virology. 6th ed. 2013, Philadelphia, PA: Wolters Kluwer/Lippincott Williams & Wilkins Health. 2 volumes.
30. Asher, D. M., C. J. Gibbs, Jr., and D. J. Lang, Rhesus monkey cytomegaloviruses: persistent asymptomatic viruses. Bacteriol. Proc., 1969. 69: p. 191.
31. Asher, D. M., C. J. Gibbs, Jr., D. J. Lang, D. C. Gajdusek, and R. M. Chanock, Persistent shedding of cytomegalovirus in the urine of healthy Rhesus monkeys. Proc Soc Exp Biol Med, 1974. 145(3): p. 794-801.
32. Oxford, K. L., L. Strelow, Y. Yue, W. L. Chang, K. A. Schmidt, D. J. Diamond, and P. A. Barry, Open reading frames carried on UL/b' are implicated in shedding and horizontal transmission of rhesus cytomegalovirus in rhesus monkeys. J Virol, 2011. 85(10): p. 5105-14.
33. Cha, T., E. Tom, G. Kemble, G. Duke, E. Mocarski, and R. Spaete, Human cytomegalovirus clinical isolates carry at least 19 genes not found in laboratory strains. J Virol, 1996. 70(1): p. 78-83.
34. Dolan, A., C. Cunningham, R. D. Hector, A. F. Hassan-Walker, L. Lee, C. Addison, D. J. Dargan, D. J. McGeoch, et al., Genetic content of wild-type human cytomegalovirus. J Gen Virol, 2004. 85(Pt 5): p. 1301-12.
35. Oxford, K. L., M. K. Eberhardt, K. W. Yang, L. Strelow, S. Kelly, S. S. Zhou, and P. A. Barry, Protein coding content of the UL/b' region of wild-type rhesus cytomegalovirus. Virology, 2008. 373(1): p. 181-8.
36. Malouli, D., E. S. Nakayasu, K. Viswanathan, D. G. Camp, 2nd, W. L. Chang, P. A. Barry, R. D. Smith, and K. Fruh, Reevaluation of the coding potential and proteomic analysis of the BAC-derived rhesus cytomegalovirus strain 68-1. J Virol, 2012. 86(17): p. 8959-73.
37. Huang, E. S., S. M. Huong, G. E. Tegtmeier, and C. Alford, Cytomegalovirus: genetic variation of viral genomes. Ann N Y Acad Sci, 1980. 354: p. 332-46.
38. Renzette, N., L. Gibson, B. Bhattacharjee, D. Fisher, M. R. Schleiss, J. D. Jensen, and T. F. Kowalik, Rapid intrahost evolution of human cytomegalovirus is shaped by demography and positive selection. PLoS Genet, 2013. 9(9): p. e1003735.
39. Renzette, N., L. Gibson, J. D. Jensen, and T. F. Kowalik, Human cytomegalovirus intrahost evolution—a new avenue for understanding and controlling herpesvirus infections. Curr Opin Virol, 2014. 8: p. 109-15.
40. Cunningham, C., D. Gatherer, B. Hilfrich, K. Baluchova, D. J. Dargan, M. Thomson, P. D. Griffiths, G. W. Wilkinson, et al., Sequences of complete human cytomegalovirus genomes from infected cell cultures and clinical specimens. J Gen Virol, 2010. 91(Pt 3): p. 605-15.
41. Marshall, G. S. and S. A. Plotkin, Progress toward developing a cytomegalovirus vaccine. Infect Dis Clin North Am, 1990. 4(2): p. 283-98.
42. Hansen, S. G., H. L. Wu, B. J. Burwitz, C. M. Hughes, K. B. Hammond, A. B. Ventura, J. S. Reed, R. M. Gilbride, et al., Broadly targeted CD8(+) T cell responses restricted by major histocompatibility complex E. Science, 2016. 351(6274): p. 714-20.
43. Zhao, G., L. Du, C. Ma, Y. Li, L. Li, V. K. Poon, L. Wang, F. Yu, et al., A safe and convenient pseudovirus-based inhibition assay to detect neutralizing antibodies and screen for viral entry inhibitors against the novel human coronavirus MERS-CoV. Virol J, 2013. 10: p. 266.

REFERENCES FOR EXAMPLES 8-13

Moore, J. P. and P. J. Klasse, SARS-CoV-2 vaccines: 'Warp Speed' needs mind melds not warped minds. J Virol, 2020.
Brinkkemper, M. and K. Sliepen, Nanoparticle Vaccines for Inducing HIV-1 Neutralizing Antibodies. Vaccines (Basel), 2019. 7(3).
Tokatlian, T., B. J. Read, C. A. Jones, D. W. Kulp, S. Menis, J. Y. H. Chang, J. M. Steichen, S. Kumari, et al., Innate immune recognition of glycans targets HIV nanoparticle immunogens to germinal centers. Science, 2019. 363 (6427): p. 649-654.
Cimica, V. and J. M. Galarza, Adjuvant formulations for virus-like particle (VLP) based vaccines. Clin Immunol, 2017. 183: p. 99-108.
Zabel, F., D. Mohanan, J. Bessa, A. Link, A. Fettelschoss, P. Saudan, T. M. Kundig, and M. F. Bachmann, Viral particles drive rapid differentiation of memory B cells into secondary plasma cells producing increased levels of antibodies. J Immunol, 2014. 192(12): p. 5499-508.

Vogelstein, B., R. Z. Dintzis, and H. M. Dintzis, Specific cellular stimulation in the primary immune response: a quantized model. Proc Natl Acad Sci USA, 1982. 79(2): p. 395-9.

Darricarrere, N., S. Pougatcheva, X. Duan, R. S. Rudicell, T. H. Chou, J. DiNapoli, T. M. Ross, T. Alefantis, et al., Development of a Pan-H1 Influenza Vaccine. J Virol, 2018. 92(22).

Hsia, Y., J. B. Bale, S. Gonen, D. Shi, W. Sheffler, K. K. Fong, U. Nattermann, C. Xu, et al., Design of a hyperstable 60-subunit protein dodecahedron. [corrected]. Nature, 2016. 535(7610): p. 136-9.

Kanekiyo, M., M. G. Joyce, R. A. Gillespie, J. R. Gallagher, S. F. Andrews, H. M. Yassine, A. K. Wheatley, B. E. Fisher, et al., Mosaic nanoparticle display of diverse influenza virus hemagglutinins elicits broad B cell responses. Nat Immunol, 2019. 20(3): p. 362-372.

Marcandalli, J., B. Fiala, S. Ols, M. Perotti, W. de van der Schueren, J. Snijder, E. Hodge, M. Benhaim, et al., Induction of Potent Neutralizing Antibody Responses by a Designed Protein Nanoparticle Vaccine for Respiratory Syncytial Virus. Cell, 2019. 176(6): p. 1420-1431 e17.

Mekhaiel D N, Czajkowsky D M, Andersen J T, Shi J, El-Faham M, Doenhoff M, McIntosh R S, Sandlie I, He J, Hu J, et al (2011b) Polymeric human Fc-fusion proteins with modified effector functions. Sci Rep 1: 124

Roopenian D C, Akilesh S (2007) FcRn: the neonatal Fc receptor comes of age. Nat Rev Immunol 7: 715-725

Kontermann R E (2011) Strategies for extended serum half-life of protein therapeutics. Curr Opin Biotechnol 22: 868-876

Nimmerjahn F, Ravetch J V (2008) Fcgamma receptors as regulators of immune responses. Nat Rev Immunol 8: 34-47

Qiong Wang, Yiqun Chen, Jaeyoung Park, Xiao Liu, Yifeng Hu, Tiexin Wang, Kevin McFarland and Michael J. Betenbaugh (2019) Design and Production of Bispecific Antibodies. Antibodies 2019, 8, 43; doi:10.3390/antib8030043

Holliger, P., Prospero, T. D. and Winter, G. (1993) Proc. Natl Acad. Sci. USA, 90. 6444-6448.

Kortt, A. A. et al. (1994) Eur. J. Biochem., 221, 151-157.

Aflthan, K, Takkinen, K., Sizmann, D., Söderlund, H. and Teeri, T. T. (1995) Protein Eng., 8, 725-731.

Iliades, P. Kortt, A. A. and Hudson, P. J. (1997) FEBS Lett., 409, 437-441

Kortt, A. A. et al. (1997) Protein Eng., 10, 423-433.

Pei, X. Y., Holliger, P., Murzin, A. G. and Williams, R. L. (1997) Proc. Natl Acad. Sci. USA, 94, 9637-9642.

Le Gall, F., Kipriyanov, S. M., Moldenhauer, G. and Little, M. (1999) FEBS Lett., 453, 164-168.

Dolezal, O., Pearce, L. A., Lawrence, L. J., McCoy, A. J., Hudson, P. J. and Kortt, A. A. (2000) Protein Eng., 13, 565-574.

Hudson, P. J. and Kortt, A. A. (1999) J. Immunol. Methods, 231, 177-189.

Jin Hong Kim, Dong Hyun Song, Suk-Jun Youn, Ji Won Kim, Geunyoung Cho3, Sun Chang Kim4, Hayyoung Lee5, Mi Sun Jin6 & Jie-Oh Lee (2016). Crystal structures of mono- and bispecific diabodies and reduction of their structural flexibility by introduction of disulfide bridges at the Fv interface. Scientific Reports, 6:34515, DOI: 10.1038/srep34515.

Moraga, I. et al. Tuning cytokine receptor signaling by re-orienting dimer geometry with surrogate ligands. Cell 160, 1196-208 (2015).

Perisic, O., Webb, P. A., Holliger, P., Winter, G. & Williams, R. L. Crystal structure of a diabody, a bivalent antibody fragment. Structure 2, 1217-26 (1994).

Dustin, M. L., Selvaraj, P., Mattaliano, R. J. and Springer, T. A. (1987b) Anchoring mechanisms for LFA-3 cell adhesion glycoprotein at membrane surface. Nature, 329, 846-848.

Wallich, R., Bernner, C., Brand, Y., Roux, M., Reister, M. and Meuer, S. (1998) Gene structure, promoter characterization and basis for alternative mRNA splicing of the human CD58 gene. J. Immunol., 160, 2862-2871.

Zhen-Yu J.Sun, Volker Dötsch, Mikyung Kim, Jing Li, Ellis L. Reinherz and Gerhard Wagner (1999). Functional glycan-free adhesion domain of human cell surface receptor CD58: design, production and NMR studies. The EMBO Journal Vol. 18 No. 11 pp. 2941-2949.

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

Exemplary Embodiments

Exemplary embodiments provided in accordance with the presently disclosed subject matter include, but are not limited to, the claims and the following embodiments:

1. A vaccine for inducing an immune response against a pathogen in a mammal, the vaccine comprising a conjugate polypeptide comprising an antigen from the pathogen, linked to a ligand or antibody fragment that specifically binds to a surface protein present on an immune cell.

2. The vaccine of embodiment 1, wherein the surface protein is an abundant T-cell surface protein involved in signal transduction and/or adhesion.

3. The vaccine of embodiment 2, wherein the abundant T-cell surface protein is CD2, CD3, CD4, or CD5.

4. The vaccine of embodiment 3, wherein the abundant T-cell surface protein is CD2 or CD3.

5. The vaccine of any one of embodiments 1 to 4, wherein the immune cell is a T cell or an antigen presenting cell (APC).

6. The vaccine of any one of embodiments 1 to 5, wherein the ligand is an ectodomain of a cell adhesion molecule.

7. The vaccine of embodiment 6, wherein the cell adhesion molecule is CD58.

8. The vaccine of any one of embodiments 1 to 7, wherein the surface protein is preferentially expressed by T cells.

9. The vaccine of any one of embodiments 1 to 8, wherein the antibody fragment is an antibody-derived scFv chain.

10. The vaccine of any one of embodiments 1 to 9, wherein the conjugate polypeptide further comprises a lipid anchor, a transmembrane segment, a multimerizing domain, or any combination of these elements.

11. The vaccine of embodiment 10, wherein the lipid anchor is a glycosylphosphatidylinositol anchor.

12. The vaccine of embodiment 10 or 11, wherein the addition of a lipid anchor is directed by a signal sequence.

13. The vaccine of embodiment 12, wherein the signal sequence is derived from CD55.

14. The vaccine of any one of embodiments 10 to 13, wherein the transmembrane segment is derived from a PDGF receptor, glycophorin A, or SARS-CoV-2 spike protein.

15. The vaccine of any one of embodiments 10 to 14, wherein the multimerizing domain is derived from T4 fibritin.

16. The vaccine of any one of embodiments 10 to 14, wherein the multimerizing domain is an Fc domain.

17. The vaccine of embodiment 16, wherein the Fc domain is located at the C-terminus of the conjugate polypeptide.

18. The vaccine of embodiment 16 or 17, wherein the Fc domain is a human IgG1 Fc domain.

19. The vaccine of any one of embodiments 1 to 18, wherein the conjugate polypeptide is a fusion protein comprising the antigen and the ligand or antibody fragment within a single polypeptide chain.

20. The vaccine of embodiment 19, wherein the antibody fragment is an antibody-derived scFv chain, and wherein the VH and VL regions of the scFv are separated by a flexible linker.

21. The vaccine of embodiment 20, wherein the flexible linker is 12 or more amino acids long, and wherein the conjugate polypeptide preferentially binds to the surface protein as a monomer.

22. The vaccine of embodiment 20, wherein the flexible linker is shorter than 12 amino acids long, and wherein the conjugate polypeptide preferentially binds to the surface protein as a multimer.

23. The vaccine of embodiment 22, wherein the multimer is stabilized by disulfide bonds between monomer units.

24. The vaccine of embodiment 22 or 23, wherein the flexible linker is 5 amino acids long.

25. The vaccine of any one of embodiments 1 to 24, wherein the conjugate polypeptide further comprises a tPA leader sequence.

26. The vaccine of embodiment 25, wherein the tPA leader sequence is 23 amino acids long.

27. The vaccine of any one of embodiments 1 to 26, further comprising a second antigen from the pathogen.

28. The vaccine of any one of embodiments 1 to 27, wherein the pathogen is a virus.

29. The vaccine of embodiment 28, wherein the virus is SARS-CoV-2.

30. The vaccine of embodiment 29, wherein the antigen present within the conjugate polypeptide comprises a SARS-CoV-2 spike glycoprotein, or a fragment thereof.

31. The vaccine of embodiment 30, wherein the fragment of the SARS-CoV-2 spike glycoprotein comprises an S1 domain or a receptor-binding domain (RBD).

32. The vaccine of any one of embodiments 27 to 31, wherein the second antigen comprises a SARS-CoV-2 E, M, N, nsp3, nsp4, or nsp6 protein, or a fragment thereof.

33. The vaccine of embodiment 32, wherein the second antigen comprises a fusion protein comprising SARS-CoV-2 E and M proteins, or fragments thereof.

34. The vaccine of any one of embodiments 1 to 33, wherein the mammal is a human.

35. The vaccine of any one of embodiments 1 to 34, wherein the vaccine is formulated for electroporation or subcutaneous injection.

36. The vaccine of any one of embodiments 1 to 35, wherein the conjugate polypeptide comprises an amino acid sequence selected from the group consisting of SEQ ID NO:1, SEQ ID NO:6, SEQ ID NO:9, SEQ ID NO:11, SEQ ID NO:13, SEQ ID NO:15, SEQ ID NO:17, SEQ ID NO:19, and SEQ ID NO:21.

37. A vaccine for inducing an immune response against a pathogen in a mammal, the vaccine comprising a polynucleotide encoding a conjugate polypeptide comprising an antigen from the pathogen fused to a ligand or antibody fragment that specifically binds to a surface protein present on an immune cell.

38. The vaccine of embodiment 37, wherein the surface protein is an abundant T-cell surface protein involved in signal transduction and/or adhesion.

39. The vaccine of embodiment 38, wherein the abundant T-cell surface protein is CD2, CD3, CD4, or CD5.

40. The vaccine of embodiment 39, wherein the abundant T-cell surface protein is CD2 or CD3.

41. The vaccine of any one of embodiments 37 to 40, wherein the immune cell is a T cell or an antigen presenting cell (APC).

42. The vaccine of any one of embodiments 37 to 41, wherein the ligand is an ectodomain of a cell adhesion molecule.

43. The vaccine of embodiment 42, wherein the cell adhesion molecule is CD58.

44. The vaccine of any one of embodiments 37 to 43, wherein the surface protein is preferentially expressed by T cells.

45. The vaccine of any one of embodiments 37 to 44, wherein the antibody fragment is an antibody-derived scFv chain.

46. The vaccine of any one of embodiments 33 to 45, wherein the conjugate polypeptide further comprises a lipid anchor, a transmembrane segment, a multimerizing domain, or any combination of these elements.

47. The vaccine of embodiment 46, wherein the lipid anchor is a glycosylphosphatidylinositol anchor.

48. The vaccine of embodiment 46 or 47, wherein the addition of a lipid anchor is directed by a signal sequence.

49. The vaccine of embodiment 48, wherein the signal sequence is derived from CD55.

50. The vaccine of any one of embodiments 46 to 49, wherein the transmembrane segment is derived from a PDGF receptor, glycophorin A, or SARS-CoV-2 spike protein.

51. The vaccine of any one of embodiments 46 to 50, wherein the multimerizing domain is derived from T4 fibritin.

52. The vaccine of any one of embodiments 46 to 50, wherein the multimerizing domain is an Fc domain.

53. The vaccine of embodiment 52, wherein the Fc domain is located at the C-terminus of the conjugate polypeptide.

54. The vaccine of embodiment 52 or 53, wherein the Fc domain is a human IgG1 Fc domain.

55. The vaccine of any one of embodiments 45 to 54, wherein the VH and VL regions of the scFv are separated within the conjugate polypeptide by a flexible linker.

56. The vaccine of embodiment 55, wherein the flexible linker is 12 or more amino acids long, and wherein the conjugate polypeptide preferentially binds to the surface protein as a monomer.

57. The vaccine of embodiment 55, wherein the flexible linker is shorter than 12 amino acids long, and wherein the conjugate polypeptide preferentially binds to the surface protein as a multimer.

58. The vaccine of embodiment 57, wherein the multimer is stabilized by disulfide bonds.

59. The vaccine of embodiment 57 or 58, wherein the flexible linker is 5 amino acids long.

60. The vaccine of any one of embodiments 37 to 59, wherein the conjugate polypeptide comprises a tPA leader sequence.

61. The vaccine of embodiment 60, wherein the tPA leader sequence is 23 amino acids long.

62. The vaccine of any one of embodiments 37 to 61, further comprising a second polynucleotide encoding a second antigen from the pathogen.

63. The vaccine of any one of embodiments 37 to 62, wherein the pathogen is a virus.

64. The vaccine of embodiment 63, wherein the virus is SARS-CoV-2.

65. The vaccine of embodiment 64, wherein the antigen present within the conjugate polypeptide comprises a SARS-CoV-2 spike glycoprotein or a fragment thereof.

66. The vaccine of embodiment 65, wherein the fragment of the SARS-CoV-2 spike glycoprotein comprises an S1 domain or a receptor-binding domain (RBD).

67. The vaccine of any one of embodiments 62 to 66, wherein the second antigen comprises a SARS-CoV-2 E, M, N, nsp3, nsp4, or nsp6 protein, or a fragment thereof.

68. The vaccine of embodiment 67, wherein the second antigen comprises a fusion protein comprising SARS-CoV-2 E and M proteins, or fragments thereof.

69. The vaccine of any one of embodiments 37 to 68, wherein the mammal is a human.

70. The vaccine of any one of embodiments 37 to 69, wherein the vaccine is formulated for electroporation or subcutaneous injection.

71. The vaccine of any one of embodiments 37 to 70, where the polynucleotide encoding the conjugate polypeptide and/or the second polynucleotide encoding the second antigen are codon optimized.

72. The vaccine of any one of embodiments 37 to 71, wherein the polynucleotide encoding the conjugate polypeptide is present within a first expression cassette, wherein the polynucleotide is operably linked to a first promoter, and/or the second polynucleotide encoding the second antigen is present within a second expression cassette, wherein the second polynucleotide is operably linked to a second promoter.

73. The vaccine of embodiment 72, wherein the second promoter is a mammalian promoter.

74. The vaccine of embodiment 73, wherein the mammalian promoter is an EF-1 alpha promoter.

75. The vaccine of any one of embodiments 37 to 74, wherein the first and/or second expression cassettes are present within a vector.

76. The vaccine of embodiment 75, wherein the vector is administered as naked DNA.

77. The vaccine of embodiment 75, wherein the vector is a viral vector.

78. The vaccine of embodiment 77, wherein the viral vector is a cytomegalovirus (CMV), adenovirus, or adeno-associated virus (AAV) vector.

79. The vaccine of any one of embodiments 37 to 78, further comprising an in vivo transfection reagent.

80. The vaccine of embodiment 79, wherein the in vivo transfection reagent is in vivo-jetPEI™.

81. The vaccine of any one of embodiments 37 to 80, wherein the vaccine is formulated for subcutaneous transfection.

82. The vaccine of any one of embodiments 78 to 81, wherein the vector is a circular CMV vector comprising:

(a) a CMV genome or a portion thereof, wherein the CMV genome or portion thereof contains the first expression cassette or the first and second expression cassettes;
(b) a bacterial artificial chromosome (BAC) sequence comprising an origin of replication;
(c) a first terminase complex recognition locus (TCRL1), comprising at least two viral direct repeat sequences; and
(d) a second terminase complex recognition locus (TCRL2), comprising at least two viral direct repeat sequences;
wherein the CMV genome or portion thereof is flanked by TCRL1 and TCRL2, defining a first region of the circular vector that extends from TCRL1 to TCRL2 and comprises the CMV genome or portion thereof; and
wherein the BAC sequence is located in a second region of the circular vector that extends from TCRL1 to TCRL2 and does not comprise the CMV genome or portion thereof.

83. The vaccine of any one of embodiments 78 to 81, wherein the vector is a circular CMV vector comprising:

(a) a CMV genome or a portion thereof, wherein the CMV genome or portion thereof contains the first expression cassette or the first and second expression cassettes;
(b) a sequence comprising an origin of replication that functions in a single-celled organism;
(c) one or more terminase complex recognition loci (TCRL) comprising a recombinantly introduced polynucleotide sequence that can direct cleavage by an HV terminase complex; wherein
the CMV genome or portion thereof is separated from the sequence comprising an origin of replication by a TCRL; wherein
the CMV genome or portion thereof abuts a TCRL at at least one extremity; and wherein
the sequence comprising the origin of replication abuts a TCRL at at least one extremity.

84. The vaccine of embodiment 82 or 83, wherein one or more of the terminase complex recognition loci comprises a Pac1 site and a Pac2 site.

85. The vaccine of embodiment 84, wherein all of the terminase complex recognition loci comprise a Pac1 site and a Pac2 site.

86. The vaccine of any one of embodiments 77 to 85, wherein the first promoter is a viral promoter.

87. The vaccine of embodiment 86, wherein the viral promoter is a pp65b promoter.

88. The vaccine of any one of embodiments 78 to 87, wherein the vector is a CMV vector, and wherein the CMV is Towne HCMV.

89. The vaccine of any one of embodiments 37 to 88, wherein the polynucleotide encoding the conjugate polypeptide comprises a nucleotide sequence selected from the group consisting of SEQ ID NO:2, SEQ ID NO:7, SEQ ID NO:10, SEQ ID NO:12, SEQ ID NO:14, SEQ ID NO:16, SEQ ID NO:18, SEQ ID NO:20, and SEQ ID NO:22.

90. A conjugate polypeptide comprising an antigen from a pathogen linked to a ligand or antibody fragment that specifically binds to a surface protein present on an immune cell.

91. The conjugate polypeptide of embodiment 90, wherein the surface protein is an abundant T-cell surface protein involved in signal transduction and/or adhesion.

92. The conjugate polypeptide of embodiment 90 or 91, wherein the surface protein is CD2, CD3, CD4, or CD5.

93. The conjugate polypeptide of embodiment 92, wherein the surface protein is CD2 or CD3.

94. The conjugate polypeptide of any one of embodiments 90 to 93, wherein the immune cell is a T cell or an antigen presenting cell (APC).

95. The conjugate polypeptide of any one of embodiments 90 to 94, wherein the ligand is an ectodomain of a cell adhesion molecule.

96. The conjugate polypeptide of embodiment 95, wherein the cell adhesion molecule is CD58.

97. The conjugate polypeptide of any one of embodiments 90 to 96, wherein the surface protein is preferentially expressed by T cells.

98. The conjugate polypeptide of any one of embodiments 90 to 94 or 95 to 97, wherein the antibody fragment is an antibody-derived scFv chain.

99. The conjugate polypeptide of any one of embodiments 90 to 98, wherein the conjugate polypeptide further comprises a lipid anchor, a transmembrane segment, a multimerizing domain, or any combination of these elements.

100. The conjugate polypeptide of embodiment 99, wherein the lipid anchor is a glycosylphosphatidylinositol anchor.

101. The conjugate polypeptide of embodiment 99 or 100, wherein the addition of a lipid anchor is directed by a signal sequence.

102. The conjugate polypeptide of embodiment 101, wherein the signal sequence is derived from CD55.

103. The conjugate polypeptide of any one of embodiments 99 to 102, wherein the transmembrane segment is derived from PDGF receptor, glycophorin A, or the SARS-CoV-2 spike protein.

104. The conjugate polypeptide of any one of embodiments 99 to 103, wherein the multimerizing domain is derived from T4 fibritin.

105. The conjugate polypeptide of any one of embodiments 99 to 103, wherein the multimerizing domain is an Fc domain.

106. The conjugate polypeptide of embodiment 105, wherein the Fc domain is located at the C-terminus of the conjugate polypeptide.

107. The conjugate polypeptide of embodiment 105 or 106, wherein the Fc domain is a human IgG1 Fc domain.

108. The conjugate polypeptide of any one of embodiments 98 to 107, wherein the antibody fragment is an antibody-derived scFv chain, and wherein the VH and VL regions of the scFv are separated by a flexible linker.

109. The conjugate polypeptide of embodiment 108, wherein the flexible linker is 12 or more amino acids long, and wherein the conjugate polypeptide preferentially binds to the surface protein as a monomer.

110. The conjugate polypeptide of embodiment 109, wherein the flexible linker is shorter than 12 amino acids long, and wherein the conjugate polypeptide preferentially binds to the surface protein as a multimer.

111. The conjugate polypeptide of embodiment 110, wherein the multimer is stabilized by disulfide bonds between monomer units.

112. The conjugate polypeptide of embodiment 110 or 111, wherein the flexible linker is 5 amino acids long.

113. The conjugate polypeptide of any one of embodiments 90 to 112, wherein the conjugate polypeptide further comprises a tPA leader sequence.

114. The conjugate polypeptide of embodiment 113, wherein the tPA leader sequence is 23 amino acids long.

115. The conjugate polypeptide of any one of embodiments 90 to 114, wherein the pathogen is a virus.

116. The conjugate polypeptide of embodiment 115, wherein the virus is SARS-CoV-2.

117. The conjugate polypeptide of embodiment 116, wherein the antigen comprises a SARS-CoV-2 spike glycoprotein or a fragment thereof.

118. The conjugate polypeptide of embodiment 117, wherein the fragment of the SARS-CoV-2 spike glycoprotein comprises an S1 domain or a receptor-binding domain (RBD).

119. The conjugate polypeptide of any one of embodiments 90 to 118, comprising an amino acid sequence selected from the group consisting of SEQ ID NO:1, SEQ ID NO:6, SEQ ID NO:9, SEQ ID NO:11, SEQ ID NO:13, SEQ ID NO:15, SEQ ID NO:17, SEQ ID NO:19, and SEQ ID NO:21.

120. A conjugate polypeptide comprising (i) a tissue plasminogen activator (tPA) signal sequence; (ii) a single-chain variable fragment (scFv) specifically binding to CD2, CD3, or CD4; (iii) a flexible linker; and (iv) a SARS-CoV-2 receptor binding domain (RBD).

121. The conjugate polypeptide of embodiment 120, comprising the amino acid sequence of SEQ ID NO:6, SEQ ID NO: 9, SEQ ID NO:11, SEQ ID NO:13, SEQ ID NO:15, SEQ ID NO:17, SEQ ID NO:19, SEQ ID NO:21, SEQ ID NO:23, SEQ ID 25, or SEQ ID NO:27.

122. A polynucleotide encoding the conjugate polypeptide of any one of embodiments 90 to 121.

123. The polynucleotide of embodiment 122, wherein the polynucleotide is codon optimized.

124. The polynucleotide of embodiment 123, comprising a nucleotide sequence selected from the group consisting of SEQ ID NO:2, SEQ ID NO:7, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NO:28.

125. An expression cassette comprising the polynucleotide of any one of embodiments 122 to 124.

126. The expression cassette of embodiment 125, comprising the nucleotide sequence of SEQ ID NO:8.

127. A vector comprising the expression cassette of embodiment 125 or 126.

128. The vector of embodiment 127, wherein the vector is a plasmid.

129. The vector of embodiment 127, wherein the vector is an adenoviral vector.

130. A diabody comprising the conjugate polypeptide of any one of embodiments 98 to 121.

131. A dimer comprising the conjugate polypeptide of any one of embodiments 99 to 121.

132. A vaccine comprising the conjugate polypeptide of any one of embodiments 90 to 121, the polynucleotide of any one of embodiments 122 to 124, the expression cassette of embodiment 125 or 126, the vector of any one of embodiments 127 to 129, the diabody of embodiment 130, or the dimer of embodiment 131.

133. A method of inducing an immune response against a pathogen in a mammal, the method comprising administering to the mammal any of the vaccines of embodiments 1 to 89 or 132.

134. The method of embodiment 133, wherein the vaccine is administered subcutaneously or by electroporation.

135. The method of embodiment 133 or 134, wherein the method induces a neutralizing antibody response in the mammal against the antigen present within the conjugate polypeptide, and wherein the neutralizing response is substantially greater than any antibody-dependent enhancement of infectivity (ADEI) induced in the mammal by the vaccine.

136. The method of embodiment 135, wherein the vaccine does not substantially induce ADEI in the mammal.

137. The method of any one of embodiments 133 to 136, wherein the method induces both CD4+ and CD8+ T cell responses against the second antigen.

138. The method of any one of embodiments 133 to 137, wherein the method comprises administering to the mammal by electroporation a DNA prime comprising the vector of embodiments 127 or 128, followed by a boost with an adenoviral vector encoding RBD.

139. The method of embodiment 138, wherein the boost is performed after about 28 days.

140. The method of any one of embodiments 133 to 139, wherein the mammal is a human.

INFORMAL SEQUENCE LISTING

| SEQ ID NO: | Sequence | Description |
|---|---|---|
| 1 | MDAMKRGLCCVLLLCGAVFVSASEVQLVESGGGLVQPGGSLRLSCAASGFTFNT YAMNWVRQAPGKGLEWVARIRSKYNNYATYYAASVKGRFTISRDDSKNSLYLQ MNSLKTEDTAVYYCARHGNFGNSYVSWFAYWGQGTLVTVSSGGGGSGGGGSG GGGSQTVVTQEPSLTVSPGGTVTLTCRSSTGAVTTSNYANWVQQKPGQAPRGLIG GTNKRAPGTPARFSGSLLGGKAALTLSGVQPEDEAEYYCALWYSNLWVFGGGTK LTVLGGGGSGGGGSGGGGSVNLTTRTQLPPAYTNSFTRGVYYPDKVFRSSVLHST QDLFLPFFSNVTWFHAIHVSGTNGTKRFDNPVLPFNDGVYFASTEKSNIIRGWIFG TTLDSKTQSLLIVNNATNVVIKVCEFQFCNDPFLGVYYHKNNKSWMESEFRVYSS ANNCTFEYVSQPFLMDLEGKQGNFKNLREFVFKNIDGYFKIYSKHTPINLVRDLPQ GFSALEPLVDLPIGINITRFQTLLALHRSYLTPGDSSSGWTAGAAAYYVGYLQPRT FLLKYNENGTITDAVDCALDPLSETKCTLKSFTVEKGIYQTSNFRVQPTESIVRFPN ITNLCPFGEVFNATRFASVYAWNRKRISNCVADYSVLYNSASFSTFKCYGVSPTKL NDLCFTNVYADSFVIRGDEVRQIAPGQTGKIADYNYKLPDDFTGCVIAWNSNNLD SKVGGNYNYLYRLFRKSNLKPFERDISTEIYQAGSTPCNGVEGFNCYFPLQSYGFQ PTNGVGYQPYRVVVLSFELLHAPATVCGPKKSTNLVKNKCVNFNFNGLTGTGVL TESNKKFLPFQQFGRDIADTTDAVRDPQTLEILDITPCSFGGVSVITPGTNTSNQVA VLYQDVNCTEVPVAIHADQLTPTWRVYSTGSNVFQTRAGCLIGAEHVNNSYECDI PIGAGICASYQTQTNSPRRARSVASQ* | tPAsignal-antiCD3scFv-linker-S1 protein |
| 2 | ATGGATGCAATGAAGAGAGGGCTCTGCTGTGCTGCTGCTGTGTGGAGCAGT CTTCGTTTCGGCTAGCGAGGTGCAGCTCGTTGAGAGTGGTGGGGGTCTGGTCC AACCCGGTGGGAGTCTCCGCTTGTCATGTGCAGCTTCTGGCTTCACATTTAAC ACCTATGCCATGAACTGGGTCCGGCAGGCCCCCGGCAAGGGACTTGAATGGG TTGCACGGATCCGCTCAAAATACAACAACTACGCGACTTACTACGCTGCCTCA GTCAAGGGTCGCTTCACCATTAGTCGCGACGACTCTAAGAATAGTCTTTATTT GCAGATGAATAGTCTCAAGACCGAGGACACTGCGGTATATTATTGCGCACGG CACGGAAATTTTGGCAATTCATATGTTAGTTGGTTCGCTTACTGGGGCAAGG CACGCTCGTTACGGTCTCAAGTGGTGGTGGCGGTTCAGGGGGAGGGGGCTCTG GAGGGGGCGGTTCTCAAACCGTTGTCACCCAGGAACCAAGCCTGACCGTAAG CCCTGGTGGGACCGTGACTCTCACGTGTAGAAGTTCTACAGGAGCTGTTACTA CCTCAAACTACGCTAACTGGGTACAACAAAAACCCGGTCAAGCACCAAGGGG ACTGATAGGCGGAACAAACAAAAGGGCGCCGGGTACTCCGGCACGATTTTCC GGATCTCTTCTTGGAGGAAAGGCAGCGTTGACTTTGTCTGGAGTTCAGCCCGA GGATGAGGCAGAGTATTATTGCGCACTCTGGTATAGTAACCTCTGGGTCTTCG GCGGAGGAACTAAGCTTACGGTCCTTGGGGGTGGCGGCAGTGGCGGTGGCGG GTCTGGAGGTGGGGGTTCCGTTAATCTCACGACCAGGACCCAATTGCCTCCCG CGTATACTAACTCTTTCACGAGGGGAGTCTACTATCCTGACAAAGTATTTAGG TCTTCAGTGCTGCATAGTACACAAGACCTGTTCCTTCCGTTTTTCAGCAACGTG ACTTGGTTCCACGCTATACACGTCTCAGGGACGAATGGAACAAAGCGCTTCGA TAATCCGGTTTTGCCATTTAATGATGGTGTCTATTTCGCATCCACAGAAAGTC CAACATTATCAGGGGGTGGATCTTTGGTACGACGCTGGATAGCAAAACACAG TCCCTCCTTATCGTCAACAATGCCACGAATGTGGTGATTAAGGTTTGCGAATTT CAATTTTGTAACGACCCTTTTCTTGGCGTATATTATCATAAAAACAACAAGTCC TGGATGGAAAGCGAATTCCGCGTATACAGTTCCGCAAACAACTGTACATTTGA ATATGTGAGCCAACCTTTTCTGATGGACCTGGAGGGCAAACAGGGCAACTTTA AAAATTTGAGAGAGTTCGTCTTCAAAAATATTGATGGATATTTCAAGATTTAT AGTAAGCATACGCCCATAAATCTTGTCCGGGATCTGCCGCAGGGTTTTAGCGC TCTCGAACCCTTGGTAGACCTCCCGATTGGTATAAACATCACCAGGTTTCAGA CCCTTCTTGCGTTGCACCGCAGCTATCTCACGCCAGGCGATAGTAGTTCAGGT TGGACTGCCGGAGCAGCAGCCTACTACGTAGGCTACCTTCAACCTAGAACGTT TCTGTTGAAATATAATGAAAATGGTACAATCACAGACGCGGTCGACTGCGCAC TGGACCCGCTGAGCGAAACCAAATGTACGCTCAAGTCCTTCACCGTAGAGAA AGGCATCTACCAGACTTCTAATTTCCGAGTGCAGCCGACGGAGTCAATCGTGA GATTCCCTAACATAACTAATTTGTGTCCATTTGGCGAAGTGTTCAATGCAACC AGATTCGCCTCCGTCTATGCGTGGAATCGAAAAAGAATTTCAAACTGCGTAGC GGATTATTCTGTCTTGTACAATAGTGCCTCCTTTAGTACGTTCAAGTGTTATGG GGTGTCACCAACGAAGTTGAATGATCTTTGTTTCACGAATGTTTACGCTGATTC ATTTGTAATACGCGGAGACGAAGTTAGACAAATCGCACCAGGGCAGACAGGC AAGATCGCGGATTATAATTATAAGCTGCCAGACGACTTCACTGGGTGCGTTAT CGCATGGAACTCCAACAACTTGGATAGTAAAGTGGGCGGGAATTACAACTAC CTGTATAGACTTTTCCGAAAGTCCAATTTGAAGCCATTCGAAAGGGACATTTC TACTGAAATATATCAAGCGGGATCAACACCTTGCAACGGAGTGGAAGGGTTC AACTGCTACTTTCCGCTGCAATCTTATGGGTTTCAACCGACTAATGGAGTCGG GTATCAGCCTTACAGAGTTGTTGTTCTTTCCTTTGAGCTGTTGCATGCCCCGGC AACCGTATGTGGGCCCAAGAAATCTACAAACCTCGTTAAGAATAAATGCGTG AATTTCAACTTCAATGGTCTCACCGGGACGGGGGTCCTGACCGAAAGTAACAA | tPAsignal-antiCD3scFv-linker-S1 codon-optimized DNA |

| SEQ ID NO: | Sequence | Description |
|---|---|---|
| | GAAATTTCTGCCCTTTCAGCAATTCGGAAGAGACATCGCGGACACTACAGACG<br>CCGTTCGGGACCCGCAGACTCTCGAAATTCTTGACATCACGCCGTGTTCATTC<br>GGAGGCGTTTCCGTGATTACACCAGGAACGAATACCAGCAATCAAGTGGCAG<br>TGTTGTATCAAGATGTTAATTGCACTGAAGTGCCTGTCGCTATCCACGCGGAC<br>CAGCTCACGCCTACGTGGAGGGTGTATTCAACAGGAAGCAACGTGTTCCAAA<br>CACGAGCGGGTTGTCTTATAGGGGCGGAGCACGTGAACAATAGTTACGAATG<br>TGATATACCGATAGGGGCTGGGATATGTGCGTCTTATCAAACACAGACGAATA<br>GCCCCAGGCGCGCTCGAAGTGTGGCAAGCCAATAG | |
| 3 | ATGAGCGATAACGGCCCCCAGAATCAGAGGAATGCACCTAGGATAACATTTG<br>GAGGTCCGTCAGACAGCACTGGCTCCAACCAGAATGGCGAGCGGTCTGGCGC<br>GCGGTCTAAGCAAAGGAGACCACAAGGTCTCCCGAATAACACGGCCTCCTGG<br>TTTACAGCGCTCACCCAGCACGGTAAAGAGGACCTGAAGTTCCCTAGGGGGC<br>AAGGTGTACCGATTAATACCAACAGCTCCCCCGATGACCAGATTGGTTATTAT<br>AGAAGAGCTACAAGACGCATACGGGGTGGAGATGGGAAGATGAAGGACCTCT<br>CCCCTCGGTGGTATTTTTATTATCTGGGCACCGGACCGGAAGCCGGGCTCCCC<br>TACGGCGCCAATAAGGACGGTATAATATGGGTCGCCACTGAGGGTGCCCTCA<br>ATACCCCGAAGGACCACATTGGCACTCGAAACCCGGCAAACAACGCAGCTAT<br>TGTCCTGCAACTCCCACAGGGTACCACGCTCCCGAAAGGTTTTTATGCCGAAG<br>GGTCTCGCGGGGTTCACAGGCTAGCAGTCGAAGCTCATCTCGGAGCCGAAA<br>TAGCTCAAGGAATTCAACACCCGGAAGCTCCAGAGGCACAAGCCCTGCGCGG<br>ATGGCAGGGAACGGAGGCGATGCTGCCCTGGCCCTCCTTCTCTTGGATAGACT<br>TAATCAGCTGGAATCCAAAATGTCAGGAAAGGGCCAGCAACAACAAGGTCAG<br>ACAGTGACCAAAAAATCCGCCGCAGAGGCCAGTAAGAAACCTAGACAGAAGC<br>GAACTGCTACAAAGGCCTATAATGTAACTCAGGCGTTCGGACGGCGAGGCCC<br>TGAACAAACCCAGGGCAATTTCGGTGACCAAGAACTCATAAGACAGGGAACT<br>GACTACAAACATTGGCCCCAGATTGCACAATTTGCCCCATCCGCCTCAGCCTT<br>CTTCGGAATGTCTCGCATCGGGATGGAGGTAACACCGAGCGGGACCTGGCTC<br>ACATACACAGGTGCGATAAAGCTCGATGACAAAGATCCCAATTTTAAAGACC<br>AAGTGATACTTCTTAATAAGCACATAGACGCCTATAAAACCTTCCCGCCCACT<br>GAGCCAAAGAAAGACAAGAAAAAAAAGCGGACGAGACACAAGCCCTTCCG<br>CAAAGACAGAAAAACAGCAAACGGTTACATTGCTTCCTGCGGCAGACCTGG<br>ATGATTTTTCCAAACAGCTTCAGCAATCTATGTCTAGCGCAGATAGTACCCAG<br>GCGTAA | Codon-optimized coding sequence for the N protein of SARS-CoV-2 |
| 4 | ATGGCTGACAGCAATGGGACGATCACAGTCGAGGAACTCAAGAAACTGTTGG<br>AGCAGTGGAATTTGGTGATAGGCTTCTTGTTCTTGACGTGGATATGCTTGCTGC<br>AGTTTGCCTATGCGAATAGAAACCGCTTCTTGTATATAATCAAACTGATATTTC<br>TCTGGTTGCTCTGGCCCCGTCACGCTTGCATGTTTTGTTTTGGCGGCCGTTTAC<br>GGATCAACTGGATTACAGGGGGAATTGCAATAGCGATGGCATGTCTGGTAGG<br>ATTGATGTGGCTGTCCTACTTTATTGCGTCATTTCGATTGTTTGCACGCACTCG<br>GTCCATGTGGTCCTTTAATCCAGAAACCAATATACTGCTCAACGTACCATTGC<br>ATGGGACTATACTGACGCGACCTCTTTTGGAATCAGAGCTGGTGATAGGTGCA<br>GTGATACTGAGAGGGCATCTCCGAATAGCGGGCACCACCTGGGCAGATGTG<br>ACATCAAAGACCTTCCAAAAGAAATCACGGTGGCCACGTCAAGGACATTGTC<br>ATATTACAAACTTGGCGCATCCCAAAGAGTAGCAGGAGATTCTGGTTTCGCGG<br>CATACTCTAGGTACAGGATCGGAATTACAAACTGAACACAGATCATTCCTCT<br>AGTTCCGACAACATAGCCCTTTTGGTACAGATGTACTCTTTCGTATCAGAGGA<br>GACTGGTACTCTTATAGTTAATTCTGTGCTGCTCTTTCTTGCGTTTGTCGTCTTT<br>CTGCTTGTAACACTTGCTATTCTTACTGCGTTGAGACTCTGTGCCTATTGTTGT<br>AATATAGTCAATGTATCTTTGGTAAAGCCTAGTTTTTATGTGTATAGCCGGGTC<br>AAAAACCTTAACTCCAGCCGAGTTCCCGACCTTTTGGTT | Codon-optimized coding sequence for fusion protein comprising the E and M proteins of SARS-CoV-2 |
| 5 | GGGGSGGGGSGGGGS | (Gly4Ser)3 flexible linker |
| 6 | MDAMKRGLCCVLLLCGAVFVSASEVQLVESGGGLVQPGGSLRLSCAASGFTFNT<br>YAMNWVRQAPGKGLEWVARIRSKYNNYATYYAASVKGRFTISRDDSKNSLYLQ<br>MNSLKTEDTAVYYCARHGNFGNSYVSWFAYWGQGTLVTVSSGGGGSGGGGSG<br>GGGSQTVVTQEPSLTVSPGGTVTLTCRSSTGAVTTSNYANWVQQKPGQAPRGLIG<br>GTNKRAPGTPARFSGSLLGGKAALTLSGVQPEDEAEYYCALWYSNLWVFGGGTK<br>LTVLGGGGSGGGGSGGGGSRVQPTESIVRFPNITNLCPFGEVFNATRFASVYAWN<br>RKRISNCVADYSVLYNSASFSTFKCYGVSPTKLNDLCFTNVYADSFVIRGDEVRQI<br>APGQTGKIADYNYKLPDDFTGCVIAWNSNNLDSKVGGNYNYLYRLFRKSNLKPF<br>ERDISTEIYQAGSTPCNGVEGFNCYFPLQSYGFQPTNGVGYQPYRVVVLSFELLHA<br>PATVCGPKKSTNLVKNKCVNF | Anti-CD3 scFv-RBD protein |
| 7 | ATGGATGCAATGAAGAGAGGGCTCTGCTGTGTGCTGCTGCTGTGTGGAGCAGT<br>CTTCGTTTCGGCTAGCGAGGTGCAGCTCGTTGAGAGTGGTGGGGGTCTGGTCC<br>AACCCGGTGGGAGTCTCCGCTTGTCATGTGCAGCTTCTGGCTTCACATTTAAC<br>ACCTATGCCATGAACTGGGTCCGGCAGGCCCCCGGCAAGGGACTTGAATGGG<br>TTGCACGGATCCGCTCAAAATACAACAACTACGCGACTTACTACGCTGCCTCA<br>GTCAAGGGTCGCTTCACCATTAGTCGCGACGACTCTAAGAATAGTCTTTATTT<br>GCAGATGAATAGTCTCAAGACCGAGGACACTGCCGTATATTATTGCGCACGG<br>CACGGAAATTTTGGCAATTCATATGTTAGTTGGTTCGCTTACTGGGGGCAAGG | Anti-CD3 scFv-RBD codon-optimized DNA |

| SEQ ID NO: | Sequence | Description |
|---|---|---|
| | CACGCTCGTTACGGTCTCAAGTGGTGGTGGCGGTTCAGGGGGAGGGGGCTCTG<br>GAGGGGGCGGTTCTCAAACCGTTGTCACCCAGGAACCAAGCCTGACCGTAAG<br>CCCTGGTGGGACCGTGACTCTCACGTGTAGAAGTTCTACAGGAGCTGTTACTA<br>CCTCAAACTACGCTAACTGGGTACAACAAAAACCCGGTCAAGCACCAAGGGG<br>ACTGATAGGCGGAACAAACAAAAGGGCGCCGGGTACTCCGGCACGATTTTCC<br>GGATCTCTTCTTGGAGGAAAGGCAGCGTTGACTTTGTCTGGAGTTCAGCCCGA<br>GGATGAGGCAGAGTATTATTGCGCACTCTGGTATAGTAACCTCTGGGTCTTCG<br>GCGGAGGAACTAAGCTTACGGTCCTTGGGGGTGGCGGCAGTGGCGGTGGCGG<br>GTCTGGAGGTGGGGGTTCCCGAGTGCAGCCGACGGAGTCAATCGTGAGATTC<br>CCTAACATAACTAATTTGTGTCCATTTGGCGAAGTGTTCAATGCAACCAGATT<br>CGCCTCCGTCTATGCGTGGAATCGAAAAGAATTTCAAACTGCGTAGCGGATT<br>ATTCTGTCTTGTACAATAGTGCCTCCTTTAGTACGTTCAAGTGTTATGGGGTGT<br>CACCCAACGAAGTTGAATGATCTTTGTTTCACGAATGTTTACGCTGATTCATTTG<br>TAATACGCGGAGACGAAGTTAGACAAATCGCACCAGGGCAGACAGGCAAGAT<br>CGCGGATTATAATTATAAGCTGCCAGACGACTTCACTGGGTGCGTTATCGCAT<br>GGAACTCCAACAACTTGGATAGTAAAGTGGGCGGGAATTACAACTACCTGTA<br>TAGACTTTTCCGAAAGTCCAATTTGAAGCCATTCGAAAGGGACATTTCTACTG<br>AAATATATCAAGCGGGATCAACACCTTGCAACGGAGTGGAAGGGTTCAACTG<br>CTACTTTCCGCTGCAATCTTATGGGTTTCAACCGACTAATGGAGTCGGGTATC<br>AGCCTTACAGAGTTGTTGTTCTTTCCTTTGAGCTGTTGCATGCCCCGGCAACCG<br>TATGTGGGCCCAAGAAATCTACAAACCTCGTTAAGAATAAATGCGTGAATTTC<br>TAG | |
| 8 | CGTGAGGCTCCGGTGCCCGTCAGTGGGCAGAGCGCACATCGCCCACAGTCCCC<br>GAGAAGTTGGGGGGAGGGGTCGGCAATTGAACCGGTGCCTAGAGAAGGTGGC<br>GCGGGGTAAACTGGGAAAGTGATGTCGTGTACTGGCTCCGCCTTTTTCCCGAG<br>GGTGGGGGAGAACCGTATATAAGTGCAGTAGTCGCCGTGAACGTTCTTTTTCG<br>CAACGGGTTTGCCGCCAGAACAGGTAAGTGCCGTGTGTGGTTCCCGCGGGC<br>CTGGCCTCTTTACGGGTTATGGCCCTTGCGTGCCTTGAATTACTTCCACCTGGC<br>TGCAGTACGTGATTCTTGATCCCGAGCTTCGGGTTGGAAGTGGGTGGGAGAGT<br>TCGAGGCCTTGCGCTTAAGGAGCCCCTTCGCCTCGTGCTTGAGTTGAGGCCTG<br>GCCTGGGCGCTGGGGCCGCCGCGTGCGAATCTGGTGGCACCTTCGCGCCTGTC<br>TCGCTGCTTTCGATAAGTCTCTAGCCATTTAAAATTTTTGATGACCTGCTGCGA<br>CGCTTTTTTTCTGGCAAGATAGTCTTGTAAATGCGGGCCAATCTGCACACT<br>GGTATTTCGGTTTTTGGGGCCGCGGGCGGCGACGGGGCCCGTGCGTCCCAGCG<br>CACATGTTCGGCGAGGCGGGGCTGCGAGCGCGGCCACCGAGAATCGGACGG<br>GGGTAGTCTCAAGCTGGCCGGCCTGCTCTGGTGCCTGGCCTCGCGCCGCCGTG<br>TATCGCCCCGCCCTGGGCGGCAAGGCTGGCCCGGTCGGCCACCAGTTGCGTGAG<br>CGGAAAGATGGCCGCTTCCCGGCCCTGCTGCAGGGAGCTCAAATGGAGGAC<br>GCGGCGCTCGGGAGAGCGGGCGGGTGAGTCACCCACACAAAGGAAAAGGGC<br>CTTTCCGTCCTCAGCCGTCGCTTCATGTGACTCCACGGAGTACCGGGCGCCGT<br>CCAGGCACCTCGATTAGTTCTCGAGCTTTTGGAGTACGTCGTCTTTAGGTTGGG<br>GGGAGGGGTTTTATGCGATGAGTTTCCCCACACTGAGTGGGTGGAGACTGA<br>AGTTAGGCCAGCTTGGCACTTGATGTAATTCTCCTTGGAATTTGCCCTTTTTGA<br>GTTTGGATCTTGGTTCATTCTCAAGCCTCAGACAGTGGTTCAAAGTTTTTTTCT<br>TCCATTTCAGGTGTCGTGAGGAATTAGCTGGCGCGCCTTCCCGCCACCATGGA<br>TGCAATGAAGAGAGGGCTCTGCTGTGTGCTGCTGCTGTGTGGAGCAGTCTTCG<br>TTTCGGCTAGCGAGGTGCAGCTCGTTGAGAGTGGTGGGGGTCTGGTCCAACCC<br>GGTGGGAGTCTCCGCTTGTCATGTGCAGCTTCTGGCTTCACATTTAACACCTAT<br>GCCATGAACTGGGTCCGGCAGGCCCCCGGCAAGGGACTTGAATGGGTTGCAC<br>GGATCCGCTCAAAATACAACAACTACGCGACTTACTACGCTGCCTCAGTCAAG<br>GGTCGCTTCACCATTAGTCGCGACGACTCTAAGAATAGTCTTTATTTGCAGAT<br>GAATAGTCTCAAGACCGAGGACACTGCGGTATATTATTGCGCACGGCACGGA<br>AATTTTGGCAATTCATATGTTAGTTGGTCGCTTACTGGGGGCAAGGCACGCT<br>CGTTACGGTCTCAAGTGGTGGTGGCGGTTCAGGGGGAGGGGGCTCTGGAGGG<br>GGCGGTTCTCAAACCGTTGTCACCCAGGAACCAAGCCTGACCGTAAGCCCTGG<br>TGGGACCGTGACTCTCACGTGTAGAAGTTCTACAGGAGCTGTTACTACCTCAA<br>ACTACGCTAACTGGGTACAACAAAAACCCGGTCAAGCACCAAGGGGACTGAT<br>AGGCGGAACAAACAAAAGGGCGCCGGGTACTCCGGCACGATTTTCCGGATCT<br>CTTCTTGGAGGAAAGGCAGCGTTGACTTTGTCTGGAGTTCAGCCCGAGGATGA<br>GGCAGAGTATTATTGCGCACTCTGGTATAGTAACCTCTGGGTCTTCGGCGGAG<br>GAACTAAGCTTACGGTCCTTGGGGGTGGCGGCAGTGGCGGTGGCGGGTCTGG<br>AGGTGGGGGTTCCCGAGTGCAGCCGACGGAGTCAATCGTGAGATTCCCTAAC<br>ATAACTAATTTGTGTCCATTTGGCGAAGTGTTCAATGCAACCAGATTCGCCTC<br>CGTCTATGCGTGGAATCGAAAAGAATTTCAAACTGCGTAGCGGATTATTCTG<br>TCTTGTACAATAGTGCCTCCTTTAGTACGTTCAAGTGTTATGGGGTGTCACCAA<br>CGAAGTTGAATGATCTTTGTTTCACGAATGTTTACGCTGATTCATTTGTAATAC<br>GCGGAGACGAAGTTAGACAAATCGCACCAGGGCAGACAGGCAAGATCGCGG<br>ATTATAATTATAAGCTGCCAGACGACTTCACTGGGTGCGTTATCGCATGGAAC<br>TCCAACAACTTGGATAGTAAAGTGGGCGGGAATTACAACTACCTGTATAGACT<br>TTTCCGAAAGTCCAATTTGAAGCCATTCGAAAGGGACATTTCTACTGAAATAT<br>ATCAAGCGGGATCAACACCTTGCAACGGAGTGGAAGGGTTCAACTGCTACTTT<br>CCGCTGCAATCTTATGGGTTTCAACCGACTAATGGAGTCGGGTATCAGCCTTA<br>CAGAGTTGTTGTTCTTTCCTTTGAGCTGTTGCATGCCCCGGCAACCGTATGTGG<br>GCCCAAGAAATCTACAAACCTCGTTAAGAATAAATGCGTGAATTTCTAGTAGC | Anti-CD3 scFv-<br>RBD expression<br>cassette |

-continued

| SEQ ID NO: | Sequence | Description |
|---|---|---|
| | CTGCAGGACGCCACAGCTCTGATCATAATCAGCCATACCACATTTGTAGAGGT<br>TTTACTTGCTTTAAAAAACCTCCCACACCTCCCCCTGAACCTGAAACATAAAA<br>TGAATGCAATTGTTGTTGTTAACTTGTTTATTGCAGCTTATAATGGTTACAAAT<br>AAAGCAATAGCATCACAAATTTCACAAATAAAGCATTTTTTTCACTGCATTCT<br>AGTTGTGGTTTGTCCAAACTCATCAATGTATCT | |
| 9 | MDAMKRGLCCVLLLCGAVFVSASEVQLVESGGGLVQPGGSLRLSCAASGFTFNT<br>YAMNWVRQAPGKGLEWVARIRSKYNNYATYYAASVKGRFTISRDDSKNSLYLQ<br>MNSLKTEDTAVYYCARHGNFGNSYVSWFAYWGQGTLVTVSSGGGGSGGGGSG<br>GGGSQTVVTQEPSLTVSPGGTVTLTCRSSTGAVTTSNYANWVQQKPGQAPRGLIG<br>GTNKRAPGTPARFSGSLLGGKAALTLSGVQPEDEAEYYCALWYSNLWVFGGGTK<br>LTVLGGGGSGGGGSGGGGSRVQPTESIVRFPNITNLCPFGEVFNATRFASVYAWN<br>RKRISNCVADYSVLYNSASFSTFKCYGVSPTKLNDLCFTNVYADSFVIRGDEVRQI<br>APGQTGKIADYNYKLPDDFTGCVIAWNSNNLDSKVGGNYNYLYRLFRKSNLKPF<br>ERDISTEIYQAGSTPCNGVEGFNCYFPLQSYGFQPTNGVGYQPYRVVVLSFELLHA<br>PATVCGPKKSTNLVKNKCVNFGGGGSGGGGSGGGGSDKTHTCPPCPAPELLGGP<br>SVFLFPPKPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPVLDSDG<br>SFFLYSKLTVDKSRWQQGNVFSCSVMHEALHNHYTQKSLSLSPGK | Anti-CD3 scFv-<br>RBD-Fc protein |
| 10 | ATGGATGCCATGAAGAGAGGATTGTGTTGCGTACTTCTCCTTTGCGGGGCAGT<br>CTTTGTGTCAGCTAGTGAAGTTCAACTCGTCGAATCAGGTGGAGGCCTTGTGC<br>AACCGGGAGGTTCCTTGCGGCTTTCATGTGCAGCGTCAGGCTTTACCTTCAAT<br>ACATATGCCATGAACTGGGTCCGCCAGGCCCCGGGCAAGGGTCTCGAATGGG<br>TAGCGCGCATCCGCAGCAAGTACAATAATTATGCGACCTATTATGCAGCCTCA<br>GTAAAAGGGAGGTTCACCATATCTCGGGACGACTCTAAAAATAGCCTCTATCT<br>CCAGATGAATAGTCTTAAAACTGAGGATACGGCGGTGTACTATTGCGCCCGGC<br>ATGGCAACTTTGGGAATAGCTATGTCTCATGGTTTGCCTATTGGGGCCAGGGA<br>ACGCTGGTGACCGTTTCAAGCGGAGGAGGCGGATCTGGCGGCGGAGGTTCAG<br>GTGGCGGCGGTTCACAAACAGTCGTGACCCAGGAACCCAGCCTTACCGTCTCT<br>CCCGGAGGGACAGTTACACTGACGTGCAGATCAAGTACCGGCGCCGTCACTA<br>CTTCTAACTACGCTAATTGGGTTCAACAAAAGCCGGGTCAAGCACCACGAGGT<br>TTGATAGGGGGGACAAATAAAAGGGCTCCAGGCACCCCCGCTCGCTTCTCCG<br>GGAGTCTCTTGGGGGGCAAAGCCGCGCTGACGTTGTCTGGAGTCCAGCCTGAG<br>GATGAAGCCGAGTATTACTGCGCTCTTTGGTACTCTAACCTGTGGGTCTTTGG<br>GGGAGGCACGAAACTTACAGTCTTGGGTGGCGGTGGTTCAGGCGGTGGTGGA<br>AGCGGAGGCGGCGGTTCTAGGGTGCAGCCGACAGAAAGTATCGTCCGGTTTC<br>CGAACATTACCAATTTGTGTCCCTTCGGCGAAGTCTTTAATGCTACAAGGTTTG<br>CCAGCGTCTACGCATGGAATCGCAAAAGAATAAGCAATTGCGTAGCCGATTA<br>TTCAGTATTGTACAATTCCGCTTCTTTTTCAACATTCAAATGTTATGGGGTGTC<br>CCCTACGAAGTTGAATGACCTGTGTTTCACGAATGTCTACGCAGATTCTTTTGT<br>CATACGCGGCGACGAAGTGAGACAAATTGCACCCGGCCAAACCGGCAAAATA<br>GCGGACTATAACTATAAGCTCCCCGACGATTTCACCGGGTGCGTCATAGCCTG<br>GAACAGCAACAACCTCGATTCAAAAGTCGGAGGCAACTACAACTATCTTTAC<br>AGGTTGTTCCGGAAGTCAAATCTGAAGCCCTTTGAACGGGATATCTCAACTGA<br>AATTTATCAAGCCGGATCTACTCCGTGCAATGGAGTCGAAGGATTTAATTGCT<br>ACTTTCCCCTTCAGTCCTATGGTTTTCAACCCACGAATGGCGTCGGTTACCAGC<br>CCTACAGAGTCGTTGTTTTGTCATTCGAACTGCTGCACGCGCCAGCAACGGTA<br>TGCGGCCCCAAGAAAAGCACGAATTTGGTGAAAAATAAATGCGTTAACTTTG<br>GAGGTGGGGGATCCGGCGGAGGAGGTAGTGGAGGGGGAGGCAGTGACAAAA<br>CACACACCTGTCCGCCCTGCCCCGCCCCTGAGCTCCTGGGGGGACCTAGCGTC<br>TTTTTGTTTCCACCAAAGCCCAAAGACACACTTATGATATCTCGGACACCGGA<br>AGTAACTTGTGTAGTTGTAGACGTATCACATGAGGACCCCGAGGTCAAATTCA<br>ATTGGTACGTCGATGGTGTCGAAGTGCACAATGCAAAAACGAAACCGCGAGA<br>GGAGCAATATAACAGTACGTATCGCGTCGTCAGCGTGTTGACGGTACTCCATC<br>AAGATTGGCTCAATGGAAAGGAGTATAAGTGCAAGGTATCCAACAAGGCCCT<br>TCCCGCACCTATAGAAAAGACGATTTCAAAAGCCAAAGGCCAACCCCGAGAG<br>CCCCAAGTATATACACTCCCACCCTCTCGGGATGAGCTGACGAAAAACCAGGT<br>TAGTCTCACTTGCCTCGTCAAGGGATTTTACCCCTCCGATATAGCGGTGGAGT<br>GGGAGTCCAATGGCCAACCGGAGAACAACTATAAAACGACTCCTCCTGTACT<br>CGATTCAGACGGATCTTTCTTTTTGTACAGTAAGCTTACTGTTGACAAATCCAG<br>GTGGCAACAAGGGAATGTATTCAGCTGTAGTGTAATGCACGAGGCATTGCAC<br>AACCACTACACTCAGAAATCTCTCAGTCTGTCCCCAGGAAAGTAG | Anti-CD3 scFv-<br>RBD-Fc codon-<br>optimized DNA |
| 11 | MDAMKRGLCCVLLLCGAVFVSASEVQLVESGGGLVQPGGSLRLSCAASGFTFNT<br>YAMNWVRQAPGKGLEWVARIRSKYNNYATYYAASVKGRFTISRDDSKNSLYLQ<br>MNSLKTEDTAVYYCARHGNFGNSYVSWFAYWGQGTLVTVSSGGGGSQTVVTQE<br>PSLTVSPGGTVTLTCRSSTGAVTTSNYANWVQQKPGQAPRGLIGGTNKRAPGTPA<br>RFSGSLLGGKAALTLSGVQPEDEAEYYCALWYSNLWVFGGGTKLTVLGGGGSG<br>GGGSGGGGSRVQPTESIVRFPNITNLCPFGEVFNATRFASVYAWNRKRISNCVAD<br>YSVLYNSASFSTFKCYGVSPTKLNDLCFTNVYADSFVIRGDEVRQIAPGQTGKIAD<br>YNYKLPDDFTGCVIAWNSNNLDSKVGGNYNYLYRLFRKSNLKPFERDISTEIYQA<br>GSTPCNGVEGFNCYFPLQSYGFQPTNGVGYQPYRVVVLSFELLHAPATVCGPKKS<br>TNLVKNKCVNF | Anti-CD3<br>scFv[diabody]-<br>RBD protein |

| SEQ ID NO: | Sequence | Description |
|---|---|---|
| 12 | ATGGATGCAATGAAGAGAGGGCTCTGCTGTGTGCTGCTGCTGTGTGGAGCAGT<br>CTTCGTTTCGGCTAGCGAAGTCCAACTTGTCGAATCAGGTGGGGGACTGGTAC<br>AACCAGGGGGCTCCCTCCGCCTTAGCTGCGCAGCGTCCGGGTTCACGTTTAAC<br>ACTTACGCAATGAACTGGGTCCGGCAAGCCACCCGGTAAAGGTTTGGAGTGGG<br>TGGCACGCATTAGATCCAAATACAACAATTATGCTACGTACTATGCGGCTAGT<br>GTGAAGGGAAGGTTTACTATATCAAGAGATGACAGTAAAAACAGTCTCTACC<br>TCCAGATGAACTCACTGAAAACCGAGGATACCGCAGTCTATTATTGCGCGCGC<br>CACGGTAATTTTGGCAATTCTTACGTGAGCTGGTTTGCTTACTGGGGCCAGGG<br>GACTCTCGTCACCGTCAGCTCTGGTGGTGGTGGTAGCCAGACGGTAGTTACTC<br>AGGAGCCAAGCCTGACGGTCAGTCCGGGCGGAACAGTTACCCTGACATGCAG<br>GTCTTCCACCGGGCGGTCACCACTTCTAACTATGCGAACTGGGTACAACAGA<br>AACCAGGACAAGCACCCAGAGGGCTTATCGGGGGCACGAATAAACGAGCACC<br>TGGAACTCCGGCAAGGTTCTCTGGAAGCCTGCTTGGGGGCAAGGCGGCGCTC<br>ACTCTTTCAGGTGTGCAACCGGAAGACGAAGCAGAATATTACTGTGCATTGTG<br>GTACTCCAACCTCTGGGTGTTCGGTGGCGGACCAAACTCACAGTGCTGGGCG<br>GTGGTGGGAGCGGGGTGGGGGTTCTGGTGGTGGAGGTAGCCGAGTGCAGCC<br>GACGGAGTCAATCGTGAGATTCCCTAACATAACTAATTTGTGTCCATTTGGCG<br>AAGTGTTCAATGCAACCAGATTCGCCTCCGTCTATGCGTGGAATCGAAAAGA<br>ATTTCAAACTGCGTAGCGGATTATTCTGTCTTGTACAATAGTGCCTCCTTTAGT<br>ACGTTCAAGTGTTATGGGGTGTCACCAACGAAGTTAATGATCTTTGTTTCAC<br>GAATGTTTACGCTGATTCATTTGTAATACGCGGAGACGAAGTTAGACAAATCG<br>CACCAGGGCAGACAGGCAAGATCGCGGATTATAATTATAAGCTGCCAGACGA<br>CTTCACTGGGTGCGTTATCGCATGGAACTCCAACAACTTGGATAGTAAAGTGG<br>GCGGGAATTACAACTACCTGTATAGACTTTTCCGAAAGTCCAATTTGAAGCCA<br>TTCGAAAGGGACATTTCTACTGAAATATATCAAGCGGGATCAACACCTTGCAA<br>CGGAGTGGAAGGGTTCAACTGCTACTTTCCGCTGCAATCTTATGGGTTTCAAC<br>CGACTAATGGAGTCGGGTATCAGCCTTACAGAGTTGTTGTTCTTTCCTTTGAGC<br>TGTTGCATGCCCCGGCAACCGTATGTGGGCCCAAGAAATCTACAAACCTCGTT<br>AAGAATAAATGCGTGAATTTCTAG | Anti-CD3 scFv[diabody]-RBD codon-optimized DNA |
| 13 | MDAMKRGLCCVLLLCGAVF -continued

| SEQ ID NO: | Sequence | Description |
|---|---|---|
| | TQSPPSLLVTLGQPASISCRSSQSLLHSSGNTYLNWLLQRPGQSPQPLIYLVSKLES<br>GVPDRFSGSGSGTDFTLKISGVEAEDVGVYYCMQFTHYPYTFGQGTKLEIKGGGG<br>SGGGGSGGGGSRVQPTESIVRFPNITNLCPFGEVFNATRFASVYAWNRKRISNCVA<br>DYSVLYNSASFSTFKCYGVSPTKLNDLCFTNVYADSFVIRGDEVRQIAPGQTGKIA<br>DYNYKLPDDFTGCVIAWNSNNLDSKVGGNYNYLYRLFRKSNLKPFERDISTEIYQ<br>AGSTPCNGVEGFNCYFPLQSYGFQPTNGVGYQPYRVVVLSFELLHAPATVCGPKK<br>STNLVKNKCVNF | |
| 16 | ATGGATGCAATGAAGAGAGGGCTCTGCTGTGTGCTGCTGCTGTGTGGAGCAGT<br>CTTCGTTTCGGCTAGCCAGGTCCAACTTGTTCAATCAGGAGCTGAGGTACAGC<br>GACCGGGGGCATCTGTTAAGGTCAGTTGCAAAGCTTCAGGCTATATATTCACT<br>GAATACTATATGTATTGGGTCCGGCAAGCACCTGGGCAGGGCCTGGAACTCGT<br>CGGTAGAATTGACCCTGAGGATGGCTCTATTGACTATGTCGAAAAATTTAAAA<br>AAAAAGTGACGCTCACAGCGGACACTAGCAGCTCAACTGCTTACATGGAGCT<br>TTCCAGCTTGACCTCTGATGATACTGCGGTCTACTACTGTGCGCGAGGGAAGT<br>TTAACTATAGGTTTGCATACTGGGGCCAAGGAACGCTGGTAACCGTCAGTTCA<br>GGAGGTGGAGGAAGCGGCGGTGGAGGGAGCGGAGGCGGAGGTAGCGATGTG<br>GTGATGACTCAATCTCCACCTTCCCTGCTCGTAACGCTCGGCCAACCAGCCTC<br>CATAAGCTGTCGGTCCTCACAGAGCCTGCTCCATTCTTCTGGTAACACTTATCT<br>TAACTGGCTTCTGCAAAGACCGGGTCAATCACCCCAACCTCTTATCTATCTGG<br>TATCTAAACTGGAATCCGGGGTTCCCGATCGATTCAGCGGGTCAGGCAGTGGA<br>ACGGACTTTACCTTGAAAATTTCAGGGGTAGAGGCGGAAGACGTAGGGGTCT<br>ACTACTGTATGCAATTCACTCATTACCCGTATACGTTTGGACAAGGGACTAAG<br>CTGGAAATTAAAGGCGGGGGAGGTTCTGGGGGAGGTGGGAGCGGGGGAGGG<br>GGTTCCCGAGTGCAGCCGACGGAGTCAATCGTGAGATTCCCTAACATAACTAA<br>TTTGTGTCCATTTGGCGAAGTGTTCAATGCAACCAGATTCGCCTCCGTCTATGC<br>GTGGAATCGAAAAAGAATTTCAAACTGCGTAGCGGATTATTCTGTCTTGTACA<br>ATAGTGCCTCCTTTAGTACGTTCAAGTGTTATGGGGTGTCACCAACGAAGTTG<br>AATGATCTTTGTTTCACGAATGTTTACGCTGATTCATTTGTAATACGCGGAGAC<br>GAAGTTAGACAAATCGCACCAGGGCAGACAGGCAAGATCGCGGATTATAATT<br>ATAAGCTGCCAGACGACTTCACTGGGTGCGTTATCGCATGGAACTCCAACAAC<br>TTGGATAGTAAAGTGGGCGGGAATTACAACTACCTGTATAGACTTTTCCGAAA<br>GTCCAATTTGAAGCCATTCGAAAGGGACATTTCTACTGAAATATATCAAGCGG<br>GATCAACACCTTGCAACGGAGTGGAAGGGTTCAACTGCTACTTTCCGCTGCAA<br>TCTTATGGGTTTCAACCGACTAATGGAGTCGGGTATCAGCCTTACAGAGTTGT<br>TGTTCTTTCCTTTGAGCTGTTGCATGCCCCGGCAACCGTATGTGGGCCCAAGA<br>AATCTACAAACCTCGTTAAGAATAAATGCGTGAATTTCTAG | Anti-CD2 scFv-RBD codon-optimized DNA |
| 17 | MDAMKRGLCCVLLLCGAVFVSASQVQLVQSGAEVQRPGASVKVSCKASGYIFTE<br>YYMYWVRQAPGQGLELVGRIDPEDGSIDYVEKFKKKVTLTADTSSSTAYMELSS<br>LTSDDTAVYYCARGKFNYRFAYWGQGTLVTVSSGGGGSDVVMTQSPPSLLVTLG<br>QPASISCRSSQSLLHSSGNTYLNWLLQRPGQSPQPLIYLVSKLESGVPDRFSGSGSG<br>TDFTLKISGVEAEDVGVYYCMQFTHYPYTFGQGTKLEIKGGGGSGGGGSGGGGS<br>RVQPTESIVRFPNITNLCPFGEVFNATRFASVYAWNRKRISNCVADYSVLYNSASF<br>STFKCYGVSPTKLNDLCFTNVYADSFVIRGDEVRQIAPGQTGKIADYNYKLPDDF<br>TGCVIAWNSNNLDSKVGGNYNYLYRLFRKSNLKPFERDISTEIYQAGSTPCNGVE<br>GFNCYFPLQSYGFQPTNGVGYQPYRVVVLSFELLHAPATVCGPKKSTNLVKNKC<br>VNF | Anti-CD2 scFv[diabody]-RBD protein |
| 18 | ATGGATGCAATGAAGAGAGGGCTCTGCTGTGTGCTGCTGCTGTGTGGAGCAGT<br>CTTCGTTTCGGCTAGCCAGGTGCAACTTGTTCAGAGTGGTGCGGAGGTTCAGC<br>GACCCGGCGCGAGCGTAAAGGTGAGCTGCAAGGCTAGCGGTTATATTTTTACT<br>GAGTATTATATGTATTGGGTTCGGCAAGCTCCTGGCCAAGGGCTCGAACTCGT<br>AGGCAGAATTGACCCAGAGGACGGCAGTATCGATTATGTAGAGAAGTTCAAA<br>AAGAAGGTAACACTTACAGCAGATACGTCAAGTTCCACTGCGTACATGGAAC<br>TCTCAAGTCTGACCAGTGATGATACAGCAGTTTACTATTGTGCGCGGGGTAAG<br>TTCAATTATAGGTTTGCGTACTGGGGACAAGGTACACTGGTTACCGTCAGCTC<br>TGGAGGTGGTGGGAGCGACGTCGTTATGACTCAGAGTCCGCCATCACTCCTGG<br>TGACGCTGGGTCAACCAGCTTCTATCAGTTGCCGGAGCTCCCAGTCACTCCTG<br>CATTCATCAGGGAACACGTACCTGAATTGGCTCCTTCAGCGGCCAGGACAATC<br>TCCCCAACCTCTGATTTATCTTGTTTCCAAGCTTGAGAGCGGCGTCCCAGATCG<br>ATTTTCTGGGTCCGGTAGTGGTACGGACTTCACTTTGAAAATATCCGGGGTTG<br>AAGCAGAAGACGTTGGGGTTTACTATTGCATGCAGTTCACACATTATCCGTAT<br>ACATTTGGGCAAGGGACCAAACTTGAAATAAAAGGGGGCGGCGGATCTGGGG<br>GTGGTGGTAGTGGTGGTGGTGGCTCTCGAGTGCAGCCGACGGAGTCAATCGTG<br>AGATTCCCTAACATAACTAATTTGTGTCCATTTGGCGAAGTGTTCAATGCAAC<br>CAGATTCGCCTCCGTCTATGCGTGGAATCGAAAAAGAATTTCAAACTGCGTAG<br>CGGATTATTCTGTCTTGTACAATAGTGCCTCCTTTAGTACGTTCAAGTGTTATG<br>GGGTGTCACCAACGAAGTTGAATGATCTTTGTTTCACGAATGTTTACGCTGAT<br>TCATTTGTAATACGCGGAGACGAAGTTAGACAAATCGCACCAGGGCAGACAG<br>GCAAGATCGCGGATTATAATTATAAGCTGCCAGACGACTTCACTGGGTGCGTT<br>ATCGCATGGAACTCCAACAACTTGGATAGTAAAGTGGGCGGGAATTACAACT<br>ACCTGTATAGACTTTTCCGAAAGTCCAATTTGAAGCCATTCGAAAGGGACATT<br>TCTACTGAAATATATCAAGCGGGATCAACACCTTGCAACGGAGTGGAAGGGT<br>TCAACTGCTACTTTCCGCTGCAATCTTATGGGTTTCAACCGACTAATGGAGTCG | Anti-CD2 scFv[diabody]-RBD codon-optimized DNA |

-continued

| SEQ ID NO: | Sequence | Description |
|---|---|---|
| | GGTATCAGCCTTACAGAGTTGTTGTTCTTTCCTTTGAGCTGTTGCATGCCCCGG CAACCGTATGTGGGCCCAAGAAATCTACAAACCTCGTTAAGAATAAATGCGT GAATTTCTAG | |
| 19 | MDAMKRGLCCVLLLCGAVFVSASQVQLVQSGAEVQRPGASVKVSCKASGYIFTE YYMYWVRQAPGQGLELVGRIDPEDGSIDYVEKFKKKVTLTADTSSSTAYMELSS LTSCDTAVYYCARGKFNYRFAYWGQGTLVTVSSGGGGSDVVMTQSPPSLLVTLG QPASISCRSSQSLLHSSGNTYLNWLLQRPGQSPQPLIYLVSKLESGVPDRFSGSGSG TDFTLKISGVEAEDVGVYYCMQFTHYPYTFGQGTKLEIKGGGGSGGGGSGGGGS RVQPTESIVRFPNITNLCPFGEVFNATRFASVYAWNRKRISNCVADYSVLYNSASF STFKCYGVSPTKLNDLCFTNVYADSFVIRGDEVRQIAPGQTGKIADYNYKLPDDF TGCVIAWNSNNLDSKVGGNYNYLYRLFRKSNLKPFERDISTEIYQAGSTPCNGVE GFNCYFPLQSYGFQPTNGVGYQPYRVVVLSFELLHAPATVCGPKKSTNLVKNKC VNF | Anti-CD2 scFv[enhanced Diabody]-RBD protein |
| 20 | ATGGATGCAATGAAGAGAGGGCTCTGCTGTGTGCTGCTGCTGTGTGGAGCAGT CTTCGTTTCGGCTAGCCAGGTCCAGCTCGTACAAAGCGGAGCTGAAGTCCAGA GGCCGGGAGCGAGCGTAAAGGTCTCTTGTAAAGCCTCTGGATACATTTTTACG GAGTACTACATGTATTGGGTTAGGCAGGCACCTGGTCAAGGTTTGGAATTGGT CGGGAGAATAGACCCTGAAGATGGGTCAATAGATTATGTCGAAAAATTCAAG AAGAAAGTAACCCTCACAGCAGATACAAGCTCAAGCACTGCTTATATGGAAC TTTCTAGCCTCACCTCTTGCGACACCGCAGTTTATTACTGTGCCAGAGGGAAA TTTAATTACAGGTTTGCCTACTGGGGACAAGGAACGTTGGTAACGGTATCATC CGGCGGTGGTGGATCAGACGTGGTTATGACACAGTCCCCACCGAGCTTGCTTG TTACTCTCGGGCAGCCTGCCAGCATCTCATGCAGATCATCTCAGAGCCTTCTTC ATTCATCTGGCAACACCTACCTTAATTGGCTGCTCCAACGACCGGGTCAGTCC CCCCAACCCTTGATATACTTGGTTAGTAAACTCGAAAGTGGAGTTCCGGACAG ATTCTCTGGATCTGGAAGCGGAACTGATTTTACCCTCAAGATATCCGGCGTAG AGGCGGAAGATGTCGGGGTTTACTATTGTATGCAATTTACTCATTACCCGTAC ACTTTTGGTCAGGGCACAAAGCTCGAAATTAAAGGAGGAGGAGGTTCTGGAG GCGGGGGCAGCGGTGGTGGAGGTTCCCGAGTGCAGCCGACGGAGTCAATCGT GAGATTCCCTAACATAACTAATTTGTGTCCATTTGGCGAAGTGTTCAATGCAA CCAGATTCGCCTCCGTCTATGCGTGGAATCGAAAAAGAATTTCAAACTGCGTA GCGGATTATTCTGTCTTGTACAATAGTGCCTCCTTTAGTACGTTCAAGTGTTAT GGGGTGTCACCAACGAAGTTGAATGATCTTTGTTTCACGAATGTTTACGCTGA TTCATTTGTAATACGCGGAGACGAAGTTAGACAAATCGCACCAGGGCAGACA GGCAAGATCGCGGATTATAATTATAAGCTGCCAGACGACTTCACTGGGTGCGT TATCGCATGGAACTCCAACAACTTGGATAGTAAAGTGGGCGGGAATTACAAC TACCTGTATAGACTTTTCCGAAAGTCCAATTTGAAGCCATTCGAAAGGGACAT TTCTACTGAAATATATCAAGCGGGATCAACACCTTGCAACGGAGTGGAAGGG TTCAACTGCTACTTTCCGCTGCAATCTTATGGGTTTCAACCGACTAATGGAGTC GGGTATCAGCCTTACAGAGTTGTTGTTCTTTCCTTTGAGCTGTTGCATGCCCCG GCAACCGTATGTGGGCCCAAGAAATCTACAAACCTCGTTAAGAATAAATGCG TGAATTTCTAG | Anti-CD2 scFv[enhanced Diabody]-RBD codon-optimized DNA |
| 21 | MDAMKRGLCCVLLLCGAVFVSASFSQQIYGVVYGNVTFHVPSNVPLKEVLWKK QKDKVAELENSEFRAFSSFKNRVYLDTVSGSLTIYNLTSSDEDEYEMESPNITDTM KFFLYVLESGGGGSGGGGSGGGGSRVQPTESIVRFPNITNLCPFGEVFNATRFASV YAWNRKRISNCVADYSVLYNSASFSTFKCYGVSPTKLNDLCFTNVYADSFVIRGD EVRQIAPGQTGKIADYNYKLPDDFTGCVIAWNSNNLDSKVGGNYNYLYRLFRKS NLKPFERDISTEIYQAGSTPCNGVEGFNCYFPLQSYGFQPTNGVGYQPYRVVVLSF ELLHAPATVCGPKKSTNLVKNKCVNF | 1dCD58-RBD protein |
| 22 | ATGGATGCAATGAAGAGAGGGCTCTGCTGTGTGCTGCTGCTGTGTGGAGCAGT CTTCGTTTCGGCTAGCTTCAGTCAGCAAATCTACGGTGTCGTGTATGGCAATGT GACATTTCACGTGCCGAGTAACGTCCCTCTCAAGGAGGTTTTGTGGAAGAAGC AGAAGGATAAGGTGGCCGAGCTGGAGAACTCTGAGTTTCGGGCTTTCTCCTCT TTCAAAAATCGAGTATACCTCGATACAGTCAGTGGGTCTCTGACCATATATAA CCTTACTTCCTCTGATGAGGACGAATATGAGATGGAATCTCCGAACATAACAG ATACTATGAAGTTCTTCCTCTATGTACTCGAATCAGGGGGTGGTGGGTCTGGA GGGGGCGGTTCAGGGGGAGGCGGGAGTCGAGTGCAGCCGACGGAGTCAATCG TGAGATTCCCTAACATAACTAATTTGTGTCCATTTGGCGAAGTGTTCAATGCA ACCAGATTCGCCTCCGTCTATGCGTGGAATCGAAAAAGAATTTCAAACTGCGT AGCGGATTATTCTGTCTTGTACAATAGTGCCTCCTTTAGTACGTTCAAGTGTTA TGGGGTGTCACCAACGAAGTTGAATGATCTTTGTTTCACGAATGTTTACGCTG ATTCATTTGTAATACGCGGAGACGAAGTTAGACAAATCGCACCAGGGCAGAC AGGCAAGATCGCGGATTATAATTATAAGCTGCCAGACGACTTCACTGGGTGCG TTATCGCATGGAACTCCAACAACTTGGATAGTAAAGTGGGCGGGAATTACAA CTACCTGTATAGACTTTTCCGAAAGTCCAATTTGAAGCCATTCGAAAGGGACA TTTCTACTGAAATATATCAAGCGGGATCAACACCTTGCAACGGAGTGGAAGG GTTCAACTGCTACTTTCCGCTGCAATCTTATGGGTTTCAACCGACTAATGGAGT CGGGTATCAGCCTTACAGAGTTGTTGTTCTTTCCTTTGAGCTGTTGCATGCCCC GGCAACCGTATGTGGGCCCAAGAAATCTACAAACCTCGTTAAGAATAAATGC GTGAATTTCTAG | 1dCD58-RBD codon-optimized DNA |

-continued

| SEQ ID NO: | Sequence | Description |
|---|---|---|
| 23 | MDAMKRGLCCVLLLCGAVFVSASFSQQIYGVVYGNVTFHVPSNVPLKEVLWKK QKDKVAELENSEFRAFSSFKNRVYLDTVSGSLTIYNLTSSDEDEYEMESPNITDTM KFFLYVLESGGGGSGGGGSGGGGSRVQPTESIVRFPNITNLCPFGEVFNATRFASV YAWNRKRISNCVADYSVLYNSASFSTFKCYGVSPTKLNDLCFTNVYADSFVIRGD EVRQIAPGQTGNIADYNYKLPDDFTGCVIAWNSNNLDSKVGGNYNYLYRLFRKS NLKPFERDISTEIYQAGSTPCNGVKGFNCYFPLQSYGFQPTYGVGYQPYRVVVLSF ELLHAPATVCGPKKSTNLVKNKCVNF | 1dCD58-RBDsa protein |
| 24 | ATGGATGCAATGAAGAGAGGGCTCTGCTGTGTGCTGCTGCTGTGTGGAGCAGT CTTCGTTTCGGCTAGCTTCAGTCAGCAAATCTACGGTGTCGTGTATGGCAATGT GACATTTCACGTGCCGAGTAACGTCCCTCTCAAGGAGGTTTTGTGGAAGAAGC AGAAGGATAAGGTGGCCGAGCTGGAGAACTCTGAGTTTCGGGCTTTCTCCTCT TTCAAAAATCGAGTATACCTCGATACAGTCAGTGGGTCTCTGACCATATATAA CCTTACTTCCTCTGATGAGGACGAATATGAGATGGAATCTCCGAACATAACAG ATACTATGAAGTTCTTCCTCTATGTACTCGAATCAGGGGGTGGTGGGTCTGGA GGGGGCGGTTCAGGGGGAGGCGGGAGTCGAGTGCAGCCGACGGAGTCAATCG TGAGATTCCCTAACATAACTAATTTGTGTCCATTTGGCGAAGTGTTCAATGCA ACCAGATTCGCCTCCGTCTATGCGTGGAATCGAAAAAGAATTTCAAACTGCGT AGCGGATTATTCTGTCTTGTACAATAGTGCCTCCTTTAGTACGTTCAAGTGTTA TGGGGTGTCACCAACGAAGTTGAATGATCTTTGTTTCACGAATGTTTACGCTG ATTCATTTGTAATACGCGGAGACGAAGTTAGACAAATCGCACCAGGGCAGAC AGGCAACATCGCGGATTATAATTATAAGCTGCCAGACGACTTCACTGGGTGCG TTATCGCATGGAACTCCAACAACTTGGATAGTAAAGTGGGCGGGAATTACAA CTACCTGTATAGACTTTTCCGAAAGTCCAATTTGAAGCCATTCGAAAGGGACA TTTCTACTGAAATATATCAAGCGGGATCAACACCTTGCAACGGAGTGAAAGG GTTCAACTGCTACTTTCCGCTGCAATCTTATGGGTTTCAACCGACTTATGGAGT CGGGTATCAGCCTTACAGAGTTGTTGTTCTTTCCTTTGAGCTGTTGCATGCCCC GGCAACCGTATGTGGGCCCAAGAAATCTACAAACCTCGTTAAGAATAAATGC GTGAATTTCTAG | 1dCD58-RBDsa codon-optimized DNA |
| 25 | MDAMKRGLCCVLLLCGAVFVSASEVQLVESGGGLVQPGGSLRLSCAASGFTFNT YAMNWVRQAPGKGLEWVARIRSKYNNYATYYAASVKGRFTISRDDSKNSLYLQ MNSLKTEDTAVYYCARHGNFGNSYVSWFAYWGQGTLVTVSSGGGGSGGGGSG GGGSQTVVTQEPSLTVSPGGTVTLTCRSSTGAVTTSNYANWVQQKPGQAPRGLIG GTNKRAPGTPARFSGSLLGGKAALTLSGVQPEDEAEYYCALWYSNLWVFGGGTK LTVLGGGGSGGGGSGGGGSRVQPTESIVRFPNITNLCPFGEVFNATRFASVYAWN RKRISNCVADYSVLYNSASFSTFKCYGVSPTKLNDLCFTNVYADSFVIRGDEVRQI APGQTGNIADYNYKLPDDFTGCVIAWNSNNLDSKVGGNYNYLYRLFRKSNLKPF ERDISTEIYQAGSTPCNGVKGFNCYFPLQSYGFQPTYGVGYQPYRVVVLSFELLHA PATVCGPKKSTNLVKNKCVNFNAVGQDTQEVIVVPHSLPFKVVVISAILALVVLTI ISLIILIMLWQKKPR | Anti-CD3 scFv-RBD(B.1.351)-PDGFRtm protein |
| 26 | ATGGACGCTATGAAGAGGGGTCTCTGCTGTGTCCTCCTTCTGTGCGGTGCCGT CTTTGTGTCTGCCTCTGAAGTACAATTGGTGGAGTCTGGGGGAGGCCTTGTCC AACCAGGCGGGTCTTTGCGACTGTCATGCGCCGCCTCTGGGTTTACATTCAAC ACATATGCTATGAATTGGGTCCGACAAGCGCCGGGCAAAGGACTGGAATGGG TCGCCCGCATTCGCTCAAAGTATAACAATTATGCCACATATTACGCTGCGTCA GTGAAAGGACGGTTCACAATATCACGAGACGATTCTAAAAACTCACTGTATCT CCAAATGAATAGCCTCAAAACGGAGGACACTGCAGTCTATTATTGCGCTCGAC ATGGCAATTTTGGAAATAGCTATGTATCCTGGTTTGCGTACTGGGGCCAAGGG ACGCTGGTGACTGTTTCAAGCGGTGGCGGCGGATCCGGTGGAGGAGGCAGCG GCGGTGGTGGCTCCCAAACCGTTGTCACCCAAGAGCCTTCTCTCACAGTGTCC CCTGGTGGCACAGTGACTTTGACTTGTAGGTCTTCTACAGGCGCGGTCACGAC CAGTAATTATGCTAATTGGGTCCAGCAGAAACCGGGGCAGGCGCCAAGAGGT CTCATAGGGGGGACAAATAAACGCGCGCCGGGTACGCCTGCACGATTCAGCG GATCCTTGCTGGGCGGCAAGGCAGCCCTTACGCTCTCCGGGGTTCAGCCCGAA GACGAGGCAGAATACTATTGTGCGCTGTGGTATAGTAATCTTTGGGTATTTGG AGGAGGTACAAAATTGACCGTGTTGGGTGGAGGAGGATCCGGGGGAGGCGGA AGCGGGGGTGGCGGTTCTCGAGTGCAGCCGACGGAGTCAATCGTGAGATTCC CTAACATAACTAATTTGTGTCCATTTGGCGAAGTGTTCAATGCAACCAGATTC GCCTCCGTCTATGCGTGGAATCGAAAAAGAATTTCAAACTGCGTAGCGGATTA TTCTGTCTTGTACAATAGTGCCTCCTTTAGTACGTTCAAGTGTTATGGGGTGTC ACCAACGAAGTTGAATGATCTTTGTTTCACGAATGTTTACGCTGATTCATTTGT AATACGCGGAGACGAAGTTAGACAAATCGCACCAGGGCAGACAGGCAACATC GCGGATTATAATTATAAGCTGCCAGACGACTTCACTGGGTGCGTTATCGCATG GAACTCCAACAACTTGGATAGTAAAGTGGGCGGGAATTACAACTACCTGTAT AGACTTTTCCGAAAGTCCAATTTGAAGCCATTCGAAAGGGACATTTCTACTGA AATATATCAAGCGGGATCAACACCTTGCAACGGAGTGAAAGGGTTCAACTGC TACTTTCCGCTGCAATCTTATGGGTTTCAACCGACTTATGGAGTCGGGTATCAG CCTTACAGAGTTGTTGTTCTTTCCTTTGAGCTGTTGCATGCCCCGGCAACCGTA TGTGGGCCCAAGAAATCTACAAACCTCGTTAAGAATAAATGCGTGAATTTCAA CGCTGTGGGGCAAGATACTCAGGAGGTCATCGTTGTCCCACATTCACTGCCTT TTAAGGTCGTTGTGATATCCGCAATTCTTGCGCTGGTGGTACTTACAATAATA AGCCTCATAATCCTTATAATGCTCTGGCAAAAGAAGCCACGCTAG | Anti-CD3 scFv-RBD(B.1.351)-PDGFRtm codon-optimized DNA |

-continued

| SEQ ID NO: | Sequence | Description |
|---|---|---|
| 27 | MDAMKRGLCCVLLLCGAVFVSASQVQLQQSGPEVVKPGASVKMSCKASGYTFT<br>SYVIHWVRQKPGQGLDWIGYINPYNDGTDYDEKFKGKATLTSDTSTSTAYMELS<br>SLRSEDTAVYYCAREKDNYATGAWFAYWGQGTLVTVSSGGGGSGGGGSGGGGS<br>DIVMTQSPDSLAVSLGERVTMNCKSSQSLLYSTNQKNYLAWYQQKPGQSPKLLIY<br>WASTRESGVPDRFSGSGSGTDFTLTISSVQAEDVAVYYCQQYYSYRTFGGGTKLE<br>IKGGGGSGGGGSGGGGSRVQPTESIVRFPNITNLCPFGEVFNATRFASVYAWNRK<br>RISNCVADYSVLYNSASFSTFKCYGVSPTKLNDLCFTNVYADSFVIRGDEVRQIAP<br>GQTGKIADYNYKLPDDFTGCVIAWNSNNLDSKVGGNYNYLYRLFRKSNLKPFER<br>DISTEIYQAGSTPCNGVEGFNCYFPLQSYGFQPTNGVGYQPYRVVVLSFELLHAPA<br>TVCGPKKSTNLVKNKCVN | Anti-CD4 scFv-RBD protein |
| 28 | ATGGATGCAATGAAGAGAGGGCTCTGCTGTGTGCTGCTGCTGTGTGGAGCAGT<br>CTTCGTTTCGGCTAGCCAGGTACAGCTCCAACAGTCCGGTCCAGAGGTCGTGA<br>AACCTGGTGCATCCGTTAAAATGAGTTGCAAAGCTTCCGGTTATACGTTCACA<br>TCTTACGTTATCCATTGGGTTCGCCAGAAACCGGGTCAGGGACTTGACTGGAT<br>CGGTTATATAAATCCGTACAATGATGGCACCGACTACGACGAGAAATTCAAA<br>GGAAAGGCTACACTTACGTCTGATACGAGTACCTCAACTGCTTACATGGAACT<br>TTCCTCTTTGAGGTCTGAAGACACGGCAGTTTACTATTGTGCCAGAGAAAAAG<br>ATAATTATGCCACGGGAGCTTGGTTCGCATACTGGGGGCAAGGAACATTGGTT<br>ACGGTAAGTAGTGGGGGAGGCGGAAGTGGGGGCGGAGGCTCAGGTGGTGGG<br>GGTTCAGATATTGTGATGACACAGAGCCCGGACAGTCTTGCAGTGAGTCTCGG<br>CGAACGCGTTACCATGAATTGTAAGAGTAGTCAGTCTCTCTTGTATAGCACTA<br>ATCAAAAGAATTATTTGGCATGGTACCAACAGAAGCCGGGTCAGTCTCCTAAA<br>CTGCTGATTTACTGGGCGTCAACACGGGAGTCTGGAGTTCCGGATCGATTCTC<br>CGGATCTGGAAGCGGTACTGACTTCACCCTCACGATCTCAAGTGTGCAAGCGG<br>AGGACGTTGCGGTGTATTACTGCCAACAGTATTATTCTTACCGAACATTCGGC<br>GGTGGGACCAAGCTGGAAATAAAAGGGGGTGGCGGCAGTGGCGGTGGCGGG<br>TCTGGAGGTGGGGGTTCCCGAGTGCAGCCGACGGAGTCAATCGTGAGATTCCC<br>TAACATAACTAATTTGTGTCCATTTGGCGAAGTGTTCAATGCAACCAGATTCG<br>CCTCCGTCTATGCGTGGAATCGAAAAAGAATTTCAAACTGCGTAGCGGATTAT<br>TCTGTCTTGTACAATAGTGCCTCCTTTAGTACGTTCAAGTGTTATGGGGTGTCA<br>CCAACGAAGTTGAATGATCTTTGTTTCACGAATGTTTACGCTGATTCATTTGTA<br>ATACGCGGAGACGAAGTTAGACAAATCGCACCAGGGCAGACAGGCAAGATCG<br>CGGATTATAATTATAAGCTGCCAGACGACTTCACTGGGTGCGTTATCGCATGG<br>AACTCCAACAACTTGGATAGTAAAGTGGGCGGGAATTACAACTACCTGTATA<br>GACTTTTCCGAAAGTCCAATTTGAAGCCATTCGAAAGGACATTTCTACTGAA<br>ATATATCAAGCGGGATCAACACCTTGCAACGGAGTGGAAGGGTTCAACTGCT<br>ACTTTCCGCTGCAATCTTATGGGTTTCAACCGACTAATGGAGTCGGGTATCAG<br>CCTTACAGAGTTGTTGTTCTTTCCTTTGAGCTGTTGCATGCCCCGGCAACCGTA<br>TGTGGGCCCAAGAAATCTACAAACCTCGTTAAGAATAAATGCGTGAATTTCTA<br>G | Anti-CD4 scFv-RBD codon-optimized DNA |

SEQUENCE LISTING

```
Sequence total quantity: 29
SEQ ID NO: 1            moltype = AA  length = 962
FEATURE                 Location/Qualifiers
REGION                  1..962
                        note = Description of Artificial Sequence: Synthetic
                         polypeptide
source                  1..962
                        mol_type = protein
                        organism = synthetic construct
SEQUENCE: 1
MDAMKRGLCC VLLLCGAVFV SASEVQLVES GGGLVQPGGS LRLSCAASGF TFNTYAMNWV  60
RQAPGKGLEW VARIRSKYNN YATYYAASVK GRFTISRDDS KNSLYLQMNS LKTEDTAVYY  120
CARHGNFGNS YVSWFAYWGQ GTLVTVSSGG GGSGGGGSGG GGSQTVVTQE PSLTVSPGGT  180
VTLTCRSSTG AVTTSNYANW VQQKPGQAPR GLIGGTNKRA PGTPARFSGS LLGGKAALTL  240
SGVQPEDEAE YYCALWYSNL WVFGGGTKLT VLGGGGSGGG GSGGGGSVNL TTRTQLPPAY  300
TNSFTRGVYY PDKVFRSSVL HSTQDLFLPF FSNVTWFHAI HVSGTNGTKR FDNPVLPFND  360
GVYFASTEKS NIIRGWIFGT TLDSKTQSLL IVNNATNVVI KVCEFQFCND PFLGVYYHKN  420
NKSWMESEFR VYSSANNCTF EYVSQPFLMD LEGKQGNFKN LREFVFKNID GYFKIYSKHT  480
PINLVRDLPQ GFSALEPLVD LPIGINITRF QTLLALHRSY LTPGDSSSGW TAGAAAYYVG  540
YLQPRTFLLK YNENGTITDA VDCALDPLSE TKCTLKSFTV EKGIYQTSNF RVQPTESIVR  600
FPNITNLCPF GEVFNATRFA SVYAWNRKRI SNCVADYSVL YNSASFSTFK CYGVSPTKLN  660
DLCFTNVYAD SFVIRGDEVR QIAPGQTGKI ADYNYKLPDD FTGCVIAWNS NNLDSKVGGN  720
YNYLYRLFRK SNLKPFERDI STEIYQAGST PCNGVEGFNC YFPLQSYGFQ PTNGVGYQPY  780
RVVVLSFELL HAPATVCGPK KSTNLVKNKC VNFNFNGLTG TGVLTESNKK FLPFQQFGRD  840
IADTTDAVRD PQTLEILDIT PCSFGGVSVI TPGTNTSNQV AVLYQDVNCT EVPVAIHADQ  900
LTPTWRVYST GSNVFQTRAG CLIGAEHVNN SYECDIPIGA GICASYQTQT NSPRRARSVA  960
SQ                                                                 962
```

```
SEQ ID NO: 2            moltype = DNA  length = 2889
FEATURE                 Location/Qualifiers
misc_feature            1..2889
                        note = Description of Artificial Sequence: Synthetic
                        polynucleotide
source                  1..2889
                        mol_type = other DNA
                        organism = synthetic construct
SEQUENCE: 2
atggatgcaa tgaagagagg gctctgctgt gtgctgctgc tgtgtggagc agtcttcgtt    60
tcggctagcg aggtgcagct cgttgagagt ggtgggggtc tggtccaacc cggtgggagt   120
ctccgcttgt catgtgcagc ttctggcttc acatttaaca cctatgccat gaactgggtc   180
cggcaggccc ccggcaaggg acttgaatgg gttgcacgga tccgctcaaa atacaacaac   240
tacgcgactt actacgctgc ctcagtcaag ggtcgcttca ccattagtcg cgacgactct   300
aagaatagtc tttatttgca gatgaatagt ctcaagaccg aggacactgc ggtatattat   360
tgcgcacggc acggaaattt tggcaattca tatgttagtt ggttcgctta ctgggggcaa   420
ggcacgctcg ttacggtctc aagtggtggt ggcggttcag gggagggggg ctctggaggg   480
ggcggttctc aaaccgttgt cacccaggaa ccaagcctga ccgtaagccc tggtgggacc   540
gtgactctca cgtgtagaag ttctacagga gctgttacta cctcaaacta cgctaactgg   600
gtacaacaaa aacccggtca agcaccaagg ggactgatag gcgaacaaa caaaagggcg    660
ccgggtactc cggcacgatt ttccggatct cttcttggag gaaaggcagc gttgacttg    720
tctggagttc agcccgagga tgaggcagag tattattgcg cactctggta tagtaacctc   780
tgggtcttcg gcggaggaac taagcttacg gtccttgggg gtgcggcag tggcggtggc    840
gggtctggag gtggggttc cgttaatctc acgaccagga cccaattgcc tccgcgtat     900
actaactctt tcacgagggg agtctactat cctgacaagg tatttaggtc ttcagtgctg   960
catagtacac aagacctgtt ccttccgttt ttcagcaacg tgacttggtt ccacgctata  1020
cacgtctcag gacgaatgg aacaaagcgc ttcgataatc cggttttgcc atttaatgat   1080
ggtgtctatt tcgcatccac agaaaagtcc aacattatca ggggtggat ctttggtacg   1140
acgctggata gcaaaacaca gtccctcctt atcgtcaaca atgccacgaa tgtggtgatt   1200
aaggtttgcg aatttcaatt ttgtaacgac ccttttcttg gcgtatatta tcataaaaac  1260
aacaagtcct ggatgaaag cgaattccgc gtatacagtt ccgcaaacaa ctgtacattt   1320
gaatatgtga gccaaccttt tctgatggac ctggagggca aacagggcaa ctttaaaaat  1380
ttgagagagt tcgtcttcaa aaatattgat ggatatttca agatttatag taagcatacg   1440
cccataaatc ttgtccggga tctgccgcag ggttttagcg ctctcgaacc cttggtagac  1500
ctcccgattg gtataaacat caccaggttt cagaccctttc ttgcgttgca ccgcagctat  1560
ctcacgccag gcgatagtag ttcaggttgg actgccggag cagcagccta ctacgtaggc  1620
taccttcaac ctagaacgtt tctgttgaaa tataatgaaa atggtacaat cacagacgcg  1680
gtcgactgcg cactggaccc gctgagcgaa accaaatgta cgctcaagtc cttcaccgta  1740
gagaaaggca tctaccagac ttctaatttc cgagtgcagc cgacggagtc aatcgtgaga  1800
ttccctaaca taactaattt gtgtccattt ggcgaagtgt tcaatgcaac cagattcgcc  1860
tccgtctatg cgtggaatcg aaaaagaatt tcaaactgcg tagcggatta ttctgtcttg  1920
tacaatagtg cctcctttag tacgttcaag tgtttatgggg tgtcaccaac gaagttgaat  1980
gatctttgtt tcacgaatgt ttacgctgat tcatttgtaa tacgcggaga cgaagttaga  2040
caaatcgcac cagggcagac aggcaagatc gcggattata attataagct gccagacgac  2100
ttcactgggt gcgttatcgc atggaactcc aacaacttgg atagtaaagt gggcgggaat  2160
tacaactacc tgtatagact tttccgaaag tccaatttga agccattcga aagggacatt  2220
tctactgaaa tatatcaagc gggatcaaca ccttgcaacg gagtggaagg gttcaactgc  2280
tactttccgc tgcaatctta tgggtttcaa ccgactaatg gagtcgggta tcagccttac  2340
agagttgttg ttcttttcctt tgagctgttg catgccccgg caaccgtatg tgggcccaag  2400
aaatctacaa acctcgttaa gaataaatgc gtgaatttca acttcaattgg tctcaccggg  2460
acggggtcc tgaccgaaag taacaagaaa tttctgccct tcagcaatt cggaagagac   2520
atcgcggaca ctacagacgc cgttcgggac ccgcagactc tcgaaattct tgacatcacg  2580
ccgtgttcat tcgaggcgt ttccgtgatt acaccaggaa cgaataccag caatcaagtg    2640
gcagtgttgt atcaagtgat taattgcact gaagtgctcg tcgctatcca cgcggaccag  2700
ctcacgccta cgtggagggt tgattcaaca ggaagcaacg tgttccaaac acgagcgggt  2760
tgtcttatag gggcggagca cgtgaacaat agttacgaat gtgatatacc gatagggct   2820
gggatatgtg cgtcttatca aacacagacg aatagcccca ggcgcgctcg aagtgtggca  2880
agccaatag                                                          2889

SEQ ID NO: 3            moltype = DNA  length = 1260
FEATURE                 Location/Qualifiers
misc_feature            1..1260
                        note = Description of Artificial Sequence: Synthetic
                        polynucleotide
source                  1..1260
                        mol_type = other DNA
                        organism = synthetic construct
SEQUENCE: 3
atgagcgata acggccccca gaatcagagg aatgcaccta ggataacatt tggaggtccg     60
tcagacagca ctggctccaa ccagaatggc gagcggtctg gcgcgcggtc taagcaaagg   120
agaccacaag gtctcccgaa taacacggcc tcctggttta cagcgctcac ccagcacggt   180
aaagaggacc tgaagttccc taggggggcaa ggtgtaccga ttaataccaa cagctccccc   240
gatgaccaga ttggttatta tagaaagagct acaagacga tacggggtgg agatgggaag   300
atgaaggacc tctccccctcg gtggtattt tattatctgg gcaccggacc ggaagccggg   360
ctcccctacg cgccaataa ggacggtata atatggtcg ccactgaggg tgccctcaat     420
accccgaagg accacattgg cactcgaaac cggcaaaca acgcagctat tgtcctgcaa    480
ctcccacagg gtaccacgct cccgaaaggt ttttatgccg aagggtctcg cggggggttca   540
caggctagca gtcgaagctc atctcggagc cgaaatagct caaggaattc aacacccgga   600
```

```
agctccagag gcacaagccc tgcgcggatg gcagggaacg gaggcgatgc tgccctggcc   660
ctccttctct tggatagact taatcagctg gaatccaaaa tgtcaggaaa gggccagcaa   720
caacaaggtc agacagtgac caaaaaatcc gccgcagagg ccagtaagaa acctagacag   780
aagcgaactg ctacaaaggc ctataatgta actcaggcgt tcggacggcg aggccctgaa   840
caaacccagg gcaatttcgg tgaccaagaa ctcataagac agggaactga ctacaaacat   900
tggccccaga ttgcacaatt tgccccatcc gcctcagcct tcttcggaat gtctcgcatc   960
gggatggagg taacaccgag cgggacctgg ctcacataca caggtgcgat aaagctcgat  1020
gacaaagatc ccaattttaa agaccaagtg atacttctta ataagcacat agacgcctat  1080
aaaaccttcc cgcccactga gccaaagaaa gacaagaaaa aaaagcgga cgagacacaa  1140
gcccttccgc aaagacagaa aaaacagcaa acggttacat tgcttcctgc ggcagacctg  1200
gatgattttt ccaaacagct tcagcaatct atgtctagcg cagatagtac ccaggcgtaa  1260

SEQ ID NO: 4               moltype = DNA  length = 891
FEATURE                    Location/Qualifiers
misc_feature               1..891
                           note = Description of Artificial Sequence: Synthetic
                           polynucleotide
source                     1..891
                           mol_type = other DNA
                           organism = synthetic construct
SEQUENCE: 4
atggctgaca gcaatgggac gatcacagtc gaggaactca agaaactgtt ggagcagtgg   60
aatttggtga taggcttctt gttcttgacg tggatatgct tgctgcagtt tgcctatgcg  120
aatagaaacc gcttcttgta tataatcaaa ctgatatttc tctggttgct ctggcccgtc  180
acgcttgcat gttttgtttt ggcggccgtt taccggatca actggattac aggggggaatt  240
gcaatagcga tggcatgtct ggtaggattg atgtggctgc tctactttat tcgtcattt  300
cgattgtttg cacgcactcg gtccatgtgg tcctttaatc cagaaaccaa tatactgctc  360
aacgtaccat tgcatgggac tatactgacg cgacctcttt tggaatcaga gctggtgata  420
ggtgcagtga tactgagagg gcatctccga atagcgggggc accacctggg cagatgtgac  480
atcaaagacc ttccaaaaga aatcacggtg gccacgtgac gacattgtc atattacaaa  540
cttggcgcat cccaaagagt agcaggagat tctggtttcg cggcatactc taggtacagg  600
atcgggaatt acaaactgaa cacagatcat ccctctagtt ccgacaacat agcccttttg  660
gtacagatgt actctttcgt atcagaggag actggtactc ttatagttaa ttctgtgctg  720
ctcttttctt cgttttgtcgt ctttctgctt gtaacacttc ctattcttac tgcgttgaga  780
ctctgtgcct attgttgtaa tatagtcaat gtatctttgg taaagctcag tttttatgtg  840
tatagccggg tcaaaaacct taactccagc cgagttcccg accttttggt t            891

SEQ ID NO: 5               moltype = AA  length = 15
FEATURE                    Location/Qualifiers
REGION                     1..15
                           note = Description of Artificial Sequence: Synthetic peptide
source                     1..15
                           mol_type = protein
                           organism = synthetic construct
SEQUENCE: 5
GGGGSGGGGS GGGGS                                                    15

SEQ ID NO: 6               moltype = AA  length = 510
FEATURE                    Location/Qualifiers
REGION                     1..510
                           note = Description of Artificial Sequence: Synthetic
                           polypeptide
source                     1..510
                           mol_type = protein
                           organism = synthetic construct
SEQUENCE: 6
MDAMKRGLCC VLLLCGAVFV SASEVQLVES GGGLVQPGGS LRLSCAASGF TFNTYAMNWV   60
RQAPGKGLEW VARIRSKYNN YATYYAASVK GRFTISRDDS KNSLYLQMNS LKTEDTAVYY  120
CARHGNFGNS YVSWFAYWGQ GTLVTVSSGG GGSGGGGSGG GGSQTVVTQE PSLTVSPGGT  180
VTLTCRSSTG AVTTSNYANW VQQKPGQAPR GLIGGTNKRA PGTPARFSGS LLGGKAALTL  240
SGVQPEDEAE YYCALWYSNL WVFGGGTKLT VLGGGGSGGG GSGGGGSRVQ PTESIVRFPN  300
ITNLCPFGEV FNATRFASVY AWNRKRISNC VADYSVLYNS ASFSTFKCYG VSPTKLNDLC  360
FTNVYADSFV IRGDEVRQIA PGQTGKIADY NYKLPDDFTG CVIAWNSNNL DSKVGGNYNY  420
LYRLFRKSNL KPFERDISTE IYQAGSTPCN GVEGFNCYFP LQSYGFQPTN GVGYQPYRVV  480
VLSFELLHAP ATVCGPKKST NLVKNKCVNF                                   510

SEQ ID NO: 7               moltype = DNA  length = 1533
FEATURE                    Location/Qualifiers
misc_feature               1..1533
                           note = Description of Artificial Sequence: Synthetic
                           polynucleotide
source                     1..1533
                           mol_type = other DNA
                           organism = synthetic construct
SEQUENCE: 7
atggatgcaa tgaagagagg gctctgctgt gtgctgctgc tgtgtggagc agtcttcgtt   60
tcggctagcg aggtgcagct cgttgagagt ggtgggggtc tggtccaacc cggtgggagt  120
ctccgcttgt catgtgcagc ttctggcttc acatttaaca cctatgccat gaactgggtc  180
cggcaggccc ccggcaaggg acttgaatgg gttgcacgga tccgctcaaa atacaacaac  240
```

```
tacgcgactt actacgctgc ctcagtcaag ggtcgcttca ccattagtcg cgacgactct    300
aagaatagtc tttatttgca gatgaatagt ctcaagaccg aggacactgc ggtatattat    360
tgcgcacggc acggaaattt tggcaattca tatgttagtt ggttcgctta ctggggcaa     420
ggcacgctcg ttacggtctc aagtggtggt ggcggttcag ggggagggg  ctctggaggg    480
ggcggttctc aaaccgttgt cacccaggaa ccaagcctga ccgtaagccc tggtgggacc    540
gtgactctca cgtgtagaag ttctacagga gctgttacta cctcaaacta cgctaactgg    600
gtacaacaaa aacccggtca agcaccaagg ggactgatag gcggaacaaa caaaagggcg    660
ccgggtactc cggcacgatt ttccggatct cttcttggag gaaaggcagc gttgactttg    720
tctggagttc agcccgagga tgaggcagag tattattgcg cactctggta tagtaacctc    780
tgggtcttcg gcggaggaac taagcttacg gtccttgggg gtgggcggca tggcggtggc    840
gggtctggag gtgggggttc ccgagtgcag ccgacggagt caatcgtgag attccctaac    900
ataactaatt tgtgtccatt tggcgaagtg ttcaatgcaa ccagattcgc ctccgtctat    960
gcgtggaatc gaaaaagaat ttcaaactgc gtagcggatt attctgtctt gtacaatagt   1020
gcctcctta  gtacgttcaa gtgttatggg gtgtcaccaa cgaagttgaa tgatctttgt   1080
ttcacgaatg tttacgctga ttcatttgta atacgcggag acgaagttag acaaatcgca   1140
ccagggcaga caggcaagat cgcggattat aattataagc tgccagacga cttcactggg   1200
tgcgttatcg catggaactc caacaacttg gatagtaaag tgggcgggaa ttacaactac   1260
ctgtatagac ttttccgaaa gtccaatttg aagccattcg aaagggacat ttctactgaa   1320
atatatcaag cgggatcaac accttgcaac ggagtggaag ggttcaactg ctactttccg   1380
ctgcaatctt atgggtttca accgactaat ggagtcgggt atcagcctta cagagttgtt   1440
gttctttcct ttgagctgtt gcatgccccg gcaaccgtat gtgggcccaa gaaatctaca   1500
aacctcgtta agaataaatg cgtgaatttc tag                                1533

SEQ ID NO: 8             moltype = DNA   length = 2996
FEATURE                  Location/Qualifiers
misc_feature             1..2996
                         note = Description of Artificial Sequence: Synthetic
                         polynucleotide
source                   1..2996
                         mol_type = other DNA
                         organism = synthetic construct
SEQUENCE: 8
cgtgaggctc cggtgcccgt cagtgggcag agcgcacatc gcccacagtc cccgagaagt     60
tggggggagg ggtcggcaat tgaaccggtg cctagagaag gtggcgcggg gtaaactggg    120
aaagtgatgt cgtgtactgc ctccgcctt  tccccgaggg tggggagaa ccgtatataa     180
gtgcagtagt cgccgtgaac gttctttttc gcaacgggtt tgccgccaga acacaggtaa    240
gtgccgtgtg tggttcccgc gggcctggcc tctttacggg ttatgccct  tgcgtgcctt    300
gaattacttc cacctggctg cagtacgtga ttcttgatcc cgagcttcgg gttggaagtg    360
ggtgggagag ttcgaggcct tgcgcttaag gagccccttc gcctcgtgct tgagttgagg    420
cctggcctgg gcgctgggc  cgccgcgtgc gaatctggtg gcaccttcgc gcctgtctcg    480
ctgctttcga taagtctcta gccatttaaa attttttgatg acctgctgcg acgcttttt    540
tctggcaaga tagtcttgta aatgcgggcc aagatctgca cactggtatt tcggtttttg    600
gggccgcggg cggcgacggg gcccgtgcgt cccagccgac atgttcggcg aggcggggcc    660
tgcgagcgcg gccaccgaga tcggacgggg ggtagtctca agctggccgg cctgctctgg    720
tgcctggcct cgcgccgccg tgtatcgccc cgccctgggc ggcaaggctg gcccggtcgg    780
caccagttgc gtgagcggaa agatggccgc ttccccggccc tgctgcaggg agctcaaaat    840
ggaggacggg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttgggggag  gggttttatg   1020
cgatggagtt tccccacact gagtgggtgg agactgaagt taggccagct tggcacttga   1080
tgtaattctc cttggaattt gccctttttg agtttggatc ttggttcatt ctcaagcctg   1140
agacagtggt tcaaagtttt tttcttccat ttcaggtgtc gtgaggaatt agctggcgcg   1200
ccttcccgcc accatggatg caatgaagag agggctctgc tgtgtgctgc tgctgtgtgg   1260
agcagtcttc gtttcggcta gcgaggtgca gctcgttgag agtggtgggg gtctggtcca   1320
acccggtggg agtctccgct tgtcatgtgc agcttctggc ttcacatttta acacctatgc   1380
catgaactgg gtccggcagg ccccccggcaa gggacttgaa tgggttgcac ggatccgctc   1440
aaaatacaac aactacgcga cttactacgc tgcctcagtc aagggtcgct tcaccattag   1500
tcgcgacgac tctaagaata gtctttattt gcagatgaat agtctcaaga ccgaggacac   1560
tgcggtatat tattgcgcac ggcacgaaaa ttttggcaat tcatatgtta gttggttcgc   1620
ttactgggg  caaggcacgc tcgttacggt ctcaagtggt ggtggcggtt caggggggag   1680
gggtctggga ggggcggtt  ctcaaaccgt tgtcacccag gaaccaagcc tgaccgtaag   1740
ccctggtggg accgtgactc tcacgtgtag aagttctaca ggagctgtta ctacctcaaa   1800
ctacgctaac tgggtacaac aaaaacccgg tcaagcacca aggggactga taggcggaac   1860
aaacaaaagg gcgccggtta ctccggcacg attttccttg aggaaaggc                1920
agcgttgact ttgtctggag ttcagcccga ggatgaggca gagtattatt gcgcactctg   1980
gtatagtaac ctctgggtct tcggcggagg aactaagctt acggtccttg ggggtggcgg   2040
cagtggcggt ggcgggtctg gaggtggggg ttcccgagtg cagccgacgg agtcaatcgt   2100
gagattccct aacataacta atttgtgtcc atttggcgaa gtgttcaatg caaccagatt   2160
cgcctccgtc tatgcgtgga atcgaaaaag aatttcaaac tgcgtagcgg attattctgt   2220
cttgtacaat agtgcctcct ttagtacgtt caagtgttat ggggtgtcac caacgaagtt   2280
gaatgatctt tgtttcacga atgtttacgc tgattcattt gtaatacgcg gagacgaagt   2340
tagacaaatc gcaccagggc agacaggcaa gatcgcggat tataattata agctgccaga   2400
cgacttcact gggtgcgtta tcgcatggaa ctccaacaac ttggatagta aagtgggcgg   2460
gaattaacc  taccgtgtata gacttttccg aaagtccaat ttgaagccat tcgaaaggga   2520
catttctact gaaatatatc aagcgggatc aacaccttgc aacggagtgg aagggttcaa   2580
ctgctacttt ccgctgcaat cttatgggtt tcaaccgact aatggagtcg ggtatcagcc   2640
ttacagagtt gttgttcttt cctttgagct gttgcatgcc ccggcaaccg tatgtgggcc   2700
caagaaatct acaaacctcg ttaagaataa atgcgtgaat ttctagtagc ctgcaggacg   2760
ccacagctct gatcataatc agccatacca catttgtaga ggttttactt gctttaaaaa   2820
```

```
acctcccaca cctcccctg aacctgaaac ataaaatgaa tgcaattgtt gttgttaact    2880
tgtttattgc agcttataat ggttacaaat aaagcaatag catcacaaat ttcacaaata   2940
aagcattttt ttcactgcat tctagttgtg gtttgtccaa actcatcaat gtatct       2996

SEQ ID NO: 9              moltype = AA   length = 752
FEATURE                   Location/Qualifiers
REGION                    1..752
                          note = Description of Artificial Sequence: Synthetic
                          polypeptide
source                    1..752
                          mol_type = protein
                          organism = synthetic construct
SEQUENCE: 9
MDAMKRGLCC VLLLCGAVFV SASEVQLVES GGGLVQPGGS LRLSCAASGF TFNTYAMNWV    60
RQAPGKGLEW VARIRSKYNN YATYYAASVK GRFTISRDDS KNSLYLQMNS LKTEDTAVYY   120
CARHGNFGNS YVSWFAYWGQ GTLVTVSSGG GGSGGGGSGG GGSQTVVTQE PSLTVSPGGT   180
VTLTCRSSTG AVTTSNYANW VQQKPGQAPR GLIGGTNKRA PGTPARFSGS LLGGKAALTL   240
SGVQPEDEAE YYCALWYSNL WVFGGGTKLT VLGGGGSGGG GSGGGGSRVQ PTESIVRFPN   300
ITNLCPFGEV FNATRFASVY AWNRKRISNC VADYSVLYNS ASFSTFKCYG VSPTKLNDLC   360
FTNVYADSFV IRGDEVRQIA PGQTGKIADY NYKLPDDFTG CVIAWNSNNL DSKVGGNYNY   420
LYRLFRKSNL KPFERDISTE IYQAGSTPCN GVEGFNCYFP LQSYGFQPTN GVGYQPYRVV   480
VLSFELLHAP ATVCGPKKST NLVKNKCVNF GGGGSGGGGS GGGGSDKTHT CPPCPAPELL   540
GGPSVFLFPP KPKDTLMISR TPEVTCVVVD VSHEDPEVKF NWYVDGVEVH NAKTKPREEQ   600
YNSTYRVVSV LTVLHQDWLN GKEYKCKVSN KALPAPIEKT ISKAKGQPRE PQVYTLPPSR   660
DELTKNQVSL TCLVKGFYPS DIAVEWESNG QPENNYKTTP PVLDSDGSFF LYSKLTVDKS   720
RWQQGNVFSC SVMHEALHNH YTQKSLSLSP GK                                 752

SEQ ID NO: 10             moltype = DNA   length = 2259
FEATURE                   Location/Qualifiers
misc_feature              1..2259
                          note = Description of Artificial Sequence: Synthetic
                          polynucleotide
source                    1..2259
                          mol_type = other DNA
                          organism = synthetic construct
SEQUENCE: 10
atggatgcca tgaagagagg attgtgttgc gtacttctcc tttgcggggc agtctttgtg     60
tcagctagtg aagttcaact cgtcgaatca ggtggaggcc ttgtgcaacc gggaggttcc    120
ttgcgcttt catgtgcagc gtcaggcttt accttcaata catatgccat gaactgggtc    180
cgccaggccc cggcaaggg tctcgaatgg gtagcgcgca tccgcagcaa gtacaataat    240
tatgcgacct attatgcagc ctcagtaaaa gggaggttca ccatatctcg ggacgactct    300
aaaaatagcc tctatctcca gatgaatagt cttaaaactg aggatacggc ggtgtactat    360
tgcgcccggc atggcaactt tgggaatagc tatgtctcat ggtttgccta ttggggcgag    420
ggaacgctgg tgaccgtttc aagcggagga ggcggatctc gcgcggagg ttcaggtggc    480
ggcggttcac aaacagtcgt gacccaggaa cccagcctta ccgtctctcc cggagggaca    540
gttacactga cgtgcagatc aagtaccggc gccgtcacta cttctaacta cgctaattgg    600
gttcaacaaa agccgggtca agcaccacga ggtttgatag ggggacaaa taaaagggct    660
ccagcacccc ccgctcgctt ctccggggagt ctcttggggg gcaaagccgc gctgacgttg   720
tctggagtcc agcctgagga tgaagccgag tattactgcg ctctttgta ctctaacctg    780
tgggtctttg gggaggcac gaaacttaca gtcttgggtg gcggtggttc aggcggtggt    840
ggaagcggag gcggcggttc tagggtgcag ccgacagaa gtatcgtccg gtttccgaac    900
attaccaatt tgtgtccctt cggcgaagtc tttaatgcta caaggtttgc cagcgtctac    960
gcatggaatc gcaaaagaat aagcaattgc gtagccgatt attcagtatt gtacaattcc   1020
gcttctttttt caacattcaa atgttatggg gtgtccccta cgaagttgaa tgacctgtgt   1080
ttcacgaatg tctacgcaga ttcttttgtc atacgcgggg acgaagtgca acaaattgca   1140
cccggccaaa ccggcaaaat agcggactat aactataagc tccccgacga tttcaccggg   1200
tgcgtcatag cctggaacag caacaacctc gattcaaaag tcggaggcaa ctacaactat   1260
ctttacaggt tgttccggaa gtcaaatctg aagccctttg aacgggatat ctcaactgaa   1320
atttatcaag ccggatctac tccgtgcaat ggagtcgaag gatttaattg ctactttccc   1380
cttcagtcct atggtttca acccacgaat ggcgtcggtt accagcccta cagagtcgtt   1440
gttttgtcat tcgaactgct gcacgcgcca gcaacggtat gcggcccaa gaaaagcacg   1500
aatttggtga aaaataatg cgttaacttt ggaggtgggg gatccggcgg aggaggtagt   1560
ggaggggag gcagtgacaa acacacacc tgtccgccct gccccgcccc tgagctcctg    1620
gggggaccta gcgtctttt gtttccacca aagcccaaga cacacttat gatatctcgg    1680
acaccggaag taacttgtgt agttgtagac gtatcacatg aggaccccga ggtcaaattc    1740
aattggtacg tcgatggtgt cgaagtgcac aatgcaaaaa cgaaaccgcg agaggagcaa    1800
tataacagta cgtatcgcgt cgtcagcgtg ttgacggtac tccatcaaga ttggctcaat    1860
ggaaaggagt ataagtgcaa ggtatccaac aaggcccttc cgcacctat agaaaagacg    1920
atttcaaaag ccaaaggcca accccgagag cccccaagtat atacactccc accctctcgg    1980
gatgagctga cgaaaaacca ggttagtctc acttgcctcg tcaagggatt ttaccccctcc    2040
gatatagcgt ggagtgggga gtccaatggc caaccggaga caactataa aacgactcct    2100
cctgtactcg attcagacgg atctttcttt ttgtacagta agcttactgt tgacaaatcc    2160
aggtggcaac aagggaatgt attcagctgt agtgtaatgc acgaggcatt gcacaaccac    2220
tacactcaga aatctctcag tctgtcccca ggaaagtag                           2259

SEQ ID NO: 11             moltype = AA   length = 500
FEATURE                   Location/Qualifiers
REGION                    1..500
                          note = Description of Artificial Sequence: Synthetic
```

```
                        polypeptide
source                  1..500
                        mol_type = protein
                        organism = synthetic construct
SEQUENCE: 11
MDAMKRGLCC VLLLCGAVFV SASEVQLVES GGGLVQPGGS LRLSCAASGF TFNTYAMNWV    60
RQAPGKGLEW VARIRSKYNN YATYYAASVK GRFTISRDDS KNSLYLQMNS LKTEDTAVYY   120
CARHGNFGNS YVSWFAYWGQ GTLVTVSSGG GGSQTVVTQE PSLTVSPGGT VTLTCRSSTG   180
AVTTSNYANW VQQKPGQAPR GLIGGTNKRA PGTPARFSGS LLGGKAALTL SGVQPEDEAE   240
YYCALWYSNL WVFGGGTKLT VLGGGSGGG GSGGGGSRVQ PTESIVRFPN ITNLCPFGEV    300
FNATRFASVY AWNRKRISNC VADYSVLYNS ASFSTFKCYG VSPTKLNDLC FTNVYADSFV   360
IRGDEVRQIA PGQTGKIADY NYKLPDDFTG CVIAWNSNNL DSKVGGNYNY LYRLFRKSNL   420
KPFERDISTE IYQAGSTPCN GVEGFNCYFP LQSYGFQPTN GVGYQPYRVV VLSFELLHAP   480
ATVCGPKKST NLVKNKCVNF                                               500

SEQ ID NO: 12           moltype = DNA    length = 1503
FEATURE                 Location/Qualifiers
misc_feature            1..1503
                        note = Description of Artificial Sequence: Synthetic
                        polynucleotide
source                  1..1503
                        mol_type = other DNA
                        organism = synthetic construct
SEQUENCE: 12
atggatgcaa tgaagagagg gctctgctgt gtgctgctgc tgtgtggagc agtcttcgtt    60
tcggctagcg aagtccaact tgtcgaatca ggtggggact ggtacaaacc agggggctcc   120
ctccgcctta gctgcgcagc gtccgggttc acgtttaaca cttacgcaat gaactgggtc   180
cggcaagcac ccgtaaagg tttggagtgg gtggcacgca ttagatccaa atacaacaat    240
tatgctacgt actatgcggc tagtgtgaag ggaaggtta ctatatcaag agatgacagt    300
aaaaacagtc tctacctcca gatgaactca ctgaaaaccg aggataccgc agtctattac   360
tgcgcgcgcc acggtaattt tggcaattct tacgtgagct ggtttgctta ctggggccaa   420
gggactctcg tcaccgtcag ctctggtggt ggtggtagcc agacggtagt tactcaggag   480
ccaagcctga cggtcagtcc gggcggaaca gttaccctga catgcaggtc ttccaccggg   540
gcggtcacca cttctaacta tgcgaactgg gtacaacaga aaccaggaca agcacccga   600
gggcttatcg ggggcacgaa taaacgagca cctggaactc cggcaaggt ctctggaagc    660
ctgcttgggg gcaaggcggc gctcactctt tcaggtgtgc aaccggaaga cgaagcagaa   720
tattactgtg cattgtggta ctccaacctc tgggtgttcg gtggcgggac caaactcaca   780
gtgctggcg gtggtgggag cggggtggg ggttctggtg gtgaggtag ccgagtgcag      840
ccgacggagt caatcgtgag attccctaac ataactaatt tgtgtccatt tggcgaagtg   900
ttcaatgcaa ccagattcgc ctccgtctat gcgtggaatc gaaaaagaat ttcaaactgc   960
gtagcggatt attctgtctt gtacaatagt gcctcctta gtacgttcaa gtgttatggg   1020
gtgtcaccaa cgaagttgaa tgatcttgt ttcacgaatg tttacgctga ttcatttgta    1080
atacgggag acgaagttag acaaatcgca ccagggcaga caggcaagat gcgcgattat    1140
aattataagc tgccagacga cttcactggg tgcgttatcg catggaactc caacaacttg   1200
gatagtaaag tgggcgggaa ttacaactac ctgtatagac ttttccgaaa gtccaatttg   1260
aagccattcg aaagggacat ttctactgaa atatatcaag cgggatcaac accttgcaac   1320
ggagtggaag ggttcaactg ctactttccg ctgcaattct atgggttca accgactaat    1380
ggagtcgggt atcagcctta cagagttgtt gttctttcct ttgagcttgt tcatgccccg   1440
gcaaccgtat gtgggcccaa gaaatctaca aacctcgtta agaataaatg cgtgaatttc   1500
tag                                                                 1503

SEQ ID NO: 13           moltype = AA    length = 500
FEATURE                 Location/Qualifiers
REGION                  1..500
                        note = Description of Artificial Sequence: Synthetic
                        polypeptide
source                  1..500
                        mol_type = protein
                        organism = synthetic construct
SEQUENCE: 13
MDAMKRGLCC VLLLCGAVFV SASEVQLVES GGGLVQPGGS LRLSCAASGF TFNTYAMNWV    60
RQAPGKGLEW VARIRSKYNN YATYYAASVK GRFTISRDDS KNSLYLQMNS LTTCDTAVYY   120
CARHGNFGNS YVSWFAYWGQ GTLVTVSSGG GGSQTVVTQE PSLTVSPGGT VTLTCRSSTG   180
AVTTSNYANW VQQKPGQAPR GLIGGTNKRA PGTPARFSGS LLGGKAALTL SGVQPEDEAE   240
YYCALWYSNL WVFGGGTKLT VLGGGSGGG GSGGGGSRVQ PTESIVRFPN ITNLCPFGEV    300
FNATRFASVY AWNRKRISNC VADYSVLYNS ASFSTFKCYG VSPTKLNDLC FTNVYADSFV   360
IRGDEVRQIA PGQTGKIADY NYKLPDDFTG CVIAWNSNNL DSKVGGNYNY LYRLFRKSNL   420
KPFERDISTE IYQAGSTPCN GVEGFNCYFP LQSYGFQPTN GVGYQPYRVV VLSFELLHAP   480
ATVCGPKKST NLVKNKCVNF                                               500

SEQ ID NO: 14           moltype = DNA    length = 1503
FEATURE                 Location/Qualifiers
misc_feature            1..1503
                        note = Description of Artificial Sequence: Synthetic
                        polynucleotide
source                  1..1503
                        mol_type = other DNA
                        organism = synthetic construct
SEQUENCE: 14
```

```
atggatgcaa tgaagagagg gctctgctgt gtgctgctgc tgtgtggagc agtcttcgtt    60
tcggctagcg aggttcaatt ggtgaatctc ggagggggc ttgtccaacc cggagggtcc    120
ttgagactga gttgtgcagc gagcggtttc acatttaaca cttacgccat gaactgggtt    180
aggcaagccc ccgggaaggg actggagtgg gttgccagaa tcagatcaaa atacaataat    240
tatgcaacat actatgcagc tagtgtcaag ggaagattca ccataagccg agacgactct    300
aagaatagcc tgtatctgca aatgaatagt ctcacgactt gcgatactgc cgtatactac    360
tgtgcacgcc atgaaatttt cggcaacagc tatgtttcct ggtttgccta ttggggacaa    420
ggcacgctcg tcactgtttc ttcaggagga ggtggcagtc aaacggttgt gacccaagaa    480
ccctcgctca ctgtgtcacc aggaggaact gtgacgctca catgccgatc ctccaccggt    540
gccgtcacta cgagcaatta tgctaactgg gtacagcaaa agccagggca agcacctcga    600
ggcctgatcg gtggcacgaa taacgagcg cctggtacgc cagcccgctt ttctggatct    660
cttctgggcg gaaaagcagc cctgactctc tccggggtac agccgaggga cgaagcagag    720
tactactgcg ctctttggta tagcaacctt tgggtgttcg gtggtggtac gaaactcact    780
gttctcggtg gaggggtag cggggggtggc gggagtggtg gcggaggttc acgagtgcag    840
ccgacggagt caatcgtgag attccctaac ataactaatt tgtgtccatt ggcgaagtg    900
ttcaatgcaa ccagattcgc ctccgtctat gcgtggaatc gaaaaagaat ttcaaactgc    960
gtagcggatt atctctgtct tgtacaatagt gcctcctttta gtacgttcaa gtgttatggg   1020
gtgtcaccaa cgaagttgaa tgatctttgt ttcacgaagt ttacgctga ttcatttgta   1080
atacgcggag acgaagttag acaaatcgca ccagggcaga caggcaagat cgcggattat   1140
aattataagc tgccagacga cttcactggg tgcgttatcg catggaactc caacaacttg   1200
gatagtaaag tgggcgggaa ttacaactac ctgtatagac ttttccgaaa gtccaatttg   1260
aagccattcg aaagggacat ttctactgaa atatatcaag cggatcaac accttgcaac   1320
ggagtggaag ggttcaactg ctactttccg ctgcaatctt atgggtttca accgactaat   1380
ggagtcgggt atcagcctta cagagttgtt gttctttcct ttgagctgtt gcatgccccg   1440
gcaaccgtat gtgggcccaa gaaatctaca aacctcgtta agaataaatg cgtgaatttc   1500
tag                                                                  1503

SEQ ID NO: 15              moltype = AA  length = 506
FEATURE                    Location/Qualifiers
REGION                     1..506
                           note = Description of Artificial Sequence: Synthetic
                           polypeptide
source                     1..506
                           mol_type = protein
                           organism = synthetic construct
SEQUENCE: 15
MDAMKRGLCC VLLLCGAVFV SASQVQLVQS GAEVQRPGAS VKVSCKASGY IFTEYYMYWV    60
RQAPGQGLEL VGRIDPEDGS IDYVEKFKKK VTLTADTSSS TAYMELSSLT SDDTAVYYCA   120
RGKFNYRFAY WGQGTLVTVS SGGGGSGGGG SGGGGSDVVM TQSPPSLLVT LGQPASISCR   180
SSQSLLHSSG NTYLNWLLQR PGQSPQPLIY LVSKLESGVP DRFSGSGSGT DFTLKISGVE   240
AEDVGVYYCM QFTHYPYTFG QGTKLEIKGG GGSGGGGSGG GGSRVQPTES IVRFPNITNL   300
CPFGEVFNAT RFASVYAWNR KRISNCVADY SVLYNSASFS TFKCYGVSPT KLNDLCFTNV   360
YADSFVIRGD EVRQIAPGQT GKIADYNYKL PDDFTGCVIA WNSNNLDSKV GGNYNYLYRL   420
FRKSNLKPFE RDISTEIYQA GSTPCNGVEG FNCYFPLQSY GFQPTNGVGY QPYRVVVLSF   480
ELLHAPATVC GPKKSTNLVK NKCVNF                                        506

SEQ ID NO: 16              moltype = DNA  length = 1521
FEATURE                    Location/Qualifiers
misc_feature               1..1521
                           note = Description of Artificial Sequence: Synthetic
                           polynucleotide
source                     1..1521
                           mol_type = other DNA
                           organism = synthetic construct
SEQUENCE: 16
atggatgcaa tgaagagagg gctctgctgt gtgctgctgc tgtgtggagc agtcttcgtt    60
tcggctagcc aggtccaact tgttcaatca ggagctgagg tacagcgacc gggggcatct   120
gttaaggtca gttgcaaagc ttcaggctat atattcactg aatactatat gtattgggtc   180
cggcaagcac ctgggcaggg cctggaactc gtcggtagaa ttgaccctga ggatggctca   240
attgactatg tcgaaaaatt taaaaaaaaa gtgacgctca cagcggacac tagcagtctca   300
actgcttaca tggagctttc cagcttgacc tctgatgata ctgcggtcta ctactgtgcg   360
cgagggaagt ttaactatag gtttgcatac tggggccaag gaacgctggt aaccgtcagt   420
tcaggaggtg gaggaagcgg cggtggaggg agcggaggcg gaggtagcga tgtggtgatg   480
actcaatctc caccttccct gctcgtaacg ctcggccaac tcgcttccat aagctgctca   540
tcctcacaga gcctgctcca ttcttctggt aacacttatc ttaactggct tctgcaaaga   600
ccgggtcaat caccccaacc tcttatctat ctggtatcta aactgaatc cggggttccc   660
gatcgattca gcgggtcagg cagtggaacg gactttacct tgaaaatttc aggggtagag   720
gcggaagacg tagggggtcta ctactgtatg caattcactc attacccgta tacgtttgga   780
caagggacta agctggaaat taaggcgggg ggaggttctg ggggagggtgg gagcgggggaa   840
ggggggttccc gagtgcagcc gacggagtca atcgtgagat ccctaacat aactaatttg    900
tgtccatttg gcgaagtgtt caatgcaacc agattcgcct ccgtctatgc gtggaatcga    960
aaaagaattt caaactgcgt agcggattat ctctgtcttgt acaatagtgc ctcctttagt  1020
acgttcaagt gttatggggt gtcaccaacg aagttgaatg atctttgttt cacgaatgtt  1080
tacgctgatt catttgtaat acgcggagac gaagttagac aaatcgcacc agggcagaca  1140
ggcaagatcg cggattataa ttataagctg ccagacgact tcactgggtg cgttatcgca  1200
tggaactcca acaacttgga tagtaaagtg ggcgggaatt acaactacct gtatagactt  1260
ttccgaaagt ccaatttgaa gccattcgaa agggacattt ctactgaaat atatcaagcg  1320
ggatcaacac cttgcaacgg agtggaaggg ttcaactgct actttccgct gcaatcttat  1380
gggtttcaac cgactaatgg agtcgggtat cagccttaca gagttgttgt tctttccttt  1440
```

```
gagctgttgc atgccccggc aaccgtatgt gggcccaaga aatctacaaa cctcgttaag   1500
aataaatgcg tgaatttcta g                                             1521
```

| SEQ ID NO: 17 | moltype = AA   length = 496 |
|---|---|
| FEATURE | Location/Qualifiers |
| REGION | 1..496 |
| | note = Description of Artificial Sequence: Synthetic polypeptide |
| source | 1..496 |
| | mol_type = protein |
| | organism = synthetic construct |

SEQUENCE: 17
```
MDAMKRGLCC VLLLCGAVFV SASQVQLVQS GAEVQRPGAS VKVSCKASGY IFTEYYMYWV    60
RQAPGQGLEL VGRIDPEDGS IDYVEKFKKK VTLTADTSSS TAYMELSSLT SDDTAVYYCA   120
RGKFNYRFAY WGQGTLVTVS SGGGGSDVVM TQSPPSLLVT LGQPASISCR SSQSLLHSSG   180
NTYLNWLLQR PGQSPQPLIY LVSKLESGVP DRFSGSGSGT DFTLKISGVE AEDVGVYYCM   240
QFTHYPYTFG QGTKLEIKGG GGSGGGGSGG GGSRVQPTES IVRFPNITNL CPFGEVFNAT   300
RFASVYAWNR KRISNCVADY SVLYNSASFS TFKCYGVSPT KLNDLCFTNV YADSFVIRGD   360
EVRQIAPGQT GKIADYNYKL PDDFTGCVIA WNSNNLDSKV GGNYNYLYRL FRKSNLKPFE   420
RDISTEIYQA GSTPCNGVEG FNCYFPLQSY GFQPTNGVGY QPYRVVVLSF ELLHAPATVC   480
GPKKSTNLVK NKCVNF                                                  496
```

| SEQ ID NO: 18 | moltype = DNA   length = 1491 |
|---|---|
| FEATURE | Location/Qualifiers |
| misc_feature | 1..1491 |
| | note = Description of Artificial Sequence: Synthetic polynucleotide |
| source | 1..1491 |
| | mol_type = other DNA |
| | organism = synthetic construct |

SEQUENCE: 18
```
atggatgcaa tgaagagagg gctctgctgt gtgctgctgc tgtgtggagc agtcttcgtt    60
tcggctagcc aggtgcaact tgttcagagt ggtgcgaggt tcagcgaccc ggcgcgagc   120
gtaaaggtga gctgcaaggc tagcggttat atttttactg agtattatat gtattgggtt   180
cggcaagctc ctggccaagg gctcgaactc gtaggcagaa ttgacccaga ggacgggagt   240
atcgattatg tagagaagtt caaaaagaag gtaacactta cagcagatac gtcaagttcc   300
actgcgtaca tggaactctc aagtctgacc agtgatgata cagcagttta ctattgtgcg   360
cggggtaagt tcaattatag gtttgcgtac tggggacaag gtacactggt taccgtcagc   420
tctggagggg gtgggagcga cgtcgttatg actcagagtc cgccatcact cctggtgacg   480
ctgggtcaac cagcttctat cagttgccgg agctcccagt cactcctgca ttcatcaggg   540
aacacgtacc tgaattggct ccttcagcgg ccaggacaat ctccccaacc tctgatttat   600
cttgtttcca agcttgagag cggcgtccca gatcgatttt ctgggtccgg tagtggtacg   660
gacttcactt tgaaaatatc cggggttgaa gcagaagacg ttggggttta ctattgcatg   720
cagttcacac attatccgta tacatttggg caagggacca aacttgaaat aaaaggggc   780
ggcggatctg ggggtggtgg tagtggtggt ggtggctctc gagtgcagcc gacggagtca   840
atcgtgagat tccctaacat aactaatttg tgtccatttg gcgaagtgtt caatgcaacc   900
agattcgcct ccgtctatgc gtggaatcga aaaagaattc aaactcgct aggcgattat   960
tctgtcttgt acaatagtgc ctcctttagt acgttcaagt gttatggggt gtcaccaacg  1020
aagttgaatg atctttgttt cacgaatgtt tacgctgatt catttgtaat acgcggagac  1080
gaagttagac aaatcgcacc agggcagaca ggcaagatcg cggattataa ttataagctg  1140
ccagacgact tcactgggtg cgttatcgca tggaactcaa acaacttgga tagtaaagtg  1200
ggcgggaatt acaactacct gtatagactt ttccgaaagt ccaatttgaa gccattcgaa  1260
agggacattt ctactgaaat atatcaagcg ggatcaacac cttgcaacgg agtgaagggg  1320
ttcaactgct actttccgct gcaatcttat gggtttcaac cgactaatgg agtcgggtat  1380
cagccttaca gagttgttgt tctttccttt gagctgttgc atgccccggc aaccgtatgt  1440
gggcccaaga aatctacaaa cctcgttaag aataaatgcg tgaatttcta g           1491
```

| SEQ ID NO: 19 | moltype = AA   length = 496 |
|---|---|
| FEATURE | Location/Qualifiers |
| REGION | 1..496 |
| | note = Description of Artificial Sequence: Synthetic polypeptide |
| source | 1..496 |
| | mol_type = protein |
| | organism = synthetic construct |

SEQUENCE: 19
```
MDAMKRGLCC VLLLCGAVFV SASQVQLVQS GAEVQRPGAS VKVSCKASGY IFTEYYMYWV    60
RQAPGQGLEL VGRIDPEDGS IDYVEKFKKK VTLTADTSSS TAYMELSSLT SCDTAVYYCA   120
RGKFNYRFAY WGQGTLVTVS SGGGGSDVVM TQSPPSLLVT LGQPASISCR SSQSLLHSSG   180
NTYLNWLLQR PGQSPQPLIY LVSKLESGVP DRFSGSGSGT DFTLKISGVE AEDVGVYYCM   240
QFTHYPYTFG QGTKLEIKGG GGSGGGGSGG GGSRVQPTES IVRFPNITNL CPFGEVFNAT   300
RFASVYAWNR KRISNCVADY SVLYNSASFS TFKCYGVSPT KLNDLCFTNV YADSFVIRGD   360
EVRQIAPGQT GKIADYNYKL PDDFTGCVIA WNSNNLDSKV GGNYNYLYRL FRKSNLKPFE   420
RDISTEIYQA GSTPCNGVEG FNCYFPLQSY GFQPTNGVGY QPYRVVVLSF ELLHAPATVC   480
GPKKSTNLVK NKCVNF                                                  496
```

| SEQ ID NO: 20 | moltype = DNA   length = 1491 |
|---|---|
| FEATURE | Location/Qualifiers |
| misc_feature | 1..1491 |

```
                        note = Description of Artificial Sequence: Synthetic
                               polynucleotide
source                  1..1491
                        mol_type = other DNA
                        organism = synthetic construct
SEQUENCE: 20
atggatgcaa tgaagagagg gctctgctgt gtgctgctgc tgtgtggagc agtcttcgtt   60
tcggctagcc aggtccagct cgtacaaagc ggagctgaag tccagaggcc gggagcgagc  120
gtaaaggtct cttgtaaagc ctctggatac attttacgg agtactacat gtattgggtt   180
aggcaggcac ctggtcaagg tttggaattg gtcgggagaa tagaccctga agatgggtca  240
atagattatg tcgaaaaatt caagaagaaa gtaaccctca cagcagatac aagctcaagc  300
actgcttata tggaactttc tagcctcacc tcttgcgaca ccgcagttta ttactgtgcc  360
agagggaaat ttaattacag gtttgcctac tggggacaaa gaacgttggt aacggtatca  420
tccggcggtg gtggatcaga cgtggttatg acacagtccc caccgagctt gcttgttact  480
ctcgggcagc ctgccagcat ctcatgcaga tcatctcaga gccttcttca ttcatctggc  540
aacacctacc ttaattggct gctccaacga ccgggtcagt cccccaacc cttgatatac  600
ttggttagta aactcgaaag tggagttccg acagattct ctggatctgg aagcggaact  660
gattttaccc tcaagatatc cggcgtagag gcggaagatg tcggggttta ctattgtatg  720
caatttactc attacccgta cacttttggt cagggcacaa agctcgaaat taaaggagga  780
ggaggttctg gaggcggggg cagcggtggt ggaggttccc gagtgcagcc gacggagtca  840
atcgtgagat tccctaacat aactaatttg tgtccatttg gcgaagtgtt caatgcaacc  900
agattcgcct ccgtctatgc gtggaatcga aaaagaattt caaactgcgt agcggattat  960
tctgtcttgt acaatagtgc ctcctttagt acgttcaagt gttatggggt gtcaccaacg 1020
aagttgaatg atctttgttt cacgaatgtt tacgctgatt catttgtaat acgcggagac 1080
gaagttagac aaatcgcacc agggcagaca ggcaagatcg cggattataa ttataagctg 1140
ccagacgact tcactgggtg cgttatcgca tggaactcca acaacttgga tagtaaagtg 1200
ggcgggaatt acaactacct gtatagactt ttccgaaagt ccaatttgaa gccattcgaa 1260
agggacattt ctactgaaat atatcaagcg ggatcaacac cttgcaacgg agtggaaggg 1320
ttcaactgct actttccgct gcaatcttat gggtttcaac cgactaatgg agtcgggtat 1380
cagccttaca gagttgttgt tctttccttt gagctgttgc atgccccggc aaccgtatgt 1440
gggcccaaga aatctacaaa cctcgttaag aataaatgcg tgaatttcta g           1491

SEQ ID NO: 21           moltype = AA  length = 356
FEATURE                 Location/Qualifiers
REGION                  1..356
                        note = Description of Artificial Sequence: Synthetic
                               polypeptide
source                  1..356
                        mol_type = protein
                        organism = synthetic construct
SEQUENCE: 21
MDAMKRGLCC VLLLCGAVFV SASFSQQIYG VVYGNVTFHV PSNVPLKEVL WKKQKDKVAE   60
LENSEFRAFS SFKNRVYLDT VSGSLTIYNL TSSDEDEYEM ESPNITDTMK FFLYVLESGG  120
GGSGGGGSGG GGSRVQPTES IVRFPNITNL CPFGEVFNAT RFASVYAWNR KRISNCVADY  180
SVLYNSASFS TFKCYGVSPT KLNDLCFTNV YADSFVIRGD EVRQIAPGQT GKIADYNYKL  240
PDDFTGCVIA WNSNNLDSKV GGNYNYLYRL FRKSNLKPFE RDISTEIYQA GSTPCNGVEG  300
FNCYFPLQSY GFQPTNGVGY QPYRVVVLSF ELLHAPATVC GPKKSTNLVK NKCVNF      356

SEQ ID NO: 22           moltype = DNA  length = 1071
FEATURE                 Location/Qualifiers
misc_feature            1..1071
                        note = Description of Artificial Sequence: Synthetic
                               polynucleotide
source                  1..1071
                        mol_type = other DNA
                        organism = synthetic construct
SEQUENCE: 22
atggatgcaa tgaagagagg gctctgctgt gtgctgctgc tgtgtggagc agtcttcgtt   60
tcggctagct tcagtcagca aatctacggt gtcgtgtatg gcaatgtgac atttcacgtg  120
ccgagtaacg tccctctcaa ggaggttttg tggaagaagc agaaggataa ggtggccgag  180
ctggagaact ctgagtttcg ggcttttctc tctttcaaaa atcgagtata cctcgataca  240
gtcagtgggt ctctgaccat atataacctt acttcctctg atgaggacga atatgagatg  300
gaatctccga acataaacaga tactatgaag ttcttcctct atgtactcga atcagggggt  360
ggtggtctg gaggggcgg ttcagggga ggcggcagc gacggagtca  420
atcgtgagat tccctaacat aactaatttg tgtccatttg gcgaagtgtt caatgcaacc  480
agattcgcct ccgtctatgc gtggaatcga aaaagaattt caaactgcgt agcggattat  540
tctgtcttgt acaatagtgc ctcctttagt acgttcaagt gttatggggt gtcaccaacg  600
aagttgaatg atctttgttt cacgaatgtt tacgctgatt catttgtaat acgcggagac  660
gaagttagac aaatcgcacc agggcagaca ggcaagatcg cggattataa ttataagctg  720
ccagacgact tcactgggtg cgttatcgca tggaactcca acaacttgga tagtaaagtg  780
ggcgggaatt acaactacct gtatagactt ttccgaaagt ccaatttgaa gccattcgaa  840
agggacattt ctactgaaat atatcaagcg ggatcaacac cttgcaacgg agtggaaggg  900
ttcaactgct actttccgct gcaatcttat gggtttcaac cgactaatgg agtcgggtat  960
cagccttaca gagttgttgt tctttccttt gagctgttgc atgccccggc aaccgtatgt 1020
gggcccaaga aatctacaaa cctcgttaag aataaatgcg tgaatttcta g          1071

SEQ ID NO: 23           moltype = AA  length = 356
FEATURE                 Location/Qualifiers
REGION                  1..356
```

```
                           note = Description of Artificial Sequence: Synthetic
                                 polypeptide
source                     1..356
                           mol_type = protein
                           organism = synthetic construct
SEQUENCE: 23
MDAMKRGLCC VLLLCGAVFV SASFSQQIYG VVYGNVTFHV PSNVPLKEVL WKKQKDKVAE    60
LENSEFRAFS SFKNRVYLDT VSGSLTIYNL TSSDEDEYEM ESPNITDTMK FFLYVLESGG   120
GGSGGGGSGG GGSRVQPTES IVRFPNITNL CPFGEVFNAT RFASVYAWNR KRISNCVADY   180
SVLYNSASFS TFKCYGVSPT KLNDLCFTNV YADSFVIRGD EVRQIAPGQT GNIADYNYKL   240
PDDFTGCVIA WNSNNLDSKV GGNYNYLYRL FRKSNLKPFE RDISTEIYQA GSTPCNGVKG   300
FNCYFPLQSY GFQPTYGVGY QPYRVVVLSF ELLHAPATVC GPKKSTNLVK NKCVNF       356

SEQ ID NO: 24              moltype = DNA  length = 1071
FEATURE                    Location/Qualifiers
misc_feature               1..1071
                           note = Description of Artificial Sequence: Synthetic
                                 polynucleotide
source                     1..1071
                           mol_type = other DNA
                           organism = synthetic construct
SEQUENCE: 24
atggatgcaa tgaagagagg gctctgctgt gtgctgctgc tgtgtggagc agtcttcgtt    60
tcggctagct tcagtcagca aatctacggt gtcgtgtatg gcaatgtgac atttcacgtg   120
ccgagtaacg tccctctcaa ggaggttttg tggaagaagc agaaggataa ggtggccgag   180
ctggagaact ctgagtttcg ggcttttctc tctttcaaaa atcgagtata cctcgataca   240
gtcagtgggt ctctgaccat atataacctt acttcctctg atgaggacga atatgagatg   300
gaatctccga acataacaga tactatgaag ttcttcctct atgtactcga atcagggggt   360
ggtgggtctg gaggggcgg ttcagggga ggcgggagtc gagtgcagcc gacggagtca   420
atcgtgagat tccctaacat aactaatttg tgtccatttg gcgaagtttt caatgcaacc   480
agattcgcct ccgtctatgc gtggaatcga aaaagaattt caaactgcgt agcggattat   540
tctgtcttgt acaatagtgc ctcctttagt acgttcaagt gttatggggt gtcaccaacg   600
aagttgaatg atctttgttt cacgaatgtt tacgctgatt catttgtaat acgcggagac   660
gaagttagac aaatcgcacc agggcagaca ggcaacatcg cggattataa ttataagctg   720
ccagacgact tcactgggtg cgttatcgca tggaactcca acaacttgga tagtaagtg   780
ggcgggaatt acaactacct gtatagactt ttccgaaagt ccaatttgaa gccattcgaa   840
agggacattt ctactgaaat atatcaagcg ggatcaacac cttgcaacgg agtgaaaggg   900
ttcaactgct actttccgct gcaatcttat gggtttcaac cgacttatgg agtcgggtat   960
cagccttaca gagttgttgt tctttccttt gagcttgttgc atgccccggc aaccgtatgt  1020
gggcccaaga aatctacaaa cctcgttaag aataaatgcg tgaatttcta g           1071

SEQ ID NO: 25              moltype = AA  length = 560
FEATURE                    Location/Qualifiers
REGION                     1..560
                           note = Description of Artificial Sequence: Synthetic
                                 polypeptide
source                     1..560
                           mol_type = protein
                           organism = synthetic construct
SEQUENCE: 25
MDAMKRGLCC VLLLCGAVFV SASEVQLVES GGGLVQPGGS LRLSCAASGF TFNTYAMNWV    60
RQAPGKGLEW VARIRSKYNN YATYYAASVK GRFTISRDDS KNSLYLQMNS LKTEDTAVYY   120
CARHGNFGNS YVSWFAYWGQ GTLVTVSSGG GGSGGGGSGG GGSQTVVQE PSLTVSPGGT   180
VTLTCRSSTG AVTTSNYANW VQQKPGQAPR GLIGGTNKRA PGTPARFSGS LLGGKAALTL   240
SGVQPEDEAE YYCALWYSNL WVFGGGTKLT VLGGGGSGG GGGGSRVQ PTESIVRFPN   300
ITNLCPFGEV FNATRFASVY AWNRKRISNC VADYSVLYNS ASFSTFKCYG VSPTKLNDLC   360
FTNVYADSFV IRGDEVRQIA PGQTGNIADY NYKLPDDFTG CVIAWNSNNL DSKVGGNYNY   420
LYRLFRKSNL KPFERDISTE IYQAGSTPCN GVKGFNCYFP LQSYGFQPTY GVGYQPYRVV   480
VLSFELLHAP ATVCGPKKST NLVKNKCVNF NAVGQDTQEV IVVPHSLPFK VVVISAILAL   540
VVLTIISLII LIMLWQKKPR                                                560

SEQ ID NO: 26              moltype = DNA  length = 1683
FEATURE                    Location/Qualifiers
misc_feature               1..1683
                           note = Description of Artificial Sequence: Synthetic
                                 polynucleotide
source                     1..1683
                           mol_type = other DNA
                           organism = synthetic construct
SEQUENCE: 26
atggacgcta tgaagagggg tctctgctgt gtcctcctc tgtgcggtgc cgtctttgtg    60
tctgcctctg aagtacaatt ggtggagtct gggggaggcc ttgtccaacc aggcgggtct   120
ttgcgactgt catgcgccgc ctctgggttt acattcaaca catatgctat gaattgggtc   180
cgacaagcgc cgggacaaagg actgaagtg gtcgcccgca ttcgctcaaa gtataacaat   240
tatgccacat attacgctgc gtcagtgaaa ggacggttca aatatcacg agacgattct   300
aaaaactcac tgtatctcca aatgaatagc ctcaaaacgg aggacactgc agtctattat   360
tgcgctcgac atggcaattt tggaaatagc tatgtatcct ggtttgcgta ctggggccaa   420
gggacgctgg tgactgtttc aagcggtggc ggcggatccg gtgaggagg cagcggcggt   480
ggtggctccc aaaccgttgt cacccaagag ccttctctca gtgtgtcccc tggtggcaca   540
```

```
gtgactttga cttgtaggtc ttctacaggc gcggtcacga ccagtaatta tgctaattgg   600
gtccagcaga aaccggggca ggcgccaaga ggtctcatag gggggacaaa taaacgcgcg   660
ccgggtacgc ctgcacgatt cagcggatcc ttgctgggcg gcaaggcagc ccttacgctc   720
tccgggttc agcccgaaga cgaggcagaa tactattgtg cgctgtggta tagtaatctt    780
tgggtatttg gaggaggtac aaaattgacc gtgttggtg gaggaggatc cggggggaggc   840
ggaagcgggg gtggcggttc tcgagtgcag ccgacggagt caatcgtgag attccctaac   900
ataactaatt tgtgtccatt tggcgaagtg ttcaatgcaa ccagattcgc ctccgtctat   960
gcgtggaatc gaaaagaat ttcaaactgc gtagcggatt attctgtctt gtacaatagt   1020
gcctcccttta gtacgttcaa gtgttatggg gtgtcaccaa cgaagttgaa tgatctttgt   1080
ttcacgaatg tttacgctga ttcatttgta atacgcggag acgaagttag acaaatcgca   1140
ccagggcaga caggcaacat cgcggattat aattataagc tgccagacga cttcactggg   1200
tgcgttatcg catggaactc caacaacttg atagtaaaa tgggcgggaa ttacaactac   1260
ctgtatagac ttttccgaaa gtccaatttg aagccattcg aaagggacat ttctactgaa   1320
atatatcaag cgggatcaac accttgcaac ggagtgaaag ggttcaactg ctactttccg   1380
ctgcaatctt atgggtttca accgactaat ggagtcgggt atcagcctta cagagttgtt   1440
gttctttcct ttgagctgtt gcatgccccg gcaaccgtat gtgggcccaa gaaatctaca   1500
aacctcgtta agaataaatg cgtgaatttc aacgctgtgg gcaagatac tcaggaggtc    1560
atcgttgtcc cacattcact gccttttaag gtcgttgtga tatccgcaat tcttgcgctg   1620
gtggtactta caataataag cctcataatc cttataatgc tctggcaaaa gaagccacgc   1680
tag                                                                 1683

SEQ ID NO: 27          moltype = AA   length = 509
FEATURE                Location/Qualifiers
REGION                 1..509
                       note = Description of Artificial Sequence: Synthetic
                        polypeptide
source                 1..509
                       mol_type = protein
                       organism = synthetic construct
SEQUENCE: 27
MDAMKRGLCC VLLLCGAVFV SASQVQLQQS GPEVVKPGAS VKMSCKASGY TFTSYVIHWV    60
RQKPGQGLDW IGYINPYNDG TDYDEKFKGK ATLTSDTSTS TAYMELSSLR SEDTAVYYCA   120
REKDNYATGA WFAYWGQGTL VTVSSGGGGS GGGGSGGGGS DIVMTQSPDS LAVSLGERVT   180
MNCKSSQSLL YSTNQKNYLA WYQQKPGQSP KLLIYWASTR ESGVPDRFSG SGSGTDFTLT   240
ISSVQAEDVA VYYCQQYYSY RTFGGGTKLE IKGGGGSGGG GSGGGGSRVQ PTESIVRFPN   300
ITNLCPFGEV FNATRFASVY AWNRKRISNC VADYSVLYNS ASFSTFKCYG VSPTKLNDLC   360
FTNVYADSFV IRGDEVRQIA PGQTGKIADY NYKLPDDFTG CVIAWNSNNL DSKVGGNYNY   420
LYRLFRKSNL KPFERDISTE IYQAGSTPCN GVEGFNCYFP LQSYGFQPTN GVGYQPYRVV   480
VLSFELLHAP ATVCGPKKST NLVKNKCVN                                     509

SEQ ID NO: 28          moltype = DNA   length = 1533
FEATURE                Location/Qualifiers
misc_feature           1..1533
                       note = Description of Artificial Sequence: Synthetic
                        polynucleotide
source                 1..1533
                       mol_type = other DNA
                       organism = synthetic construct
SEQUENCE: 28
atggatgcaa tgaagagagg gctctgctgt gtgctgctgc tgtgtggagc agtcttcgtt     60
tcggctagcc aggtacagct ccaacagtcc ggtccagagg tcgtgaaacc tggtgcatcc   120
gttaaaatga gttgcaaagc ttccggttat acgttcacat cttacgttat ccattgggtt   180
cgccagaaac cgggtcaggg acttgactgg atcggttata taaatccgta caatgatggc   240
accgactacg acgagaaatt caaaggaaag gctacactta cgtctgatac gagtacctca   300
actgcttaca tggaactttc ctctttgagg tctgaagaca cggcagttta ctattgtgcc   360
agagaaaaag ataattatgc cacgggagct tggttcgcat actggggca aggaacattg   420
gttacggtaa gtagtggggg aggcggaagt ggggcggag gctcaggtgg tgggggttca   480
gatattgtga tgacacagag cccggacagt cttgcagtga gtctcggcga acgcgttacc   540
atgaattgta agagtagtca gtctctcttg tatagcacta atcaaaagaa ttatttggca   600
tggtaccaac agaagccggg tcagtctcct aaactgctga tttactgggc gtcaacacgg   660
gagtctggag ttccggatcg attctccgga tctggaagcg gtactgactt caccctcacg   720
atctcaagtg tgcaagcgga ggacgttgcg gtgtattact gccaacagta ttattcttac   780
cgaacattcg gcggtgggac caagctgaa ataaaggggg tggcggcag tggcggtggc   840
gggtcggag gtggggttc ccgagtgcag ccgacggagt caatcgtgag attccctaac   900
ataactaatt tgtgtccatt tggcgaagtg ttcaatgcaa ccagattcgc ctccgtctat   960
gcgtggaatc gaaaagaat ttcaaactgc gtagcggatt attctgtctt gtacaatagt   1020
gcctcccttta gtacgttcaa gtgttatggg gtgtcaccaa cgaagttgaa tgatctttgt   1080
ttcacgaatg tttacgctga ttcatttgta atacgcggag acgaagttag acaaatcgca   1140
ccagggcaga caggcaagat cgcggattat aattataagc tgccagacga cttcactggg   1200
tgcgttatcg catggaactc caacaacttg atagtaaaa tgggcgggaa ttacaactac   1260
ctgtatagac ttttccgaaa gtccaatttg aagccattcg aaagggacat ttctactgaa   1320
atatatcaag cgggatcaac accttgcaac ggagtgaaag ggttcaactg ctactttccg   1380
ctgcaatctt atgggtttca accgactaat ggagtcgggt atcagcctta cagagttgtt   1440
gttctttcct ttgagctgtt gcatgccccg gcaaccgtat gtgggcccaa gaaatctaca   1500
aacctcgtta agaataaatg cgtgaatttc tag                                1533

SEQ ID NO: 29          moltype = AA   length = 5
FEATURE                Location/Qualifiers
REGION                 1..5
```

```
                    note = Description of Artificial Sequence: Synthetic peptide
source              1..5
                    mol_type = protein
                    organism = synthetic construct
SEQUENCE: 29
GGGGS                                                                              5
```

What is claimed is:

1. A recombinant nucleic acid encoding a conjugate polypeptide, wherein the conjugate polypeptide comprises an amino acid sequence that has at least 85% sequence identity to any one of SEQ ID NOs: 1, 6, 9, 11, 13, 15, 17, 19, 21, 23, or 25.

2. The recombinant nucleic acid of claim 1, wherein the conjugate polypeptide comprises a first peptide comprising an antigen from SARS-CoV-2.

3. The recombinant nucleic acid of claim 2, wherein the antigen comprises a SARS-CoV-2 S1 domain or a receptor-binding domain (RBD).

4. The recombinant nucleic acid of claim 2, wherein the conjugate polypeptide comprises a second peptide that is capable of binding to CD2 or CD3.

5. The recombinant nucleic acid of claim 4, wherein the second peptide comprises a single-chain variable fragment (scFv).

6. The recombinant nucleic acid of claim 5, wherein the scFv is an anti-CD2 or anti-CD3 scFv.

7. The recombinant nucleic acid of claim 6, wherein the anti-CD2 scFv comprises LO-CD2a.

8. The recombinant nucleic acid of claim 6, wherein the anti-CD3 scFv comprises the heavy- and light-chain variable regions of SP34.

9. The recombinant nucleic acid of claim 1, wherein the recombinant nucleic acid is deoxyribonucleic acid (DNA) or ribonucleic acid (RNA).

10. The recombinant nucleic acid of claim 4, wherein a first polynucleotide encoding the first peptide and a second polynucleotide encoding the second peptide are present within an expression cassette, wherein the expression cassette is present in a vector.

11. The recombinant nucleic acid of claim 10, wherein the vector is a non-viral vector.

12. The recombinant nucleic acid of claim 11, wherein the non-viral vector is a nanoparticle.

13. The recombinant nucleic acid of claim 10, wherein the vector is a viral vector.

14. The recombinant nucleic acid of claim 13, wherein the viral vector is a self-launching cytomegalovirus (SLCMV), adenovirus, or adeno-associated virus (AAV) vector.

15. The recombinant nucleic acid of claim 1, wherein the conjugate polypeptide comprises the amino acid sequence set forth in any one of SEQ ID NOs: 1, 6, 9, 11, 13, 15, 17, 19, 21, 23, or 25.

16. The recombinant nucleic acid of claim 1, wherein the conjugate polypeptide further comprises a lipid anchor, a transmembrane segment, a multimerizing domain, or any combinations thereof.

17. The recombinant nucleic acid of claim 16, wherein the multimerizing domain is an Fc domain.

18. The recombinant nucleic acid of claim 4, wherein the conjugate polypeptide further comprises a third peptide comprising a second antigen, the third peptide is linked to the conjugate polypeptide, and the second antigen is different from the antigen comprised in the first peptide.

19. The recombinant nucleic acid of claim 1, wherein the antigen is embedded in a nanodisc.

20. The recombinant nucleic acid of claim 1, wherein the conjugate polypeptide is a dimer.

21. The recombinant nucleic acid of claim 1, wherein the conjugate polypeptide comprises an amino acid sequence that has at least 90% sequence identity to SEQ ID NO: 6.

22. The recombinant nucleic acid of claim 1, wherein the conjugate polypeptide comprises an amino acid sequence that has at least 95% sequence identity to SEQ ID NO: 6.

23. The recombinant nucleic acid of claim 1, wherein the conjugate polypeptide comprises an amino acid sequence that has at least 99% sequence identity to SEQ ID NO: 6.

24. The recombinant nucleic acid of claim 1, wherein the conjugate polypeptide comprises the amino acid sequence set forth in SEQ ID NO: 6.

25. The recombinant nucleic acid of claim 1, wherein the conjugate polypeptide comprises an amino acid sequence that has at least 90% sequence identity to any one of SEQ ID NOs: 1, 6, 9, 11, 13, 15, 17, 19, 21, 23, or 25.

26. The recombinant nucleic acid of claim 1, wherein the conjugate polypeptide comprises an amino acid sequence that has at least 95% sequence identity to any one of SEQ ID NOs: 1, 6, 9, 11, 13, 15, 17, 19, 21, 23, or 25.

27. The recombinant nucleic acid of claim 1, wherein the conjugate polypeptide comprises an amino acid sequence that has at least 99% sequence identity to any one of SEQ ID NOs: 1, 6, 9, 11, 13, 15, 17, 19, 21, 23, or 25.

* * * * *